United States Patent
Redman-Furey et al.

(10) Patent No.: US 9,035,052 B2
(45) Date of Patent: May 19, 2015

(54) COMPOSITIONS OF AZIMILIDE DIHYDROCHLORIDE

(71) Applicant: WARNER CHILCOTT COMPANY, LLC, Fajardo, PR (US)

(72) Inventors: Nancy Lee Redman-Furey, Morrow, OH (US); Nicholas William Geary, Cincinnati, OH (US); Tammy Baker, South Lebanon, OH (US)

(73) Assignee: Warner Chilcott Company, LLC, Fajardo, PR (US)

( * ) Notice: Subject to any disclaimer, the term of this patent is extended or adjusted under 35 U.S.C. 154(b) by 7 days.

(21) Appl. No.: 13/840,612

(22) Filed: Mar. 15, 2013

(65) Prior Publication Data

US 2013/0217701 A1    Aug. 22, 2013

Related U.S. Application Data

(63) Continuation of application No. 13/365,576, filed on Feb. 3, 2012, now abandoned, which is a continuation-in-part of application No. 13/156,810, filed on Jun. 9, 2011, now abandoned, which is a continuation of application No. 12/001,321, filed on Dec. 11, 2007, now abandoned.

(60) Provisional application No. 60/875,051, filed on Dec. 15, 2006.

(51) Int. Cl.
| | |
|---|---|
| *C07D 403/00* | (2006.01) |
| *C07D 233/00* | (2006.01) |
| *C07D 405/12* | (2006.01) |
| *A61K 31/496* | (2006.01) |

(52) U.S. Cl.
CPC ............ *C07D 405/12* (2013.01); *A61K 31/496* (2013.01)

(58) Field of Classification Search
CPC . A61K 31/496; A61K 31/4178; C07D 405/14
USPC ........................................................ 544/370
See application file for complete search history.

(56) References Cited

U.S. PATENT DOCUMENTS

| 5,462,940 | A | 10/1995 | Yu et al. |
| 6,414,151 | B1 | 7/2002 | Matson et al. |
| 6,420,568 | B1 | 7/2002 | Matson et al. |
| 2004/0224982 | A1 | 11/2004 | Axt et al. |

FOREIGN PATENT DOCUMENTS

| JP | 6-509804 | A | 11/1994 |
| JP | 2002-513022 | A | 5/2002 |
| WO | 93/04061 | A1 | 3/1993 |
| WO | 99/55701 | A1 | 11/1999 |

OTHER PUBLICATIONS

English language translation of "Wermuth", author is actually Anderson et al., 17 pages.*
English Language Translation of "Okano", 9 pages.*
English Language Translation of "Ogata", 13 pages.*
Espacenet Patent Family Listing for JP-2002-513022.*
Espacenet Patent Family Listing for JP H06-509804.*
English Language Translation of "Wermuth", author is actually Anderson et al., 17 pages, original publication date of "Wermut" is Sep. 25, 1999.*
English Translation of "Okano", 9 pages, original publication date of Okano is Apr. 10, 1987.*
English Translation of "Ogata", 13 pages, original publication date for Ogata is Nov. 20, 1963.*
Espacenet Patent Family Listing for JP-2002-513022, publication date of application is 2002.*
Espacenet Patent Family Listing for JP H06-509804, publication date for application is 1994.*
Wermuth, C.G., "The Practice of Medical Chemistry vol. 2," Technomics, Inc., pp. 347-348, 359-360, 452-453, Sep. 25, 1999.
Ogata, A., "Method of Operating Chemical Experiments vol. 1," Nankodo Co., Ltd., 27th edition, pp. 377-379, 383-384, Nov. 20, 1963.
Okano, S., "New Theory of Pharmaceutics (The Third Edition)," Nankodo Co., Ltd., pp. 111, 256, 257, Apr. 10, 1987.
Examination Report issued in Australian Patent Application No. 2007331033, 2 pages, dated Apr. 24, 2012.
Office Action issued in Canadian Patent Application No. 2,672,132, 2 pages, dated Nov. 17, 2011.
Official Notice of Rejection issued in Japanese Patent Application No. 2009-540950, 3 pages, dated Jun. 12, 2012.
Examination Report issued in New Zealand Patent Application No. 576958, 2 pages, dated Sep. 3, 2010.
Vippagunta et al., "Crystalline Solids", Advanced Drug Delivery Reviews, 48:3-26 (2001).
Redman-Furey et al., "Structural and Analytical Characterization of Three Hydrates and an Anhydrate Form of Risedronate", Journal of Pharmaceutical Sciences, 94 (4): 893-911 (Apr. 2005).
Hausman et al. "Application of Raman Spectroscopy for On-line Monitoring of Low Dose Blend Uniformity", International Journal of Pharmaceutics, 298:80-90 (2005).
Salata et al., "Pharmacology of Azimilide Dihydrochloride (NE-10064). A Class III Antiarrhythmic Agent", Cardiovascular Drug Reviews, 15 (2): 137-56 (1997).
Remington's Pharmaceutical Sciences, 15th Edition, pp. 1035-1038 and 1570-1580 (1975).
Caira, "Crystalline Polymorphism of Organic Compounds", Topics in Current Chemistry, Springer, Berlin, DE, vol. 198, pp. 163-208 (Jan. 1998).

(Continued)

*Primary Examiner* — James D Anderson
*Assistant Examiner* — Meghan Finn
(74) *Attorney, Agent, or Firm* — Fitzpatrick, Cella, Harper & Scinto

(57) ABSTRACT

The present invention is directed to solvates and various polymorphic forms of (E)-1-[[[5-(4-chlorophenyl)-2-furanyl]methylene]amino]-3-[4-(4-methyl-1-piperazinyl)butyl]-2,4-imidazolidinedione dihydrochloride and pharmaceutical compositions thereof.

13 Claims, 12 Drawing Sheets

(56) References Cited

OTHER PUBLICATIONS

Clemett et al., "Azimilide" Drugs, 59 (2): 271-77 (Jan. 2000).
International Search Report and Written Opinion issued in International Application No. PCT/IB2007/055037, 15 pages, mailed Sep. 17, 2008.
Communication issued in European Application No. EP 07 849 435.8, 4 pages, dated Nov. 25, 2010.
Office Action issued in Chinese Application No. 200780046423.5, 9 pages, dated Feb. 9, 2011.
Notice of Grounds for Rejection issued in Korean Application No. 2009-7012327, 8 pages, dated Mar. 17, 2011.
Office Action issued in Taiwanese Application No. 096146861, 9 pages, dated Dec. 7, 2010.
Office Action in U.S. Appl. No. 13/156,810, 7 pages, dated Mar. 29, 2012.

\* cited by examiner

COMPOSITIONS OF AZIMILIDE DIHYDROCHLORIDE

CROSS REFERENCE TO RELATED APPLICATIONS

This application is a continuation of U.S. patent application Ser. No. 13/365,576, filed Feb. 3, 2012, which is a continuation-in-part of U.S. patent application Ser. No. 13/156,810, filed on Jun. 9, 2011, now abandoned, which is a continuation of U.S. patent application Ser. No. 12/001,321, filed Dec. 11, 2007, now abandoned, which claims the benefit of U.S. Provisional Application No. 60/875,051, filed on Dec. 15, 2006. All prior applications are hereby incorporated by reference herein in their entireties.

TECHNICAL FIELD

The present invention relates to solvates and polymorphs of (E)-1-[[[5-(4-chlorophenyl)-2-furanyl]methylene]amino]-3-[4-(4-methyl-1-piperazinyl)butyl]-2,4-imidazolidinedione dihydrochloride and the use of such compositions in pharmaceutical products.

BACKGROUND OF THE INVENTION

Azimilide, (E)-1-[[[5-(4-chlorophenyl)-2-furanyl]methylene]amino]-3-[4-(4-methyl-1-piperazinyl)butyl]-2,4-imidazolidinedione dihydrochloride, is a compound useful to treat cardiac arrhythmias. Azimilide, a novel class III antiarrhythmic agent, blocks both the slowly activating and rapidly activating components of the delayed rectifier potassium current, which distinguishes it from conventional potassium channel blockers such as sotalol and dofetilide, which block only rapidly activating components. Azimilide is being developed to prolong the time to recurrence of atrial fibrillation, atrial flutter, and paroxysmal supraventricular tachycardia in patients with and without structural heart disease.

U.S. Pat. No. 5,462,940 describes the class of compound of 4-oxocyclic ureas, including azimilide, and the pharmaceutically acceptable salts and esters thereof, of the present invention are useful as antiarrhythmic and antifibrillatory agents. U.S. Pat. Nos. 6,414,151 and 6,420,568 describe processes for making compounds useful in the treatment of various medical disorders; such uses include but are not limited to uses as antifibrillatory and antiarrhythmic agents. The '151 patent teaches high yield synthetic pathways for making 1,3-disubstituted-4-oxocyclic ureas, particularly Amilizide or salts thereof.

Optimization of the choice of suitable solid state forms to yield useful preparations for the manufacture of a pharmaceutically acceptable composition has not been described. Therefore, there is a need in the art to develop optimized solid state forms of Azimilide, (E)-1-[[[5-(4-chlorophenyl)-2-furanyl]methylene]amino]-3-[4-(4-methyl-1-piperazinyl)butyl]-2,4-imidazolidinedione dihydrochloride.

BRIEF SUMMARY OF THE INVENTION

The inventors have found that two solvates and an anhydrate form of azimilide are particularly advantageous for the manufacture of pharmaceutically acceptable compositions. The different crystal forms (i.e., "polymorphs") are used to enhance finished pharmaceutical preparations of azimilide.

The present invention relates to the hemi-hydrate, anhydrate and isopropanol solvates of the dihydrochloride salts of (E)-1-[[[5-(4-chlorophenyl)-2-furanyl]methylene]amino]-3-[4-(4-methyl-1-piperazinyl)butyl]-2,4-imidazolidinedione.

In one aspect of the present invention, there is a hemi-hydrate azimilide composition having between about 0.5% and about 2.5% (w/w) of water. In some embodiments, the composition has an X-ray diffraction pattern characterized substantially in accordance with the pattern of FIG. 1. In some embodiments, the composition has a solid-state $^{13}C$ NMR spectrum characterized substantially in accordance with the solid-state $^{13}C$ NMR spectrum of FIG. 4. In some embodiments, the composition has an infrared spectrum characterized substantially in accordance with the infrared spectrum of FIG. 7. In some embodiments, the composition has a thermogravimetric analysis curve characterized substantially in accordance with the pattern of FIG. 10. In some embodiments, the composition has X-ray diffraction peaks at 2 theta values of about 5.95 degrees, about 11.9 degrees, about 14.88 degrees, about 17.66 degrees, about 20.89 degrees and about 26.03 degrees. In some embodiments, the composition has IR absorbance peaks at about 3512 and 3450 wavenumbers. In preferred embodiments, the azimilide composition has between about 0.5% and about 2.5% (w/w) of water and further comprises a pharmaceutically acceptable carrier. There is also a method of treating or preventing cardiac arrhythmias in a human or other animal in need of such treatment, comprising: (a) identifying a human or other animal in need of treating or preventing an infectious disorder; and, (b) administering to the human or other animal an effective amount of an azimilide composition having between about 0.5% and about 2.5% (w/w) of water.

In another aspect of the present invention, there is an anhydrate azimilide composition having between about 0% and about 0.3% (w/w) of residual water. In some embodiments, the composition has an X-ray diffraction pattern characterized substantially in accordance with the pattern of FIG. 2. In some embodiments, the composition has a solid-state $^{13}C$ NMR spectrum characterized substantially in accordance with the solid-state $^{13}C$ NMR spectrum of FIG. 5. In some embodiments, the composition has an infrared spectrum characterized substantially in accordance with the infrared spectrum of FIG. 8. In some embodiments, the composition has a thermogravimetric analysis curve characterized substantially in accordance with the pattern of FIG. 11. In some embodiments, the composition has X-ray diffraction peaks at 2 theta values of about 4.96 degrees, about 9.25 degrees, about 9.92 degrees, about 14.9 degrees, about 21.17 degrees, and about 24.56 degrees. In preferred embodiments, the azimilide composition has between about 0% and about 0.3% (w/w) of residual water and further comprises a pharmaceutically acceptable carrier. There is also a method of treating or preventing cardiac arrhythmias in a human or other animal in need of such treatment, comprising: (a) identifying a human or other animal in need of treating or preventing an infectious disorder; and, (b) administering to the human or other animal an effective amount of an azimilide composition having between about 0% and about 0.3% (w/w) of residual water.

In another aspect of the present invention, there is an isopropanol solvate azimilide composition having between about 9% and about 11% isopropanol by weight. In some embodiments, the composition has an X-ray diffraction pattern characterized substantially in accordance with the pattern of FIG. 3. In some embodiments, the composition has a solid-state $^{13}C$ NMR spectrum characterized substantially in accordance with the solid-state $^{13}C$ NMR spectrum of FIG. 6. In some embodiments, the composition has an infrared spectrum characterized substantially in accordance with the infrared spectrum of FIG. 9. In some embodiments, the composition has a thermogravimetric analysis curve characterized substantially in accordance with the pattern of FIG. 12. In some embodiments, the composition has X-ray diffraction peaks at 2 theta values of about 4.33, about 9.51, about 12.8, about 17.16, about 18.5 and about 21.53 degrees. In some embodiments, the composition has IR absorbance peaks at about 3428 and 3390 wavenumbers. In preferred embodiments, the azimilide composition has between about 9% and about 11% isopropanol by weight and further comprises a pharmaceutically acceptable carrier. There is also a method of treating or preventing cardiac arrhythmias in a human or other animal in need of such treatment, comprising: (a) identifying a human or other animal in need of treating or preventing an infectious disorder; and, (b) administering to the human or other animal an effective amount of an azimilide composition having between about 9% and about 11% isopropanol by weight.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which.

DETAILED DESCRIPTION OF THE INVENTION

Figure 1:
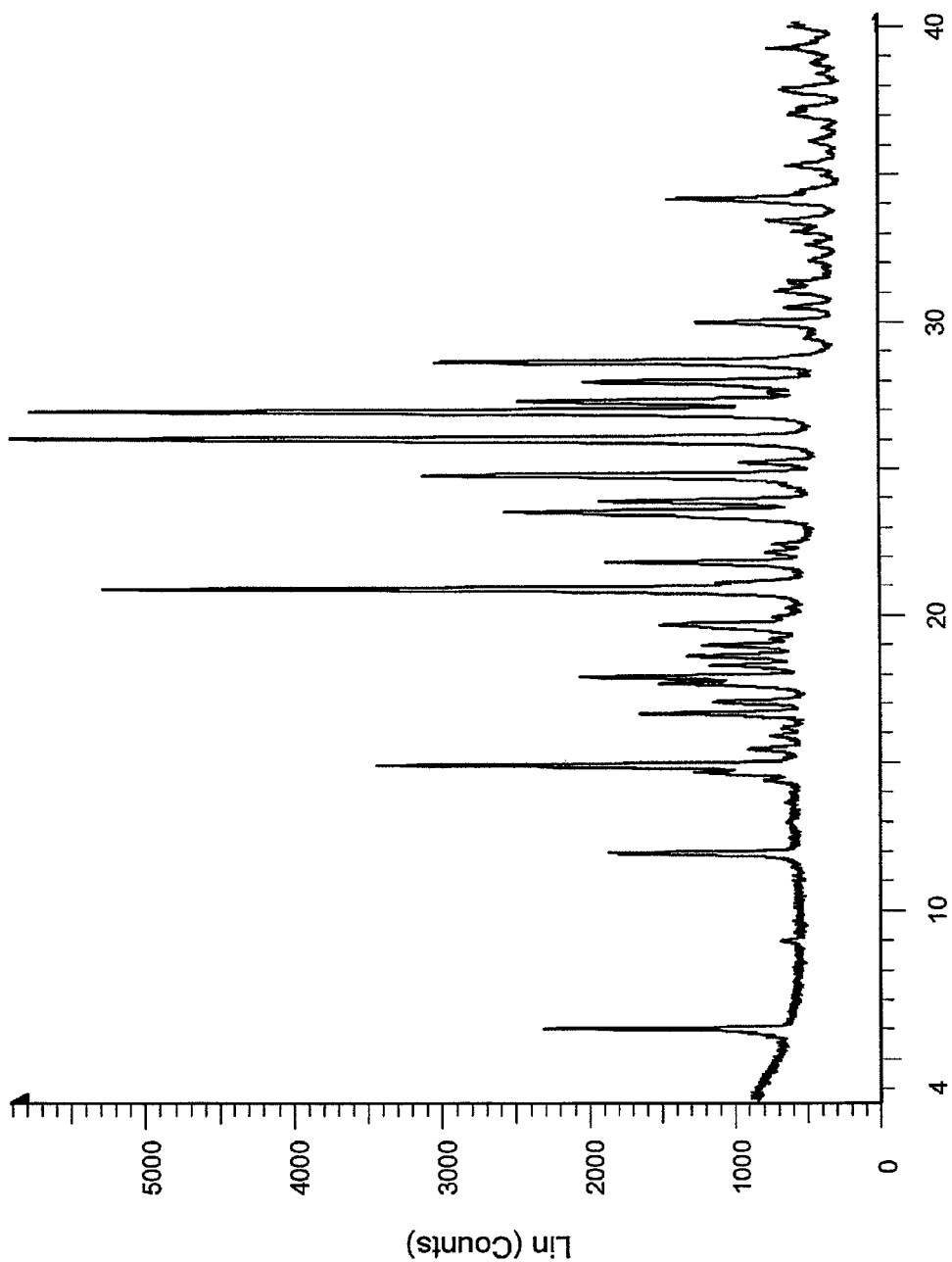
FIG. 1 shows a representative X-ray Diffraction Pattern for the hemi-hydrate of Azimilide.

As used herein, "a", "an" and "the" mean "one or more". Unless otherwise indicated, the singular contains the plural and the plural contains the singular.

As used herein, "Azimilide" means the dihydrochloride salts of (E)-1-[[[5-(4-chlorophenyl)-2-furanyl]methylene]amino]-3-[4-(4-methyl-1-piperazinyl)butyl]-2,4-imidazolidinedione. These dihydrochloride salts may contain as much as 3% by weight bromide, or calculated another way, up to 10% of the counterions may be hydrobromide.

Herein are described two solvates, namely the hemi-hydrate and isopropanol solvate, and an anhydrate form of Azimilide. Selection of a pharmaceutically acceptable solid state form with desirable characteristics (e.g., solubility, stability, formulation ease) requires evaluation of many salts and resulting polymorphs (See Handbook of Pharmaceutical Salts, Properties, Selection and Use. Edited by P. H. Stahl, C. G. Wermuth (Wiley-VCH, Zurich, 2002) and Polymorphism in Pharmaceutical Solids. Edited by Harry G. Brittain (Marcell Dekker, New York 1999)).

Solids exist in either amorphous or crystalline forms. In the case of crystalline forms, molecules are positioned in 3-dimensional lattice sites. When a compound crystallizes from a solution or slurry, it may crystallize with different spatial lattice arrangements, a property referred to as "polymorphism", with the different crystal forms individually being referred to as a "polymorph". Different polymorphic forms of a given substance may differ from each other with respect to one or more physical properties, such as solubility and dissolution rate, true density, crystal shape, compaction behavior, flow properties, and/or solid-state stability.

Crystallization

Manufacturing scale crystallizations are achieved by manipulating a solution so that the solubility limit for the compound of interest is exceeded. This may be achieved by a variety of methods, e.g., dissolving the compound at a relatively high temperature and then cooling the solution to below the saturation limit. Alternatively, the liquid volume may be reduced by boiling, ambient pressure evaporation, vacuum drying or by some other means. Solubility of the compound of interest may be decreased by the addition of an anti-solvent or a solvent in which the compound exhibits reduced solubility or a mixture of such solvents. Another option may be pH adjustment to reduce solubility. For detailed description on crystallization, please see Crystallization, 3d edition, J W Mullens, Butterworth-Heineman Ltd, 1993, ISBN 0750611294.

If salt formation is desired concurrent with crystallization, addition of the appropriate acid or base may result in direct crystallization of the desired salt, if the salt is less soluble in the reaction media than the starting material. Likewise, completion of a synthetic reaction in a medium in which the final desired form is less soluble than the reactants may enable direct crystallization of the final product.

Optimization of the crystallization may include seeding of the crystallization medium with crystals of the desired form. In addition, many crystallization processes use combinations of the above-described strategies. An example would be the dissolution of the compound of interest in a solvent at high temperature, followed by controlled addition of an anti-solvent in a volume adequate to bring the system just below the saturation level. At this point, seeds of the desired form may be added, and with the seeds intact, the system is cooled to achieve the crystallization.

Pharmaceutical Formulations and Methods for Use

This invention also provides methods of treating or preventing cardiac arrhythmias. The salts or polymorphs of the invention are administered to treat or to prevent various cardiovascular diseases, such as cardiac arrhythmias.

A pharmaceutical composition may comprise: (a) a safe and effective amount of a salt or a polymorph of the invention; and (b) a pharmaceutically-acceptable carrier.

The term "treatment" is used herein to mean that administration of a compound of the present invention mitigates a disease or a disorder in a host. Thus, the term "treatment" includes, preventing a disorder from occurring in a host, particularly when the host is predisposed to acquiring the disease, but has not yet been diagnosed with the disease; inhibiting the disorder; and/or alleviating or reversing the disorder. Insofar as the methods of the present invention are directed to preventing disorders, it is understood that the term "prevent" does not require that the disease state be completely thwarted. (See Webster's Ninth Collegiate Dictionary.) Rather, as used herein, the term preventing encompasses to the ability of the skilled artisan to identify a population that is susceptible to disorders, such that administration of the compounds of the present invention may occur prior to onset of a disease. The term does not imply that the disease state be completely avoided. The compounds identified by the screening methods of the present invention may be administered in conjunction with other compounds.

Safety and therapeutic efficacy of compounds identified may be determined by standard procedures using in vitro or in vivo technologies. Compounds that exhibit sufficient therapeutic indices may be preferred, although compounds with otherwise insufficient therapeutic indices may also be useful. The data obtained from the in vitro and in vivo toxicological and pharmacological techniques may be used to formulate the range of doses. Effectiveness of a compound may further be assessed either in animal models or in clinical trials of patients.

A "safe and effective amount" of a compound of the invention is an amount "that is effective to treat cardiac arrhythmias with acceptable side effects (such as toxicity, irritation, or allergic response). The specific "safe and effective amount" will vary with such factors as the particular condition being treated, the physical condition of the patient, the duration of treatment, the nature of concurrent therapy (if any), the specific dosage form to be used, the excipients(s) employed, and the dosage regimen desired for the composition. For example, a safe and effective amount of Azimilide to be administered daily can range from 5-500 mg, preferably 25-250 mg and more preferably 50-175 mg when administered orally.

As used herein, "pharmaceutically acceptable carrier" is intended to include solvents, dispersion media, coatings, antibacterial and antifungal agents, isotonic and absorption delaying agents, and the like, compatible with pharmaceutical administration. The use of such media and agents for pharmaceutically active substances is known in the art. Except insofar as any conventional media or agent is incompatible with the compound, such media may be used in the compositions of the invention. Supplementary compounds may also be incorporated into the compositions. A pharmaceutical composition of the invention is formulated to be compatible with its intended route of administration. Examples of routes of administration include parenteral, (e.g., intravenous, intradermal, subcutaneous, intramuscular), oral, inhalation, transdermal (topical), transmucosal, and rectal administration. Solutions or suspensions used for parenteral, intradermal, or subcutaneous application may include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH may be adjusted with suitable acids or bases. The parenteral preparation may be enclosed in ampoules, disposable syringes or multiple dose vials made of glass or plastic.

Pharmaceutical formulations of the present invention comprise an effective amount of a composition of the present invention dissolved and/or dispersed in a pharmaceutically acceptable carrier and/or aqueous or non-aqueous media.

The phrases pharmaceutically and/or pharmacologically acceptable refer to molecular entities and/or compositions that do not produce an adverse, allergic and/or other untoward reaction when administered to an animal, as appropriate.

As used herein, pharmaceutically acceptable carrier includes any and/or all solvents, dispersion media, coatings, antibacterial and/or antifungal agents, isotonic and/or absorption delaying agents and/or the like. The use of such media and/or agents for pharmaceutical active substances is well known in the art. Except insofar as any conventional media and/or agent is incompatible with the active ingredient, its use in the therapeutic compositions is contemplated. Supplementary active ingredients can also be incorporated into the compositions. For administration, preparations should meet sterility, pyrogenicity, general safety and/or purity standards as required by Regulatory Agency standards.

Azimilide forms that meet Regulatory Agency standards for safety and purity can be achieved in any suitable manner. In some preferred embodiments, the azimilide anhydrate, isopropanol solvate and hemi-hydrate forms are made to meet Regulatory Agency standards for safety and/or purity, e.g., by ensuring sufficient exposure of the azimilide forms to crystallization processes and solutions during preparation. In this manner, the azimilide forms can be made to comply for example with Regulatory Agency-defined specifications (or maximum permitted concentration levels) for specific impurities (e.g., degradants and/or process impurities such as process intermediates). In some embodiments, the preparation process involves multiple crystallization steps, for example two or more sequential crystallization steps using the same or similar solutions and conditions.

In some preferred embodiments, the preparation and/or purification of azimilide hemi-hydrate comprises subjecting azimilide hemi-hydrate (e.g., prepared as described in examples 1, 2, or the like) to one or more subsequent crystallization steps. The subsequent crystallization step(s) can comprise contacting the hemi-hydrate with any suitable crystallization solution such as the solutions described in examples 1 or 2 or the like. For example, a crystallization solution comprising any suitable volume ratio of acetone:water can be used in some embodiments (e.g., a crystallization solution comprising a volume ratio of acetone:water between 4:3 and 10:3, between about 5:3 and about 9:3, or even between about 8:3 and about 10:3). In some embodiments, azimilide hemi-hydrate which meets Regulatory Agency standards for safety and/or purity is prepared by a process that comprises two crystallization steps using the same or different aqueous acetone solutions (e.g., two solutions having different volume ratios of acetone:water).

In some embodiments, the azimilide hemi-hydrate comprises between 0.000001% and 0.0025% by weight of 1-[[[5-(4-Chlorophenyl)-2-furanyl]methylene]amino]-3-[4-(chloro)butyl]-2,4-imidazolidinedione (i.e., 3-[4-(chlorobutyl)-1-[[[5-(4-chlorophenyl)-2-furanyl]methylene]amino]-2,4-imidazolidinedione. In some embodiments, the azimilide hemi-hydrate comprises between 0.000001% and 0.0025% by weight of 1-[[[5-(4-Chlorophenyl)-2-furanyl]methylene]amino]-3-[4-(chloro)butyl]-2,4-imidazolidinedione. In some embodiments, the azimilide hemi-hydrate comprises between 0.0001% and 0.0025% by weight of 1-[[[5-(4-Chlorophenyl)-2-furanyl]methylene]amino]-3-[4-(chloro)butyl]-2,4-imidazolidinedione. In some embodiments, the azimilide hemi-hydrate comprises between 0.000001% and 0.0025% by weight of 1-[[[5-(4-Chlorophenyl)-2-furanyl]methylene]amino]-3-[4-(chloro)butyl]-2,4-imidazolidinedione. In some embodiments, the azimilide hemi-hydrate comprises between 0.000001% and 0.002% by weight of 1-[[[5-(4-Chlorophenyl)-2-furanyl]methylene]amino]-3-[4-(chloro)butyl]-2,4-imidazolidinedione. In some embodiments, the azimilide hemi-hydrate comprises between 0.000001% and 0.002% by weight of 1-[[[5-(4-Chlorophenyl)-2-furanyl]methylene]amino]-3-[4-(chloro)butyl]-2,4-imidazolidinedione. In some embodiments, the azimilide hemi-hydrate comprises between 0.0001% and 0.002% by weight of 1-[[[5-(4-Chlorophenyl)-2-furanyl]methylene]amino]-3-[4-(chloro)butyl]-2,4-imidazolidinedione. In some embodiments, the azimilide hemi-hydrate comprises between 0.000001% and 0.002% by weight of 1-[[[5-(4-Chlorophenyl)-2-furanyl]methylene]amino]-3-[4-(chloro)butyl]-2,4-imidazolidinedione. In some embodiments, the azimilide hemi-hydrate comprises between 0.000001% and 0.0015% by weight of 1-[[[5-(4-Chlorophenyl)-2-furanyl]methylene]amino]-3-[4-(chloro)butyl]-2,4-imidazolidinedione. In some embodiments, the azimilide hemi-hydrate comprises between 0.000001% and 0.0015% by weight of 1-[[[5-(4-Chlorophenyl)-2-furanyl]methylene]amino]-3-[4-(chloro)butyl]-2,4-imidazolidinedione. In some embodiments, the azimilide hemi-hydrate comprises between 0.0001% and 0.0015% by weight of 1-[[[5-(4-Chlorophenyl)-2-furanyl]methylene]amino]-3-[4-(chloro)butyl]-2,4-imidazolidinedione. In some embodiments, the azimilide hemi-hydrate comprises between 0.000001% and 0.0015% by weight of 1-[[[5-(4-Chlorophenyl)-2-furanyl]methylene]amino]-3-[4-(chloro)butyl]-2,4-imidazolidinedione.

Alternatively, or in addition in some embodiments, the azimilide hemi-hydrate comprises between 0.00001% and 0.2% by weight of 5-(4-chlorophenyl)-2-furancarboxaldehyde. In some embodiments, the azimilide hemi-hydrate comprises between 0.0001% and 0.1% by weight of 5-(4-chlorophenyl)-2-furancarboxaldehyde. In some embodiments, the azimilide hemi-hydrate comprises between 0.001% and 0.002% by weight of 5-(4-chlorophenyl)-2-furancarboxaldehyde.

Alternatively, or in addition in some embodiments, the azimilide hemi-hydrate comprises between 0.00001% and 0.2% by weight of 1-Amino-3-[4-(4-methyl-1-piperazinyl)butyl]-2,4-imidazolidinedione dihydrochloride. In some embodiments, the azimilide hemi-hydrate comprises between 0.0001% and 0.1% by weight of 1-Amino-3-[4-(4-methyl-1-piperazinyl)butyl]-2,4-imidazolidinedione dihydrochloride. In some embodiments, the azimilide hemi-hydrate comprises between 0.001% and 0.2% by weight of 1-Amino-3-[4-(4-methyl-1-piperazinyl)butyl]-2,4-imidazolidinedione dihydrochloride.

Alternatively, or in addition in some embodiments, the azimilide hemi-hydrate comprises between 0.00001% and 0.3% by weight of 3,3'-[1,4-Piperazinediylbis(butylene)]bis[1-[[[5-(4-chlorophenyl)-2-furanyl]methylene]amino]-2,4-imidazolidinedione]. In some embodiments, the azimilide hemi-hydrate comprises between 0.00001% and 0.2% by weight of 3,3'-[1,4-Piperazinediylbis(butylene)]bis[1-[[[5-(4-chlorophenyl)-2-furanyl]methylene]amino]-2,4-imidazolidinedione]. In some embodiments, the azimilide hemi-hydrate comprises between 0.00001% and 0.1% by weight of 3,3'-[1,4-Piperazinediylbis(butylene)]bis[1-[[[5-(4-chlorophenyl)-2-furanyl]methylene]amino]-2,4-imidazolidinedione]. In some embodiments, the azimilide hemi-hydrate comprises between 0.001% and 0.3% by weight of 3,3'-[1,4-Piperazinediylbis(butylene)]bis[1-[[[5-(4-chlorophenyl)-2-furanyl]methylene]amino]-2,4-imidazolidinedione].

Alternatively, or in addition in some embodiments, the azimilide hemi-hydrate comprises between 0.00001% and 0.5% by weight of 1,4-bis[4-[1-[[[5-(4-Chlorophenyl)-2-furanyl]methylene]amino]-2,4-dioxo-3-imidazolidinyl]butyl]-1-methylpiperazinium chloride. In some embodiments, the azimilide hemi-hydrate comprises between 0.00001% and 0.4% by weight of 1,4-bis[4-[1-[[[5-(4-Chlorophenyl)-2-furanyl]methylene]amino]-2,4-dioxo-3-imidazolidinyl]butyl]-1-methylpiperazinium chloride. In some embodiments, the azimilide hemi-hydrate comprises between 0.00001% and 0.3% by weight of 1,4-bis[4-[1-[[[5-(4-Chlorophenyl)-2-furanyl]methylene]amino]-2,4-dioxo-3-imidazolidinyl]butyl]-1-methylpiperazinium chloride. In some embodiments, the azimilide hemi-hydrate comprises between 0.00001% and 0.2% by weight of 1,4-bis[4-[1-[[[5-(4-Chlorophenyl)-2-furanyl]methylene]amino]-2,4-dioxo-3-imidazolidinyl]butyl]-1-methylpiperazinium chloride. In some embodiments, the azimilide hemi-hydrate comprises between 0.00001% and 0.1% by weight of 1,4-bis[4-[1-[[[5-(4-Chlorophenyl)-2-furanyl]methylene]amino]-2,4-dioxo-3-imidazolidinyl]butyl]-1-methylpiperazinium chloride.

Alternatively, or in addition in some embodiments, the azimilide hemi-hydrate comprises between 0.00001% and 0.5% by weight of 1,1'-[1,2-ethanediylbis(amino)]bis[3-[4-(4-methyl-1-piperazinyl)butyl]-2,4-imidazolidinedione]. In some embodiments, the azimilide hemi-hydrate comprises between 0.00001% and 0.4% by weight of 1,1'-[1,2-ethanediylbis(amino)]bis[3-[4-(4-methyl-1-piperazinyl)butyl]-2,4-imidazolidinedione]. In some embodiments, the azimilide hemi-hydrate comprises between 0.00001% and 0.3% by weight of 1,1'-[1,2-ethanediylbis(amino)]bis[3-[4-(4-methyl-1-piperazinyl)butyl]-2,4-imidazolidinedione]. In some embodiments, the azimilide hemi-hydrate comprises between 0.00001% and 0.2% by weight of 1,1'-[1,2-Ethanediylbis(amino)]bis[3-[4-(4-methyl-1-piperazinyl)butyl]-2,4-imidazolidinedione]. In some embodiments, the azimilide hemi-hydrate comprises between 0.00001% and 0.1% by weight of 1,1'-[1,2-ethanediylbis(amino)]bis[3-[4-(4-methyl-1-piperazinyl)butyl]-2,4-imidazolidinedione].

Alternatively, or in addition in some embodiments, the azimilide hemi-hydrate comprises between 0.00001% and 0.5% by weight of 1-[(2-furanylmethylene)amino]-3-[4-(4-methyl-1-piperazinyl)butyl]-2,4-imidazolidinedione dihydrochloride. In some embodiments, the azimilide hemi-hydrate comprises between 0.00001% and 0.4% by weight of 1-[(2-furanylmethylene)amino]-3-[4-(4-methyl-1-piperazinyl)butyl]-2,4-imidazolidinedione dihydrochloride. In some embodiments, the azimilide hemi-hydrate comprises between 0.00001% and 0.3% by weight of 1-[(2-furanylmethylene)amino]-3-[4-(4-methyl-1-piperazinyl)butyl]-2,4-imidazolidinedione dihydrochloride. In some embodiments, the azimilide hemi-hydrate comprises between 0.00001% and 0.2% by weight of 1-[(2-furanylmethylene)amino]-3-[4-(4-methyl-1-piperazinyl)butyl]-2,4-imidazolidinedione dihydrochloride. In some embodiments, the azimilide hemi-hydrate comprises between 0.00001% and 0.1% by weight of 1-[(2-furanylmethylene)amino]-3-[4-(4-methyl-1-piperazinyl)butyl]-2,4-imidazolidinedione dihydrochloride.

Alternatively, or in addition in some embodiments, the azimilide hemi-hydrate comprises between 0.00001% and 0.5% by weight of (Z)-1-[[[5-(4-Chlorophenyl)-2-furanyl]methylene]amino]-3-[4-(4-methyl-1-piperazinyl)butyl]-2,4-imidazolidinedione. In some embodiments, the azimilide hemi-hydrate comprises between 0.00001% and 0.4% by weight of (Z)-1-[[[5-(4-Chlorophenyl)-2-furanyl]methylene]amino]-3-[4-(4-methyl-1-piperazinyl)butyl]-2,4-imidazolidinedione. In some embodiments, the azimilide hemi-hydrate comprises between 0.00001% and 0.3% by weight of (Z)-1-[[[5-(4-Chlorophenyl)-2-furanyl]methylene]amino]-3-[4-(4-methyl-1-piperazinyl)butyl]-2,4-imidazolidinedione. In some embodiments, the azimilide hemi-hydrate comprises between 0.00001% and 0.2% by weight of (Z)-1-[[[5-(4-Chlorophenyl)-2-furanyl]methylene]amino]-3-[4-(4-methyl-1-piperazinyl)butyl]-2,4-imidazolidinedione. In some embodiments, the azimilide hemi-hydrate comprises between 0.00001% and 0.1% by weight of (Z)-1-[[[5-(4-Chlorophenyl)-2-furanyl]methylene]amino]-3-[4-(4-methyl-1-piperazinyl)butyl]-2,4-imidazolidinedione.

Alternatively, or in addition in some embodiments, the azimilide hemi-hydrate comprises between 0.00001% and 0.5% by weight of 1-[[[5-(4-Chlorophenyl)-2-furanyl]methylene]amino]-3-[4-(1-piperazinyl)butyl]-2,4-imidazolidinedione dihydrochloride. In some embodiments, the azimilide hemi-hydrate comprises between 0.00001% and 0.4% by weight of 1-[[[5-(4-Chlorophenyl)-2-furanyl]methylene]amino]-3-[4-(1-piperazinyl)butyl]-2,4-imidazolidinedione dihydrochloride. In some embodiments, the azimilide hemi-hydrate comprises between 0.00001% and 0.3% by weight of 1-[[[5-(4-Chlorophenyl)-2-furanyl]methylene]amino]-3-[4-(1-piperazinyl)butyl]-2,4-imidazolidinedione dihydrochloride. In some embodiments, the azimilide hemi-hydrate comprises between 0.00001% and 0.2% by weight of 1-[[[5-(4-Chlorophenyl)-2-furanyl]methylene]amino]-3-[4-(1-piperazinyl)butyl]-2,4-imidazolidinedione dihydrochloride. In some embodiments, the azimilide hemi-hydrate comprises between 0.00001% and 0.1% by weight of 1-[[[5-(4-Chlorophenyl)-2-furanyl]methylene]amino]-3-[4-(1-piperazinyl)butyl]-2,4-imidazolidinedione dihydrochloride.

Alternatively, or in addition in some embodiments, the azimilide hemi-hydrate comprises between 0.00001% and 0.5% by weight of 1-[[[5-[4-Chloro-2-(4-chlorophenyl)phenyl]-2-furanyl]methylene]amino]-3-[4-(4-methyl-1-piperazinyl)butyl]-2,4-imidazolidinedione dihydrochloride. In some embodiments, the azimilide hemi-hydrate comprises between 0.00001% and 0.4% by weight of 1-[[[5-[4-Chloro-2-(4-chlorophenyl)phenyl]-2-furanyl]methylene]amino]-3-[4-(4-methyl-1-piperazinyl)butyl]-2,4-imidazolidinedione dihydrochloride. In some embodiments, the azimilide hemi-hydrate comprises between 0.00001% and 0.3% by weight of 1-[[[5-[4-Chloro-2-(4-chlorophenyl)phenyl]-2-furanyl]methylene]amino]-3-[4-(4-methyl-1-piperazinyl)butyl]-2,4-imidazolidinedione dihydrochloride. In some embodiments, the azimilide hemi-hydrate comprises between 0.00001% and 0.2% by weight of 1-[[[5-[4-Chloro-2-(4-chlorophenyl)phenyl]-2-furanyl]methylene]amino]-3-[4-(4-methyl-1-piperazinyl)butyl]-2,4-imidazolidinedione dihydrochloride. In some embodiments, the azimilide hemi-hydrate comprises between 0.00001% and 0.1% by weight of 1-[[[5-[4-Chloro-2-(4-chlorophenyl)phenyl]-2-furanyl]methylene]amino]-3-[4-(4-methyl-1-piperazinyl)butyl]-2,4-imidazolidinedione dihydrochloride.

Alternatively, or in addition in some embodiments, the azimilide hemi-hydrate comprises between 0.00001% and 0.5% by weight of 1-[[[5-(4-chlorophenyl)-2-furanyl]methylene]amino]-2,4-imidazolidinedione. In some embodiments, the azimilide hemi-hydrate comprises between 0.00001% and 0.4% by weight of 1-[[[5-(4-chlorophenyl)-2-furanyl]methylene]amino]-2,4-imidazolidinedione. In some embodiments, the azimilide hemi-hydrate comprises between 0.00001% and 0.3% by weight of 1-[[[5-(4-chlorophenyl)-2-furanyl]methylene]amino]-2,4-imidazolidinedione. In some embodiments, the azimilide hemi-hydrate comprises between 0.00001% and 0.2% by weight of 1-[[[5-(4-chlorophenyl)-2-furanyl]methylene]amino]-2,4-imidazolidinedione. In some embodiments, the azimilide hemi-hydrate comprises between 0.00001% and 0.1% by weight of 1-[[[5-(4-chlorophenyl)-2-furanyl]methylene]amino]-2,4-imidazolidinedione.

Alternatively, or in addition in some embodiments, the azimilide hemi-hydrate comprises between 0.00001% and 0.5% by weight of 1-[(2-furanylmethylene)amino]-3-[4-(4-methyl-1-piperazinyl)butyl]-2,4-imidazolidinedione dihydrochloride. In some embodiments, the azimilide hemi-hydrate comprises between 0.00001% and 0.4% by weight of 1-[(2-furanylmethylene)amino]-3-[4-(4-methyl-1-piperazinyl)butyl]-2,4-imidazolidinedione dihydrochloride. In some embodiments, the azimilide hemi-hydrate comprises between 0.00001% and 0.3% by weight of 1-[(2-furanylmethylene)amino]-3-[4-(4-methyl-1-piperazinyl)butyl]-2,4-imidazolidinedione dihydrochloride. In some embodiments, the azimilide hemi-hydrate comprises between 0.00001% and 0.2% by weight of 1-[(2-furanylmethylene)amino]-3-[4-(4-methyl-1-piperazinyl)butyl]-2,4-imidazolidinedione dihydrochloride. In some embodiments, the azimilide hemi-hydrate comprises between 0.00001% and 0.1% by weight of 1-[(2-furanylmethylene)amino]-3-[4-(4-methyl-1-piperazinyl)butyl]-2,4-imidazolidinedione dihydrochloride.

Alternatively, or in addition in some embodiments, the azimilide hemi-hydrate comprises between 0.00001% and 0.5% by weight of 4-methyl-1-piperazinecarboxylic acid, 4-[1-[[[5-(4-chlorophenyl)-2-furanyl]methylene]amino]-2,4-dioxo-3-imidazolidinyl]butyl ester. In some embodiments, the azimilide hemi-hydrate comprises between 0.00001% and 0.4% by weight of 4-methyl-1-piperazinecarboxylic acid, 4-[1-[[[5-(4-chlorophenyl)-2-furanyl]methylene]amino]-2,4-dioxo-3-imidazolidinyl]butyl ester. In some embodiments, the azimilide hemi-hydrate comprises between 0.00001% and 0.3% by weight of 4-methyl-1-piperazinecarboxylic acid, 4-[1-[[[5-(4-chlorophenyl)-2-furanyl]methylene]amino]-2,4-dioxo-3-imidazolidinyl]butyl ester. In some embodiments, the azimilide hemi-hydrate comprises between 0.00001% and 0.2% by weight of 4-methyl-1-piperazinecarboxylic acid, 4-[1-[[[5-(4-chlorophenyl)-2-furanyl]methylene]amino]-2,4-dioxo-3-imidazolidinyl]butyl ester. In some embodiments, the azimilide hemi-hydrate comprises between 0.00001% and 0.1% by weight of 4-methyl-1-piperazinecarboxylic acid, 4-[1-[[[5-(4-chlorophenyl)-2-furanyl]methylene]amino]-2,4-dioxo-3-imidazolidinyl]butyl ester.

Alternatively, or in addition in some embodiments, the azimilide hemi-hydrate comprises between 0.00001% and 0.5% by weight of 1-[[[5-(4-Chlorophenyl)-2-furanyl]methylene]amino]-3-(4-hydroxybutyl)-2,4-imidazolidinedione. In some embodiments, the azimilide hemi-hydrate comprises between 0.00001% and 0.4% by weight of 1-[[[5-(4-Chlorophenyl)-2-furanyl]methylene]amino]-3-(4-hydroxybutyl)-2,4-imidazolidinedione. In some embodiments, the azimilide hemi-hydrate comprises between 0.00001% and 0.3% by weight of 1-[[[5-(4-Chlorophenyl)-2-furanyl]methylene] amino]-3-(4-hydroxybutyl)-2,4-imidazolidinedione. In some embodiments, the azimilide hemi-hydrate comprises between 0.00001% and 0.2% by weight of 1-[[[5-(4-Chlorophenyl)-2-furanyl]methylene]amino]-3-(4-hydroxybutyl)-2,4-imidazolidinedione. In some embodiments, the azimilide hemi-hydrate comprises between 0.00001% and 0.1% by weight of 1-[[[5-(4-Chlorophenyl)-2-furanyl]methylene] amino]-3-(4-hydroxybutyl)-2,4-imidazolidinedione.

In some embodiments, the azimilide isopropanol solvate comprises between 0.00001% and 0.0025% by weight of 1-[[[5-(4-Chlorophenyl)-2-furanyl]methylene]amino]-3-[4-(chloro)butyl]-2,4-imidazolidinedione. In some embodiments, the azimilide isopropanol solvate comprises between 0.00001% and 0.002% by weight of 1-[[[5-(4-Chlorophenyl)-2-furanyl]methylene]amino]-3-[4-(chloro)butyl]-2,4-imidazolidinedione. In some embodiments, the azimilide isopropanol solvate comprises between 0.0001% and 0.002% by weight of 1-[[[5-(4-Chlorophenyl)-2-furanyl]methylene] amino]-3-[4-(chloro)butyl]-2,4-imidazolidinedione.

Alternatively, or in addition in some embodiments, the azimilide isopropanol solvate comprises between 0.00001% and 0.2% by weight of 5-(4-chlorophenyl)-2-furancarboxaldehyde. In some embodiments, the azimilide isopropanol solvate comprises between 0.0001% and 0.1% by weight of 5-(4-chlorophenyl)-2-furancarboxaldehyde. In some embodiments, the azimilide isopropanol solvate comprises between 0.001% and 0.002% by weight of 5-(4-chlorophenyl)-2-furancarboxaldehyde.

Alternatively, or in addition in some embodiments, the azimilide isopropanol solvate comprises between 0.00001% and 0.2% by weight of 1-Amino-3-[4-(4-methyl-1-piperazinyl)butyl]-2,4-imidazolidinedione dihydrochloride. In some embodiments, the azimilide isopropanol solvate comprises between 0.0001% and 0.1% by weight of 1-Amino-3-[4-(4-methyl-1-piperazinyl)butyl]-2,4-imidazolidinedione dihydrochloride. In some embodiments, the azimilide isopropanol solvate comprises between 0.001% and 0.2% by weight of 1-Amino-3-[4-(4-methyl-1-piperazinyl)butyl]-2,4-imidazolidinedione dihydrochloride.

Alternatively, or in addition in some embodiments, the azimilide isopropanol solvate comprises between 0.00001% and 0.3% by weight of 3,3'-[1,4-Piperazinediylbis(butylene)] bis[1-[[[5-(4-chlorophenyl)-2-furanyl]methylene]amino]-2,4-imidazolidinedione]. In some embodiments, the azimilide isopropanol solvate comprises between 0.00001% and 0.2% by weight of 3,3'-[1,4-Piperazinediylbis(butylene)]bis[1-[[[5-(4-chlorophenyl)-2-furanyl]methylene]amino]-2,4-imidazolidinedione]. In some embodiments, the azimilide isopropanol solvate comprises between 0.00001% and 0.1% by weight of 3,3'-[1,4-Piperazinediylbis(butylene)]bis[1-[[[5-(4-chlorophenyl)-2-furanyl]methylene]amino]-2,4-imidazolidine-dione]. In some embodiments, the azimilide isopropanol solvate comprises between 0.001% and 0.3% by weight of 3,3'-[1,4-Piperazinediylbis(butylene)]bis[1-[[[5-(4-chlorophenyl)-2-furanyl]methylene]amino]-2,4-imidazolidinedione].

Alternatively, or in addition in some embodiments, the azimilide isopropanol solvate comprises between 0.00001% and 0.5% by weight of 1,4-bis[4-[1-[[[5-(4-Chlorophenyl)-2-furanyl]methylene]amino]-2,4-dioxo-3-imidazolidinyl]butyl]-1-methylpiperazinium chloride. In some embodiments, the azimilide isopropanol solvate comprises between 0.00001% and 0.4% by weight of 1,4-bis[4-[1-[[[5-(4-Chlorophenyl)-2-furanyl]methylene]amino]-2,4-dioxo-3-imidazolidinyl]butyl]-1-methylpiperazinium chloride. In some embodiments, the azimilide isopropanol solvate comprises between 0.00001% and 0.3% by weight of 1,4-bis[4-[1-[[[5-(4-Chlorophenyl)-2-furanyl]methylene]amino]-2,4-dioxo-3-imidazolidinyl]butyl]-1-methylpiperazinium chloride. In some embodiments, the azimilide isopropanol solvate comprises between 0.00001% and 0.2% by weight of 1,4-bis[4-[1-[[[5-(4-Chlorophenyl)-2-furanyl]methylene]amino]-2,4-dioxo-3-imidazolidinyl]butyl]-1-methylpiperazinium chloride. In some embodiments, the azimilide isopropanol solvate comprises between 0.00001% and 0.1% by weight of 1,4-bis[4-[1-[[[5-(4-Chlorophenyl)-2-furanyl]methylene]amino]-2,4-dioxo-3-imidazolidinyl]butyl]-1-methylpiperazinium chloride.

Alternatively, or in addition in some embodiments, the azimilide isopropanol solvate comprises between 0.00001% and 0.5% by weight of 1,1'-[1,2-ethanediylbis(amino)]bis[3-[4-(4-methyl-1-piperazinyl)butyl]-2,4-imidazolidinedione]. In some embodiments, the azimilide isopropanol solvate comprises between 0.00001% and 0.4% by weight of 1,1'-[1,2-ethanediylbis(amino)]bis[3-[4-(4-methyl-1-piperazinyl)butyl]-2,4-imidazolidinedione]. In some embodiments, the azimilide isopropanol solvate comprises between 0.00001% and 0.3% by weight of 1,1'-[1,2-ethanediylbis(amino)]bis[3-[4-(4-methyl-1-piperazinyl)butyl]-2,4-imidazolidinedione]. In some embodiments, the azimilide isopropanol solvate comprises between 0.00001% and 0.2% by weight of 1,1'-[1,2-Ethanediylbis(amino)]bis[3-[4-(4-methyl-1-piperazinyl)butyl]-2,4-imidazolidinedione]. In some embodiments, the azimilide isopropanol solvate comprises between 0.00001% and 0.1% by weight of 1,1'-[1,2-ethanediylbis(amino)]bis[3-[4-(4-methyl-1-piperazinyl)butyl]-2,4-imidazolidinedione].

Alternatively, or in addition in some embodiments, the azimilide isopropanol solvate comprises between 0.00001% and 0.5% by weight of 1-[(2-furanylmethylene)amino]-3-[4-(4-methyl-1-piperazinyl)butyl]-2,4-imidazolidinedione dihydrochloride. In some embodiments, the azimilide isopropanol solvate comprises between 0.00001% and 0.4% by weight of 1-[(2-furanylmethylene)amino]-3-[4-(4-methyl-1-piperazinyl)butyl]-2,4-imidazolidinedione dihydrochloride. In some embodiments, the azimilide isopropanol solvate comprises between 0.00001% and 0.3% by weight of 1-[(2-furanylmethylene)amino]-3-[4-(4-methyl-1-piperazinyl)butyl]-2,4-imidazolidinedione dihydrochloride. In some embodiments, the azimilide isopropanol solvate comprises between 0.00001% and 0.2% by weight of 1-[(2-furanylmethylene)amino]-3-[4-(4-methyl-1-piperazinyl)butyl]-2,4-imidazolidinedione dihydrochloride. In some embodiments, the azimilide isopropanol solvate comprises between 0.00001% and 0.1% by weight of 1-[(2-furanylmethylene)amino]-3-[4-(4-methyl-1-piperazinyl)butyl]-2,4-imidazolidinedione dihydrochloride.

Alternatively, or in addition in some embodiments, the azimilide isopropanol solvate comprises between 0.00001% and 0.5% by weight of (Z)-1-[[[5-(4-Chlorophenyl)-2-furanyl]methylene]amino]-3-[4-(4-methyl-1-piperazinyl)butyl]-2,4-imidazolidinedione. In some embodiments, the azimilide isopropanol solvate comprises between 0.00001% and 0.4% by weight of (Z)-1-[[[5-(4-Chlorophenyl)-2-furanyl]methylene]amino]-3-[4-(4-methyl-1-piperazinyl)butyl]-2,4-imidazolidinedione. In some embodiments, the azimilide isopropanol solvate comprises between 0.00001% and 0.3% by weight of (Z)-1-[[[5-(4-Chlorophenyl)-2-furanyl]methylene] amino]-3-[4-(4-methyl-1-piperazinyl)butyl]-2,4-imidazolidinedione. In some embodiments, the azimilide isopropanol solvate comprises between 0.00001% and 0.2% by weight of (Z)-1-[[[5-(4-Chlorophenyl)-2-furanyl]methylene]amino]-3-[4-(4-methyl-1-piperazinyl)butyl]-2,4-imidazolidinedione. In some embodiments, the azimilide isopropanol solvate comprises between 0.00001% and 0.1% by weight of (Z)-1-[[[5-(4-Chlorophenyl)-2-furanyl]methylene]amino]-3-[4-(4-methyl-1-piperazinyl)butyl]-2,4-imidazolidinedione.

Alternatively, or in addition in some embodiments, the azimilide isopropanol solvate comprises between 0.00001% and 0.5% by weight of 1-[[[5-(4-Chlorophenyl)-2-furanyl]methylene]amino]-3-[4-(1-piperazinyl)butyl]-2,4-imidazolidinedione dihydrochloride. In some embodiments, the azimilide isopropanol solvate comprises between 0.00001% and 0.4% by weight of 1-[[[5-(4-Chlorophenyl)-2-furanyl]methylene]amino]-3-[4-(1-piperazinyl)butyl]-2,4-imidazolidinedione dihydrochloride. In some embodiments, the azimilide isopropanol solvate comprises between 0.00001% and 0.3% by weight of 1-[[[5-(4-Chlorophenyl)-2-furanyl]methylene]amino]-3-[4-(1-piperazinyl)butyl]-2,4-imidazolidinedione dihydrochloride. In some embodiments, the azimilide isopropanol solvate comprises between 0.00001% and 0.2% by weight of 1-[[[5-(4-Chlorophenyl)-2-furanyl]methylene]amino]-3-[4-(1-piperazinyl)butyl]-2,4-imidazolidinedione dihydrochloride. In some embodiments, the azimilide isopropanol solvate comprises between 0.00001% and 0.1% by weight of 1-[[[5-(4-Chlorophenyl)-2-furanyl]methylene]amino]-3-[4-(1-piperazinyl)butyl]-2,4-imidazolidinedione dihydrochloride.

Alternatively, or in addition in some embodiments, the azimilide isopropanol solvate comprises between 0.00001% and 0.5% by weight of 1-[[[5-[4-Chloro-2-(4-chlorophenyl)phenyl]-2-furanyl]methylene]amino]-3-[4-(4-methyl-1-piperazinyl)butyl]-2,4-imidazolidinedione dihydrochloride. In some embodiments, the azimilide isopropanol solvate comprises between 0.00001% and 0.4% by weight of 1-[[[5-[4-Chloro-2-(4-chlorophenyl)phenyl]-2-furanyl]methylene]amino]-3-[4-(4-methyl-1-piperazinyl)butyl]-2,4-imidazolidinedione dihydrochloride. In some embodiments, the azimilide isopropanol solvate comprises between 0.00001% and 0.3% by weight of 1-[[[5-[4-Chloro-2-(4-chlorophenyl)phenyl]-2-furanyl]methylene]amino]-3-[4-(4-methyl-1-piperazinyl)butyl]-2,4-imidazolidinedione dihydrochloride. In some embodiments, the azimilide isopropanol solvate comprises between 0.00001% and 0.2% by weight of 1-[[[5-[4-Chloro-2-(4-chlorophenyl)phenyl]-2-furanyl]methylene]amino]-3-[4-(4-methyl-1-piperazinyl)butyl]-2,4-imidazolidinedione dihydrochloride. In some embodiments, the azimilide isopropanol solvate comprises between 0.00001% and 0.1% by weight of 1-[[[5-[4-Chloro-2-(4-chlorophenyl)phenyl]-2-furanyl]methylene]amino]-3-[4-(4-methyl-1-piperazinyl)butyl]-2,4-imidazolidinedione dihydrochloride.

Alternatively, or in addition in some embodiments, the azimilide isopropanol solvate comprises between 0.00001% and 0.5% by weight of 1-[[[5-(4-chlorophenyl)-2-furanyl]methylene]amino]-2,4-imidazolidinedione. In some embodiments, the azimilide isopropanol solvate comprises between 0.00001% and 0.4% by weight of 1-[[[5-(4-chlorophenyl)-2-furanyl]methylene]amino]-2,4-imidazolidinedione. In some embodiments, the azimilide isopropanol solvate comprises between 0.00001% and 0.3% by weight of 1-[[[5-(4-chlorophenyl)-2-furanyl]methylene]amino]-2,4-imidazolidinedione. In some embodiments, the azimilide isopropanol solvate comprises between 0.00001% and 0.2% by weight of 1-[[[5-(4-chlorophenyl)-2-furanyl]methylene]amino]-2,4-imidazolidinedione. In some embodiments, the azimilide isopropanol solvate comprises between 0.00001% and 0.1% by weight of 1-[[[5-(4-chlorophenyl)-2-furanyl]methylene]amino]-2,4-imidazolidinedione.

Alternatively, or in addition in some embodiments, the azimilide isopropanol solvate comprises between 0.00001% and 0.5% by weight of 1-[(2-furanylmethylene)amino]-3-[4-(4-methyl-1-piperazinyl)butyl]-2,4-imidazolidinedione dihydrochloride. In some embodiments, the azimilide isopropanol solvate comprises between 0.00001% and 0.4% by weight of 1-[(2-furanylmethylene)amino]-3-[4-(4-methyl-1-piperazinyl)butyl]-2,4-imidazolidinedione dihydrochloride. In some embodiments, the azimilide isopropanol solvate comprises between 0.00001% and 0.3% by weight of 1-[(2-furanylmethylene)amino]-3-[4-(4-methyl-1-piperazinyl)butyl]-2,4-imidazolidinedione dihydrochloride. In some embodiments, the azimilide isopropanol solvate comprises between 0.00001% and 0.2% by weight of 1-[(2-furanylmethylene)amino]-3-[4-(4-methyl-1-piperazinyl)butyl]-2,4-imidazolidinedione dihydrochloride. In some embodiments, the azimilide isopropanol solvate comprises between 0.00001% and 0.1% by weight of 1-[(2-furanylmethylene)amino]-3-[4-(4-methyl-1-piperazinyl)butyl]-2,4-imidazolidinedione dihydrochloride.

Alternatively, or in addition in some embodiments, the azimilide isopropanol solvate comprises between 0.00001% and 0.5% by weight of 4-methyl-1-piperazinecarboxylic acid, 4-[1-[[[5-(4-chlorophenyl)-2-furanyl]methylene]amino]-2,4-dioxo-3-imidazolidinyl]butyl ester. In some embodiments, the azimilide isopropanol solvate comprises between 0.00001% and 0.4% by weight of 4-methyl-1-piperazinecarboxylic acid, 4-[1-[[[5-(4-chlorophenyl)-2-furanyl]methylene]amino]-2,4-dioxo-3-imidazolidinyl]butyl ester. In some embodiments, the azimilide isopropanol solvate comprises between 0.00001% and 0.3% by weight of 4-methyl-1-piperazinecarboxylic acid, 4-[1-[[[5-(4-chlorophenyl)-2-furanyl]methylene]amino]-2,4-dioxo-3-imidazolidinyl]butyl ester. In some embodiments, the azimilide isopropanol solvate comprises between 0.00001% and 0.2% by weight of 4-methyl-1-piperazinecarboxylic acid, 4-[1-[[[5-(4-chlorophenyl)-2-furanyl]methylene]amino]-2,4-dioxo-3-imidazolidinyl]butyl ester. In some embodiments, the azimilide isopropanol solvate comprises between 0.00001% and 0.1% by weight of 4-methyl-1-piperazinecarboxylic acid, 4-[1-[[[5-(4-chlorophenyl)-2-furanyl]methylene]amino]-2,4-dioxo-3-imidazolidinyl]butyl ester.

Alternatively, or in addition in some embodiments, the azimilide isopropanol solvate comprises between 0.00001% and 0.5% by weight of 1-[[[5-(4-Chlorophenyl)-2-furanyl]methylene]amino]-3-(4-hydroxybutyl)-2,4-imidazolidinedione. In some embodiments, the azimilide isopropanol solvate comprises between 0.00001% and 0.4% by weight of 1-[[[5-(4-Chlorophenyl)-2-furanyl]methylene]amino]-3-(4-hydroxybutyl)-2,4-imidazolidinedione. In some embodiments, the azimilide isopropanol solvate comprises between 0.00001% and 0.3% by weight of 1-[[[5-(4-Chlorophenyl)-2-furanyl]methylene]amino]-3-(4-hydroxybutyl)-2,4-imidazolidinedione. In some embodiments, the azimilide isopropanol solvate comprises between 0.00001% and 0.2% by weight of 1-[[[5-(4-Chlorophenyl)-2-furanyl]methylene]amino]-3-(4-hydroxybutyl)-2,4-imidazolidinedione. In some embodiments, the azimilide isopropanol solvate comprises between 0.00001% and 0.1% by weight of 1-[[[5-(4-Chlorophenyl)-2-furanyl]methylene]amino]-3-(4-hydroxybutyl)-2,4-imidazolidinedione.

In some embodiments, the azimilide anhydrate comprises between 0.00001% and 0.0025% by weight of 1-[[[5-(4-Chlorophenyl)-2-furanyl]methylene]amino]-3-[4-(chloro)butyl]-2,4-imidazolidinedione. In some embodiments, the azimilide anhydrate comprises between 0.00001% and 0.002% by weight of 1-[[[5-(4-Chlorophenyl)-2-furanyl]methylene]amino]-3-[4-(chloro)butyl]-2,4-imidazolidinedione. In some embodiments, the azimilide anhydrate comprises between 0.0001% and 0.002% by weight of 1-[[[5-(4-Chlorophenyl)-2-furanyl]methylene]amino]-3-[4-(chloro)butyl]-2,4-imidazolidinedione.

Alternatively, or in addition in some embodiments, the azimilide anhydrate comprises between 0.00001% and 0.2% by weight of 5-(4-chlorophenyl)-2-furancarboxaldehyde. In some embodiments, the azimilide anhydrate comprises between 0.0001% and 0.1% by weight of 5-(4-chlorophenyl)-2-furancarboxaldehyde. In some embodiments, the azimilide anhydrate comprises between 0.001% and 0.002% by weight of 5-(4-chlorophenyl)-2-furancarboxaldehyde.

Alternatively, or in addition in some embodiments, the azimilide anhydrate comprises between 0.00001% and 0.2% by weight of 1-Amino-3-[4-(4-methyl-1-piperazinyl)butyl]-2,4-imidazolidinedione dihydrochloride. In some embodiments, the azimilide anhydrate comprises between 0.0001% and 0.1% by weight of 1-Amino-3-[4-(4-methyl-1-piperazinyl)butyl]-2,4-imidazolidinedione dihydrochloride. In some embodiments, the azimilide anhydrate comprises between 0.001% and 0.2% by weight of 1-Amino-3-[4-(4-methyl-1-piperazinyl)butyl]-2,4-imidazolidinedione dihydrochloride.

Alternatively, or in addition in some embodiments, the azimilide anhydrate comprises between 0.00001% and 0.3% by weight of 3,3'-[1,4-Piperazinediylbis(butylene)]bis[1-[[[5-(4-chlorophenyl)-2-furanyl]methylene]amino]-2,4-imidazolidinedione]. In some embodiments, the azimilide anhydrate comprises between 0.00001% and 0.2% by weight of 3,3'-[1,4-Piperazinediylbis(butylene)]bis[1-[[[5-(4-chlorophenyl)-2-furanyl]methylene]amino]-2,4-imidazolidinedione]. In some embodiments, the azimilide anhydrate comprises between 0.00001% and 0.1% by weight of 3,3'-[1,4-Piperazinediylbis(butylene)]bis[1-[[[5-(4-chlorophenyl)-2-furanyl]methylene]amino]-2,4-imidazolidine-dione]. In some embodiments, the azimilide anhydrate comprises between 0.001% and 0.3% by weight of 3,3'-[1,4-Piperazinediylbis(butylene)]bis[1-[[[5-(4-chlorophenyl)-2-furanyl]methylene]amino]-2,4-imidazolidinedione].

Alternatively, or in addition in some embodiments, the azimilide anhydrate comprises between 0.00001% and 0.5% by weight of 1,4-bis[4-[1-[[[5-(4-Chlorophenyl)-2-furanyl]methylene]amino]-2,4-dioxo-3-imidazolidinyl]butyl]-1-methylpiperazinium chloride. In some embodiments, the azimilide anhydrate comprises between 0.00001% and 0.4% by weight of 1,4-bis[4-[1-[[[5-(4-Chlorophenyl)-2-furanyl]methylene]amino]-2,4-dioxo-3-imidazolidinyl]butyl]-1-methylpiperazinium chloride. In some embodiments, the azimilide anhydrate comprises between 0.00001% and 0.3% by weight of 1,4-bis[4-[1-[[[5-(4-Chlorophenyl)-2-furanyl]methylene]amino]-2,4-dioxo-3-imidazolidinyl]butyl]-1-methylpiperazinium chloride. In some embodiments, the azimilide anhydrate comprises between 0.00001% and 0.2% by weight of 1,4-bis[4-[1-[[[5-(4-Chlorophenyl)-2-furanyl]methylene]amino]-2,4-dioxo-3-imidazolidinyl]butyl]-1-methylpiperazinium chloride. In some embodiments, the azimilide anhydrate comprises between 0.00001% and 0.1% by weight of 1,4-bis[4-[1-[[[5-(4-Chlorophenyl)-2-furanyl]methylene]amino]-2,4-dioxo-3-imidazolidinyl]butyl]-1-methylpiperazinium chloride.

Alternatively, or in addition in some embodiments, the azimilide anhydrate comprises between 0.00001% and 0.5% by weight of 1,1'-[1,2-ethanediylbis(amino)]bis[3-[4-(4-methyl-1-piperazinyl)butyl]-2,4-imidazolidinedione]. In some embodiments, the azimilide anhydrate comprises between 0.00001% and 0.4% by weight of 1,1'-[1,2-ethanediylbis(amino)]bis[3-[4-(4-methyl-1-piperazinyl)butyl]-2,4-imidazolidinedione]. In some embodiments, the azimilide anhydrate comprises between 0.00001% and 0.3% by weight of 1,1'-[1,2-ethanediylbis(amino)]bis[3-[4-(4-methyl-1-piperazinyl)butyl]-2,4-imidazolidinedione]. In some embodiments, the azimilide anhydrate comprises between 0.00001% and 0.2% by weight of 1,1'-[1,2-Ethanediylbis(amino)]bis[3-[4-(4-methyl-1-piperazinyl)butyl]-2,4-imidazolidinedione]. In some embodiments, the azimilide anhydrate comprises between 0.00001% and 0.1% by weight of 1,1'-[1,2-ethanediylbis(amino)]bis[3-[4-(4-methyl-1-piperazinyl)butyl]-2,4-imidazolidinedione].

Alternatively, or in addition in some embodiments, the azimilide anhydrate comprises between 0.00001% and 0.5% by weight of 1-[(2-furanylmethylene)amino]-3-[4-(4-methyl-1-piperazinyl)butyl]-2,4-imidazolidinedione dihydrochloride. In some embodiments, the azimilide anhydrate comprises between 0.00001% and 0.4% by weight of 1-[(2-furanylmethylene)amino]-3-[4-(4-methyl-1-piperazinyl)butyl]-2,4-imidazolidinedione dihydrochloride. In some embodiments, the azimilide anhydrate comprises between 0.00001% and 0.3% by weight of 1-[(2-furanylmethylene)amino]-3-[4-(4-methyl-1-piperazinyl)butyl]-2,4-imidazolidinedione dihydrochloride. In some embodiments, the azimilide anhydrate comprises between 0.00001% and 0.2% by weight of 1-[(2-furanylmethylene)amino]-3-[4-(4-methyl-1-piperazinyl)butyl]-2,4-imidazolidinedione dihydrochloride. In some embodiments, the azimilide anhydrate comprises between 0.00001% and 0.1% by weight of 1-[(2-furanylmethylene)amino]-3-[4-(4-methyl-1-piperazinyl)butyl]-2,4-imidazolidinedione dihydrochloride.

Alternatively, or in addition in some embodiments, the azimilide anhydrate comprises between 0.00001% and 0.5% by weight of (Z)-1-[[[5-(4-Chlorophenyl)-2-furanyl]methylene]amino]-3-[4-(4-methyl-1-piperazinyl)butyl]-2,4-imidazolidinedione. In some embodiments, the azimilide anhydrate comprises between 0.00001% and 0.4% by weight of (Z)-1-[[[5-(4-Chlorophenyl)-2-furanyl]methylene]amino]-3-[4-(4-methyl-1-piperazinyl)butyl]-2,4-imidazolidinedione. In some embodiments, the azimilide anhydrate comprises between 0.00001% and 0.3% by weight of (Z)-1-[[[5-(4-Chlorophenyl)-2-furanyl]methylene]amino]-3-[4-(4-methyl-1-piperazinyl)butyl]-2,4-imidazolidinedione. In some embodiments, the azimilide anhydrate comprises between 0.00001% and 0.2% by weight of (Z)-1-[[[5-(4-Chlorophenyl)-2-furanyl]methylene]amino]-3-[4-(4-methyl-1-piperazinyl)butyl]-2,4-imidazolidinedione. In some embodiments, the azimilide anhydrate comprises between 0.00001% and 0.1% by weight of (Z)-1-[[[5-(4-Chlorophenyl)-2-furanyl]methylene]amino]-3-[4-(4-methyl-1-piperazinyl)butyl]-2,4-imidazolidinedione.

Alternatively, or in addition in some embodiments, the azimilide anhydrate comprises between 0.00001% and 0.5% by weight of 1-[[[5-(4-Chlorophenyl)-2-furanyl]methylene]amino]-3-[4-(1-piperazinyl)butyl]-2,4-imidazolidinedione dihydrochloride. In some embodiments, the azimilide anhydrate comprises between 0.00001% and 0.4% by weight of 1-[[[5-(4-Chlorophenyl)-2-furanyl]methylene]amino]-3-[4-(1-piperazinyl)butyl]-2,4-imidazolidinedione dihydrochloride. In some embodiments, the azimilide anhydrate comprises between 0.00001% and 0.3% by weight of 1-[[[5-(4-Chlorophenyl)-2-furanyl]methylene]amino]-3-[4-(1-piperazinyl)butyl]-2,4-imidazolidinedione dihydrochloride. In some embodiments, the azimilide anhydrate comprises between 0.00001% and 0.2% by weight of 1-[[[5-(4-Chlorophenyl)-2-furanyl]methylene]amino]-3-[4-(1-piperazinyl)

butyl]-2,4-imidazolidinedione dihydrochloride. In some embodiments, the azimilide anhydrate comprises between 0.00001% and 0.1% by weight of 1-[[[5-(4-Chlorophenyl)-2-furanyl]methylene]amino]-3-[4-(1-piperazinyl)butyl]-2,4-imidazolidinedione dihydrochloride.

Alternatively, or in addition in some embodiments, the azimilide anhydrate comprises between 0.00001% and 0.5% by weight of 1-[[[5-[4-Chloro-2-(4-chlorophenyl)phenyl]-2-furanyl]methylene]amino]-3-[4-(4-methyl-1-piperazinyl)butyl]-2,4-imidazolidinedione dihydrochloride. In some embodiments, the azimilide anhydrate comprises between 0.00001% and 0.4% by weight of 1-[[[5-[4-Chloro-2-(4-chlorophenyl)phenyl]-2-furanyl]methylene]amino]-3-[4-(4-methyl-1-piperazinyl)butyl]-2,4-imidazolidinedione dihydrochloride. In some embodiments, the azimilide anhydrate comprises between 0.00001% and 0.3% by weight of 1-[[[5-[4-Chloro-2-(4-chlorophenyl)phenyl]-2-furanyl]methylene]amino]-3-[4-(4-methyl-1-piperazinyl)butyl]-2,4-imidazolidinedione dihydrochloride. In some embodiments, the azimilide anhydrate comprises between 0.00001% and 0.2% by weight of 1-[[[5-[4-Chloro-2-(4-chlorophenyl)phenyl]-2-furanyl]methylene]amino]-3-[4-(4-methyl-1-piperazinyl)butyl]-2,4-imidazolidinedione dihydrochloride. In some embodiments, the azimilide anhydrate comprises between 0.00001% and 0.1% by weight of 1-[[[5-[4-Chloro-2-(4-chlorophenyl)phenyl]-2-furanyl]methylene]amino]-3-[4-(4-methyl-1-piperazinyl)butyl]-2,4-imidazolidinedione dihydrochloride.

Alternatively, or in addition in some embodiments, the azimilide anhydrate comprises between 0.00001% and 0.5% by weight of 1-[[[5-(4-chlorophenyl)-2-furanyl]methylene]amino]-2,4-imidazolidinedione. In some embodiments, the azimilide anhydrate comprises between 0.00001% and 0.4% by weight of 1-[[[5-(4-chlorophenyl)-2-furanyl]methylene]amino]-2,4-imidazolidinedione. In some embodiments, the azimilide anhydrate comprises between 0.00001% and 0.3% by weight of 1-[[[5-(4-chlorophenyl)-2-furanyl]methylene]amino]-2,4-imidazolidinedione. In some embodiments, the azimilide anhydrate comprises between 0.00001% and 0.2% by weight of 1-[[[5-(4-chlorophenyl)-2-furanyl]methylene]amino]-2,4-imidazolidinedione. In some embodiments, the azimilide anhydrate comprises between 0.00001% and 0.1% by weight of 1-[[[5-(4-chlorophenyl)-2-furanyl]methylene]amino]-2,4-imidazolidinedione.

Alternatively, or in addition in some embodiments, the azimilide anhydrate comprises between 0.00001% and 0.5% by weight of 1-[(2-furanylmethylene)amino]-3-[4-(4-methyl-1-piperazinyl)butyl]-2,4-imidazolidinedione dihydrochloride. In some embodiments, the azimilide anhydrate comprises between 0.00001% and 0.4% by weight of 1-[(2-furanylmethylene)amino]-3-[4-(4-methyl-1-piperazinyl)butyl]-2,4-imidazolidinedione dihydrochloride. In some embodiments, the azimilide anhydrate comprises between 0.00001% and 0.3% by weight of 1-[(2-furanylmethylene)amino]-3-[4-(4-methyl-1-piperazinyl)butyl]-2,4-imidazolidinedione dihydrochloride. In some embodiments, the azimilide anhydrate comprises between 0.00001% and 0.2% by weight of 1-[(2-furanylmethylene)amino]-3-[4-(4-methyl-1-piperazinyl)butyl]-2,4-imidazolidinedione dihydrochloride. In some embodiments, the azimilide anhydrate comprises between 0.00001% and 0.1% by weight of 1-[(2-furanylmethylene)amino]-3-[4-(4-methyl-1-piperazinyl)butyl]-2,4-imidazolidinedione dihydrochloride.

Alternatively, or in addition in some embodiments, the azimilide anhydrate comprises between 0.00001% and 0.5% by weight of 4-methyl-1-piperazinecarboxylic acid, 4-[1-[[[5-(4-chlorophenyl)-2-furanyl]methylene]amino]-2,4-dioxo-3-imidazolidinyl]butyl ester. In some embodiments, the azimilide anhydrate comprises between 0.00001% and 0.4% by weight of 4-methyl-1-piperazinecarboxylic acid, 4-[1-[[[5-(4-chlorophenyl)-2-furanyl]methylene]amino]-2,4-dioxo-3-imidazolidinyl]butyl ester. In some embodiments, the azimilide anhydrate comprises between 0.00001% and 0.3% by weight of 4-methyl-1-piperazinecarboxylic acid, 4-[1-[[[5-(4-chlorophenyl)-2-furanyl]methylene]amino]-2,4-dioxo-3-imidazolidinyl]butyl ester. In some embodiments, the azimilide anhydrate comprises between 0.00001% and 0.2% by weight of 4-methyl-1-piperazinecarboxylic acid, 4-[1-[[[5-(4-chlorophenyl)-2-furanyl]methylene]amino]-2,4-dioxo-3-imidazolidinyl]butyl ester. In some embodiments, the azimilide anhydrate comprises between 0.00001% and 0.1% by weight of 4-methyl-1-piperazinecarboxylic acid, 4-[1-[[[5-(4-chlorophenyl)-2-furanyl]methylene]amino]-2,4-dioxo-3-imidazolidinyl]butyl ester.

Alternatively, or in addition in some embodiments, the azimilide anhydrate comprises between 0.00001% and 0.5% by weight of 1-[[[5-(4-Chlorophenyl)-2-furanyl]methylene]amino]-3-(4-hydroxybutyl)-2,4-imidazolidinedione. In some embodiments, the azimilide anhydrate comprises between 0.00001% and 0.4% by weight of 1-[[[5-(4-Chlorophenyl)-2-furanyl]methylene]amino]-3-(4-hydroxybutyl)-2,4-imidazolidinedione. In some embodiments, the azimilide anhydrate comprises between 0.00001% and 0.3% by weight of 1-[[[5-(4-Chlorophenyl)-2-furanyl]methylene]amino]-3-(4-hydroxybutyl)-2,4-imidazolidinedione. In some embodiments, the azimilide anhydrate comprises between 0.00001% and 0.2% by weight of 1-[[[5-(4-Chlorophenyl)-2-furanyl]methylene]amino]-3-(4-hydroxybutyl)-2,4-imidazolidinedione. In some embodiments, the azimilide anhydrate comprises between 0.00001% and 0.1% by weight of 1-[[[5-(4-Chlorophenyl)-2-furanyl]methylene]amino]-3-(4-hydroxybutyl)-2,4-imidazolidinedione.

The biological material should be extensively dialyzed to remove undesired small molecular weight molecules and/or lyophilized for more ready formulation into a desired vehicle, where appropriate. The active compounds may generally be formulated for parenteral administration, e.g., formulated for injection via the intravenous, intramuscular, subcutaneous, intralesional, and/or even intraperitoneal routes. The preparation of an aqueous compositions that contain an effective amount of a composition of the present invention as an active component and/or ingredient will be known to those of skill in the art in light of the present disclosure. Typically, such compositions can be prepared as injectables, either as liquid solutions and/or suspensions; solid forms suitable for using to prepare solutions and/or suspensions upon the addition of a liquid prior to injection can also be prepared; and/or the preparations can also be emulsified.

The pharmaceutical forms suitable for injectable use include sterile aqueous solutions and/or dispersions; formulations including sesame oil, peanut oil and/or aqueous propylene glycol; and/or sterile powders for the extemporaneous preparation of sterile injectable solutions and/or dispersions. In all cases the form must be sterile and/or must be fluid to the extent that easy syringability exists. It must be stable under the conditions of manufacture and/or storage and/or must be preserved against the contaminating action of microorganisms, such as bacteria and/or fungi.

Solutions of the compositions of the present invention as free bases and/or pharmacologically acceptable salts can be prepared in water suitably mixed with a surfactant, such as hydroxypropylcellulose. Dispersions can also be prepared in glycerol, liquid polyethylene glycols, and/or mixtures thereof and/or in oils. Under ordinary conditions of storage and/or use, these preparations contain a preservative to prevent the growth of microorganisms.

The compositions of the present invention can be formulated into a composition in a neutral and/or salt form. Pharmaceutically acceptable salts, include the acid addition salts (formed with the free amino groups of the protein) and/or which are formed with inorganic acids such as, for example, hydrochloric and/or phosphoric acids, and/or such organic acids as acetic, oxalic, tartaric, mandelic, and/or the like. Salts formed with the free carboxyl groups can also be derived from inorganic bases such as, for example, sodium, potassium, ammonium, calcium, and/or ferric hydroxides, and/or such organic bases as isopropylamine, trimethylamine, histidine, procaine and/or the like.

The carrier can also be a solvent and/or dispersion medium containing, for example, water, ethanol, polyol (for example, glycerol, propylene glycol, and/or liquid polyethylene glycol, and/or the like), suitable mixtures thereof, and/or vegetable oils. The proper fluidity can be maintained, for example, by the use of a coating, such as lecithin, by the maintenance of the required particle size in the case of dispersion and/or by the use of surfactants. The prevention of the action of microorganisms can be brought about by various antibacterial and/or antifungal agents, for example, parabens, chlorobutanol, phenol, sorbic acid, thimerosal, and/or the like. In many cases, it will be preferable to include isotonic agents, for example, sugars and/or sodium chloride. Prolonged absorption of the injectable compositions can be brought about by the use in the compositions of agents delaying absorption, for example, aluminum monostearate and/or gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the required other ingredients from those enumerated above. In the case of sterile powders for the preparation of sterile injectable solutions, the preferred methods of preparation are vacuum-drying and/or freeze-drying techniques which yield a powder of the active ingredient plus any additional desired ingredient from a previously sterile-filtered solution thereof. The preparation of more, and/or highly, concentrated solutions for direct injection is also contemplated, where the use of DMSO as solvent is envisioned to result in extremely rapid penetration, delivering high concentrations of the active agents to a small tumor area.

Upon formulation, solutions will be administered in a manner compatible with the dosage formulation and/or in such amount as is therapeutically effective. The formulations are easily administered in a variety of dosage forms, such as the type of injectable solutions described above, but drug release capsules and/or the like can also be employed.

For parenteral administration in an aqueous solution, for example, the solution should be suitably buffered if necessary and/or the liquid diluent first rendered isotonic with sufficient saline and/or glucose. These particular aqueous solutions are especially suitable for intravenous, intramuscular, subcutaneous and/or intraperitoneal administration. In this connection, sterile aqueous media which can be employed will be known to those of skill in the art in light of the present disclosure. For example, one dosage could be dissolved in 1 ml of isotonic NaCl solution and/or either added to 1000 ml of hypodermoclysis fluid and/or injected at the proposed site of infusion, (see for example, "Remington's Pharmaceutical Sciences" 15th Edition, pages 1035-1038 and/or 1570-1580). Some variation in dosage will necessarily occur depending on the condition of the subject being treated. The person responsible for administration will, in any event, determine the appropriate dose for the individual subject.

In addition to the compounds formulated for parenteral administration, such as intravenous and/or intramuscular injection, other pharmaceutically acceptable forms include, e.g., tablets and/or other solids for oral administration; liposomal formulations; time release capsules; and/or any other form currently used, including cremes.

One may also use nasal solutions and/or sprays, aerosols and/or inhalants in the present invention. Nasal solutions are usually aqueous solutions designed to be administered to the nasal passages in drops and/or sprays. Nasal solutions are prepared so that they are similar in many respects to nasal secretions, so that normal ciliary action is maintained. Thus, the aqueous nasal solutions usually are isotonic and/or slightly buffered to maintain a pH of 5.5 to 6.5. In addition, antimicrobial preservatives, similar to those used in ophthalmic preparations, and/or appropriate drug stabilizers, if required, may be included in the formulation.

Additional formulations which are suitable for other modes of administration include vaginal suppositories and/or pessaries. A rectal peccary and/or suppository may also be used. Suppositories are solid dosage forms of various weights and/or shapes, usually medicated, for insertion into the rectum, vagina and/or the urethra. After insertion, suppositories soften, melt and/or dissolve in the cavity fluids. In general, for suppositories, traditional binders and/or carriers may include, for example, polyalkylene glycols and/or triglycerides; such suppositories may be formed from mixtures containing the active ingredient in the range of 0.5% to 10%, preferably 1%-2%.

Oral formulations include such normally employed excipients as, for example, pharmaceutical grades of mannitol, lactose, starch, magnesium stearate, sodium saccharine, cellulose, magnesium carbonate and/or the like. These compositions take the form of solutions, suspensions, tablets, pills, capsules, sustained release formulations and/or powders. In certain defined embodiments, oral pharmaceutical compositions will comprise an inert diluent and/or assailable edible carrier, and/or they may be enclosed in hard and/or soft shell gelatin capsule, and/or they may be compressed into tablets, and/or they may be incorporated directly with the food of the diet. For oral therapeutic administration, the active compounds may be incorporated with excipients and/or used in the form of ingestible tablets, buccal tables, troches, capsules, elixirs, suspensions, syrups, wafers, and/or the like. Such compositions and/or preparations should contain at least 0.1% of active compound. The percentage of the compositions and/or preparations may, of course, be varied and/or may conveniently be between about 2 to about 75% of the weight of the unit, and/or preferably between 25-60%. The amount of active compounds in such therapeutically useful compositions is such that a suitable dosage will be obtained.

The tablets, troches, pills, capsules and/or the like may also contain the following: a binder, as gum tragacanth, acacia, cornstarch, and/or gelatin; excipients, such as dicalcium phosphate; a disintegrating agent, such as corn starch, potato starch, alginic acid and/or the like; a lubricant, such as magnesium stearate; and/or a sweetening agent, such as sucrose, lactose and/or saccharin may be added and/or a flavoring agent, such as peppermint, oil of wintergreen, and/or cherry flavoring. When the dosage unit form is a capsule, it may contain, in addition to materials of the above type, a liquid carrier. Various other materials may be present as coatings and/or to otherwise modify the physical form of the dosage unit. For instance, tablets, pills, and/or capsules may be coated with shellac, sugar and/or both. A syrup of elixir may contain the active compounds sucrose as a sweetening agent methyl and/or propylparabens as preservatives, a dye and/or flavoring, such as cherry and/or orange flavor.

The examples of pharmaceutical preparations described above are merely illustrative and not exhaustive; the compositions of the present invention are amenable to most common pharmaceutical preparations.

Pharmaceutical compositions suitable for injectable use include sterile aqueous solutions (where water-soluble) or dispersions and sterile powders for the extemporaneous preparation of sterile injectable solutions or dispersion. For intravenous administration, suitable carriers include saline, Cremophor EL™ (BASF, Parsippany, N.J.) or phosphate buffered saline (PBS). The composition may be sterile and be fluid to the extent that easy syringability exists. It should be stable under the conditions of manufacture and storage and should be preserved against the contaminating action of microorganisms such as bacteria and fungi. The carrier may be a solvent or dispersion medium containing, e.g., water, ethanol, polyol (for example, glycerol, propylene glycol, and polyethylene glycol), and suitable mixtures thereof. The fluidity may be maintained, e.g., by the use of a coating such as lecithin, by the maintenance of the required particle size in the case of dispersion, and by the use of surfactants. Prevention of the microbial growth may be achieved by various antibacterial and antifungal agents, e.g., parabens, chlorobutanol, phenol, ascorbic acid, thimerosal. Isotonic agents may be included, e.g., sugars, polyalcohols such as mannitol, sorbitol, and sodium chloride. Prolonged absorption of the injectable compositions may be achieved by including in the composition an agent that delays absorption, for example, aluminum monostearate and gelatin.

Sterile injectable solutions may be prepared by incorporating the azimilide in the required amount in an appropriate solvent with one or a combination of ingredients enumerated above followed by filtered sterilization. Dispersion media may be prepared by incorporating the azimilide into a sterile vehicle that may contain a basic dispersion medium and other ingredients. In the case of sterile powders for the preparation of sterile injectable solutions, preferred methods of preparation include vacuum drying and freeze-drying which yields a powder of the compound plus any additional desired ingredients from a previously sterile-filtered solution thereof.

Oral compositions may include an inert diluent or an edible carrier. They may be enclosed in gelatin capsules or compressed into tablets. For oral administration, the agent may be contained in enteric forms to survive the stomach, or further coated or mixed for a release in a particular region of the GI tract by known methods. For the purpose of oral therapeutic administration, the compound may be incorporated with excipients and used in the form of tablets, troches, or capsules. Pharmaceutically compatible binding agents, and/or adjuvant materials may be included as part of the composition. The tablets, pills, capsules, troches and the like may contain any of the following ingredients, or compounds of a similar nature: a binder such as microcrystalline cellulose, gum tragacanth or gelatin; an excipient such as starch or lactose, a disintegrating agent such as alginic acid, Primogel™, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

For administration by inhalation, the compounds may be delivered in the form of an aerosol spray from pressured container or dispenser, which contains a suitable propellant, e.g., a gas such as carbon dioxide, or a nebulizer.

Systemic administration may also be by transmucosal or transdermal means. For transmucosal or transdermal administration, penetrants appropriate to the barrier to be permeated may be used in the formulation. Such penetrants are generally known in the art, and include, for example, for transmucosal administration, detergents, bile salts, and fusidic acid derivatives. Transmucosal administration may be accomplished using nasal sprays or suppositories. For transdermal administration, the compounds may be formulated into ointments, salves, gels, or creams as generally known in the art.

The compounds may also be prepared in the form of suppositories (e.g., with conventional suppository bases such as cocoa butter and other glycerides) or retention enemas for rectal delivery.

In one embodiment, the compounds are prepared with carriers that will protect the compound against rapid elimination from the body, such as a controlled release formulation, including implants and microencapsulated delivery systems. Biodegradable, biocompatible polymers may be used, such as ethylene vinyl acetate, polyanhydrides, polyglycolic acid, collagen, polyorthoesters, and polylactic acid. Methods for preparation of such formulations will be apparent to those skilled in the art. Liposomal suspensions may also be used as pharmaceutically acceptable carriers.

It may be advantageous to formulate oral or parenteral compositions in dosage unit form for ease of administration and uniformity of dosage. "Dosage unit form" as used herein refers to physically discrete units suited as unitary dosages for the subject to be treated, each unit containing a predetermined quantity of compound calculated to produce the desired therapeutic effect in association with a pharmaceutical carrier. The specification for the dosage unit forms of the invention may be dictated by and may be dependent on the characteristics of the compound and the particular therapeutic effect to be achieved, and the limitations inherent in the art of preparing such a compound for the treatment of animals.

EXAMPLE 1

Preparation of Hemi-Hydrate Form of Azimilide

Heat 1.7 grams (anhydrous basis) of azimilide and 4.5 mls water until azimilide dissolves. A suggested target temperature for heating is 60-80° C. Upon dissolution, an option exists to hot filter the solution to remove insoluble impurities. Slowly add 13 mls warm acetone while maintaining reaction temperature near 50° C. Maintain temperature and a slow addition rate at this step to minimize crystallization due to anti-solvent addition. The solution is then cooled to quickly induce crystallization. If desired, allow the crystals to ripen at 20-30° C. before finishing the cooling ramp. Cool to within a temperature range of 25° C. to −5° C. If desired, ripen prior to isolation by allowing the slurry to stir at a low temperature within the 25° C. to −5° C. range. Isolate by filtering and rinsing with a small volume of acetone. Allow the wet cake to dry either at room temperature or with gentle heat (up to 50° C.). In some cases, vacuum may be useful to assist in drying.

EXAMPLE 2

Preparation of Hemi-Hydrate Form of Azimilide

Heat 1.7 grams (anhydrous basis) of azimilide and 5.0 mls water until azimilide dissolves. A suggested target temperature for heating to dissolution is 60-80° C. Upon dissolution, an option exists to hot filter the solution to remove insoluble impurities. Add 14 mls warm methanol while maintaining a reaction temperature near 50° C. Maintain temperature and a slow addition rate at this step to minimize crystallization due to anti-solvent addition. The solution is then cooled to quickly induce crystallization. Ripen the crystals at approximately 25° C. as needed to ensure phase purity of the hemi-hydrate form. Cool to low temperatures prior to isolation if desired. Isolate by filtering and rinsing with a small volume of 90% methanol. Allow the wet cake to dry either at room temperature or with gentle heat (up to 40° C.). In some cases, vacuum may be useful to assist in drying.

EXAMPLE 3

Preparation of Anhydrate Form of Azimilide from Hemi-Hydrate

Slurry 1 gram of azimilide hemi-hydrate in at least 100 mls of dry methanol. Stir or shake at a temperature within the range of room temperature to 60° C. Purge with a dry environment or protect from water uptake. Allow solids to shake or stir until conversion is complete. A time requirement of hours to days is necessary depending upon starting particle size and temperature. If conversion is not complete within 2-3 weeks, check the methanol source to confirm that is dry. If necessary, filter partly converted solids and re-suspend in a fresh aliquot of dry methanol. Upon complete conversion, filter. Dry using gentle heat up to 60° C. with or without vacuum.

EXAMPLE 4

Preparation of Anhydrate Form of Azimilide

Heat 1.7 grams (anhydrous basis) of azimilide and 5.1 mls water until azimilide dissolves. A suggested target temperature for heating to dissolution is 60-80° C. Upon dissolution, an option exists to hot filter the solution may to remove insoluble impurities. Add 26 mls methanol and maintain a temperature of 60° C. Ripen the crystals at approximately 60° C. as needed to ensure phase purity of the anhydrate form. Isolate by filtering hot and rinsing with a small volume of methanol. Allow the wet cake to dry either at room temperature or with gentle heat (up to 60° C.). In some cases, vacuum may be useful to assist in drying.

EXAMPLE 5

Preparation of Anhydrate Form of Azimilide from Isopropanol Solvate

Expose the isopropanol form of Azimilide to 85% relative humidity, 20-25° C. Allow the material to remain in 85% RH conditions until converted to the anhydrate phase. If conversion is not complete within 48 hours, consider options for increasing the humidity exposure throughout the sample bed and for removal of the isopropanol as it outgases from the converting solvate.

EXAMPLE 6

Preparation of Isopropanol Solvate from Hemi-Hydrate

Shake or stir 4 grams of the hemi-hydrate form of azimilide in 50 mls of dry isopropanol at approximately 60° C. until the solids convert to the isopropanol solvate form. Use hemi-hydrate as the starting material and not anhydrate. Depending upon the starting material, actual temperature and agitation the conversion may require several days or weeks.

EXAMPLE 7

Analyses of the Polymorphs

Various polymorphs that may be obtained using the methods described above may be further characterized using the techniques described below.

Moisture contents observed for carefully prepared hemi-hydrate typically range from 1% to 2% with 1.4-1.8% most commonly observed. Theoretical water content for the hemi-hydrate is 1.67%. The hemi-hydrate may dry to lower water contents and still maintain the spectroscopy and XRD signatures of the fully hydrated material. Residual water content observed for the anhydrate ranged from none detected to about 0.3%. Isopropanol contents for the isopropanol solvate typically range from 8% to 12% with 9.5-10.5% most commonly observed. The theoretical solvent content for a mono isopropanol solvate is 10.2%.

Figure 2:
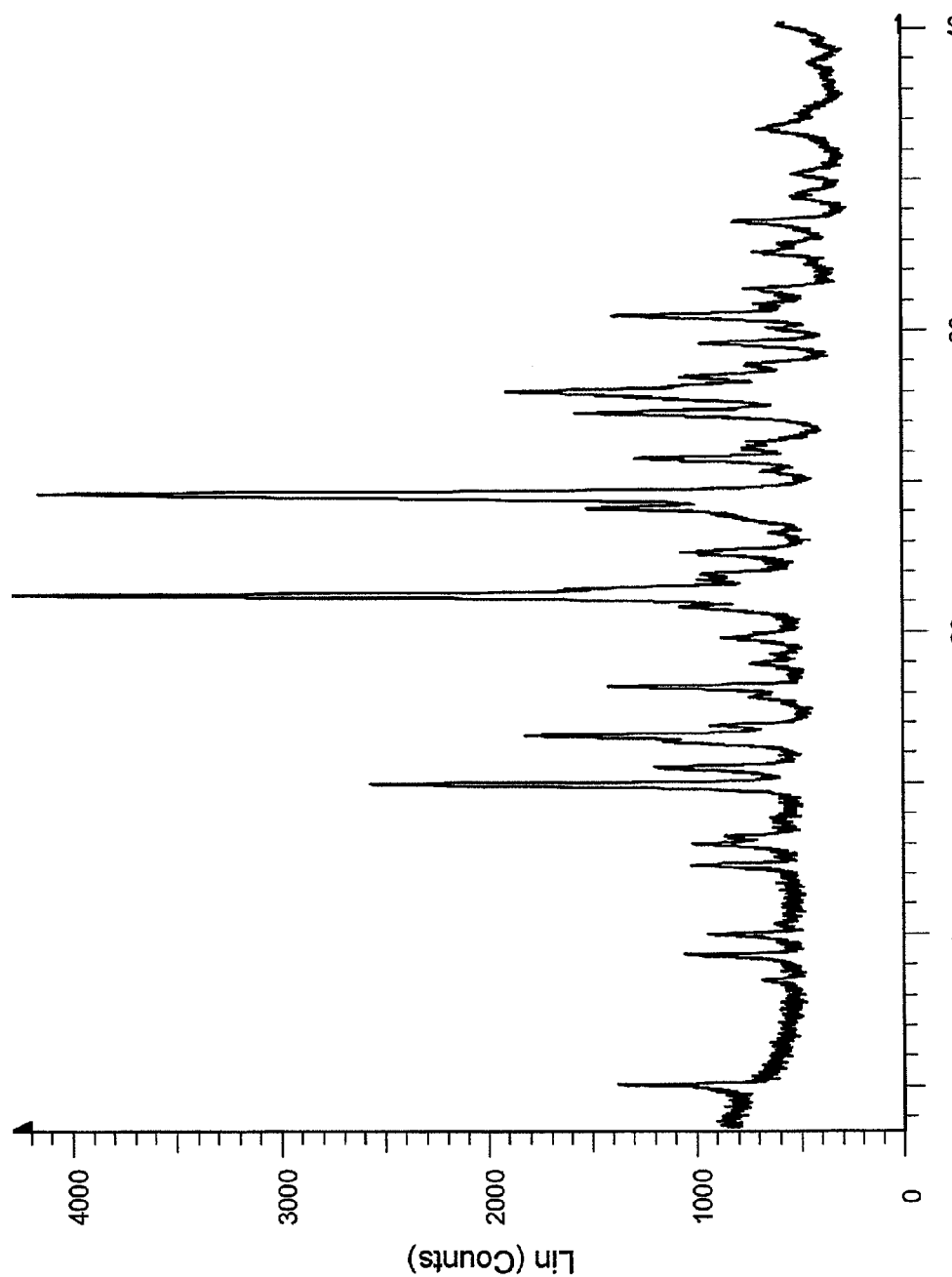
FIG. 2 shows a representative X-ray Diffraction Pattern for the anhydrate of Azimilide.
Figure 3:
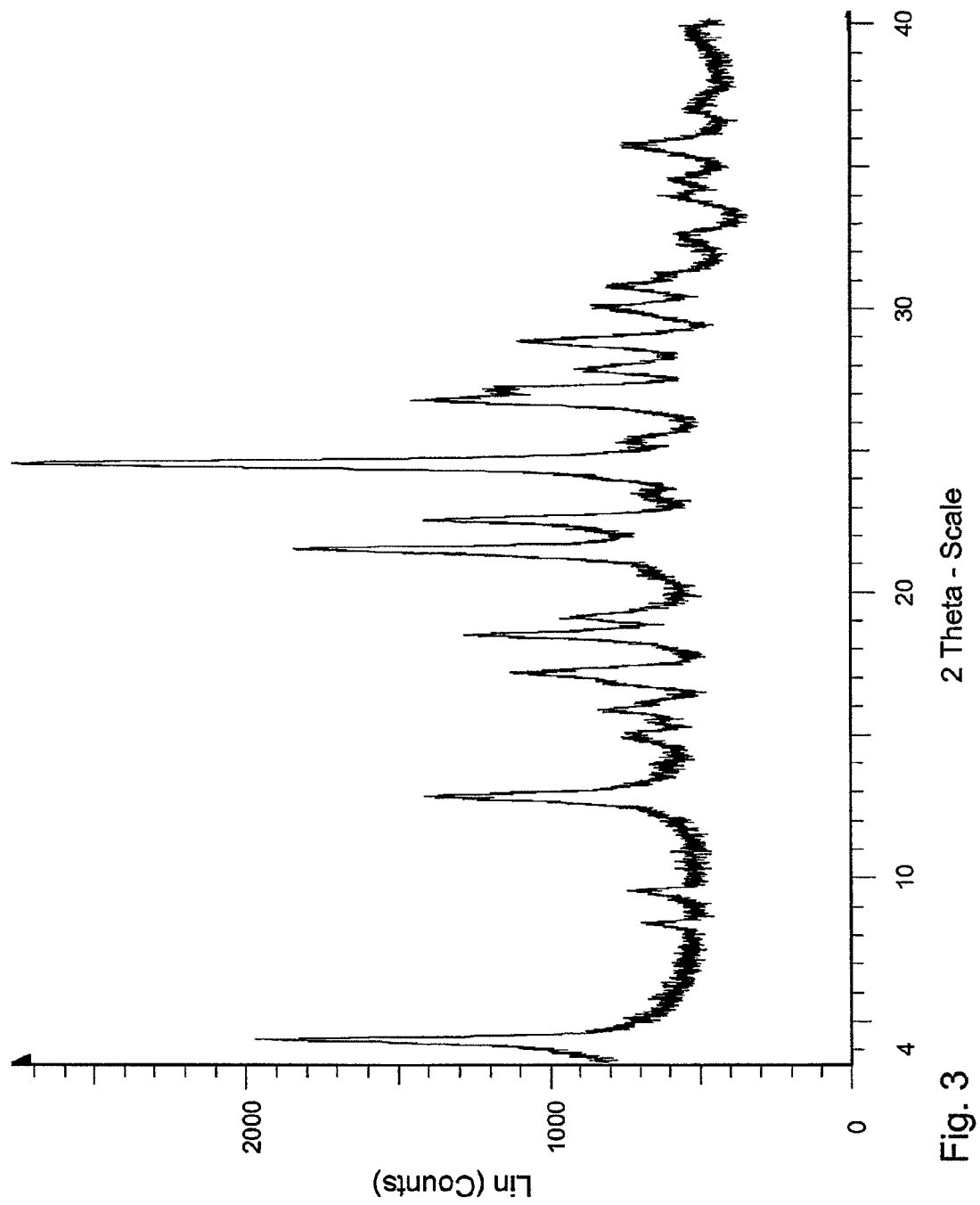
FIG. 3 shows a representative X-ray Diffraction Pattern for the isopropanol solvate of Azimilide.

X-ray Diffraction analysis: X-ray powder diffraction is performed on the samples using a Bruker D5000 X-Ray diffractometer. The D5000 is equipped with a 2.2 kW Cu anode X-ray tube, an Anton Parr TTK-1 low temperature stage, and high speed position sensitive detector (PSD). Cu K radiation (=1.5418.ANG.) is used to obtain powder patterns. A dual foil, nickel filter is placed in the receiving path of the X-Rays to remove the K .beta.-radiation. Material is mounted and analyzed on a front loading sample holder. Scans are performed over the range of 3.5-40 2 theta, at a 0.02 step size for 0.2 seconds per step. X-ray diffraction patterns for the hemi-hydrate, the anhydrous salt, and the isopropyl alcohol solvate are provided in FIGS. 1, 2, and 3, respectively.

Figure 4:
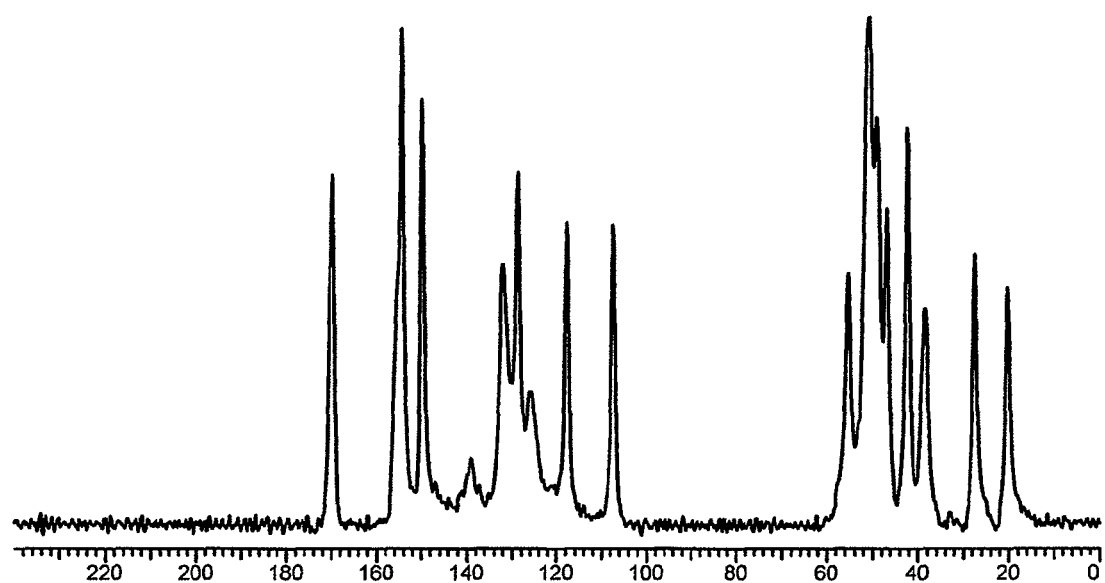
FIG. 4 shows a representative solid-state $^{13}$C NMR spectrum for the hemi-hydrate of Azimilide.
Figure 5:
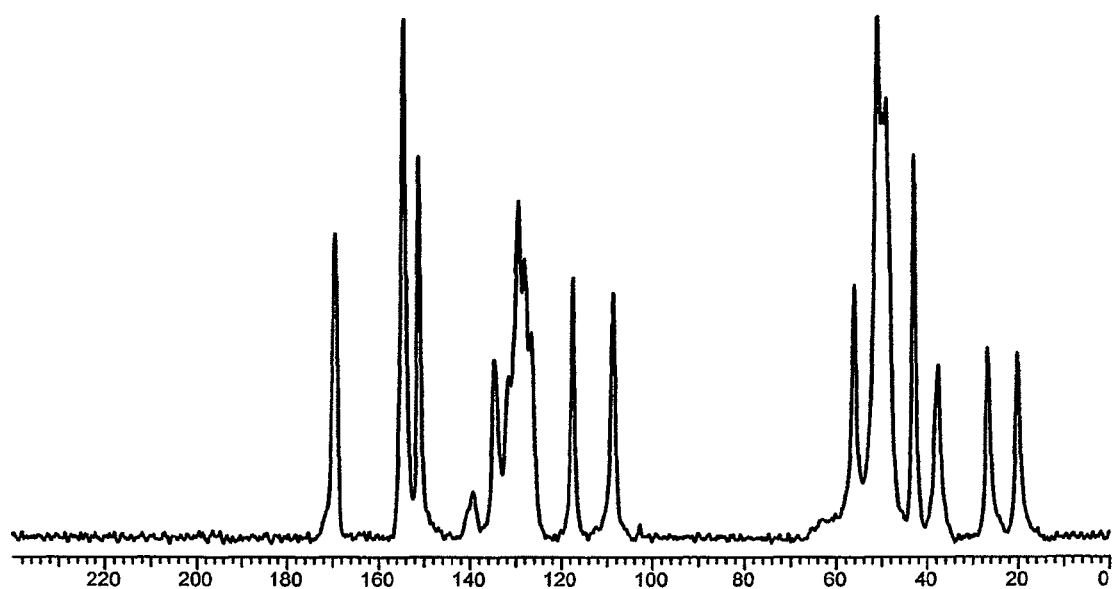
FIG. 5 shows a representative solid-state $^{13}$C NMR spectrum for the anhydrate of Azimilide.
Figure 6:
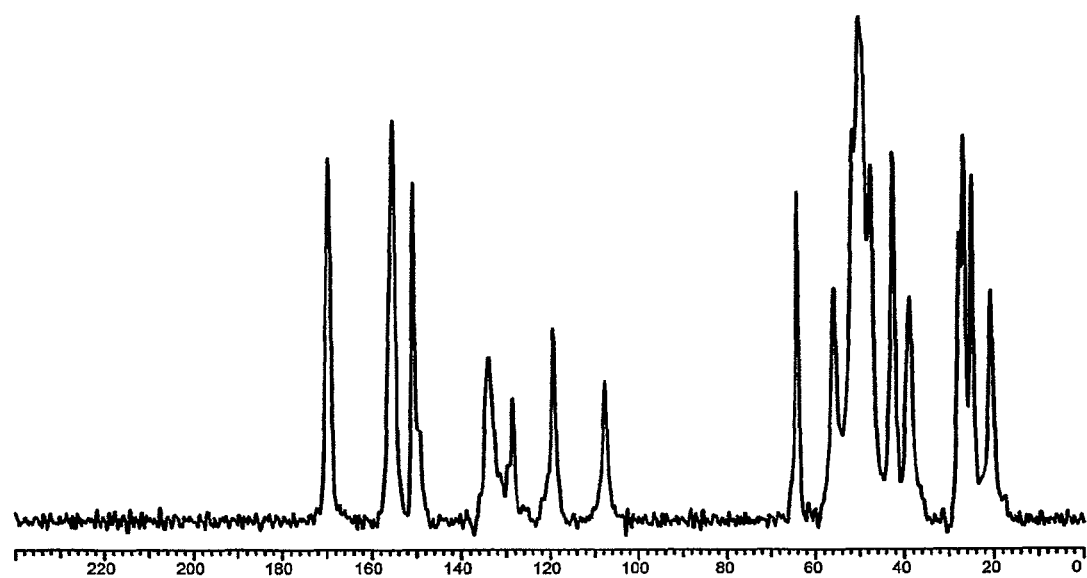
FIG. 6 shows a representative solid-state $^{13}$C NMR spectrum for the isopropanol solvate of Azimilide.

Solid-state Nuclear Magnetic Resonance (SSNMR) analysis: All data are recorded on a Varian 300 Unity Inova spectrometer equipped with a 7 mm CPMAS probe spinning at 5 kHz. The $^{13}$C spectra are recorded with the cross-polarization magic angle spinning (CP/MAS) TOSS (Total Suppression of Spinning Sideband) experiment. The samples are not ground but packed directly into 7 mm silicon nitride rotors. $^{13}$C NMR spectra for the hemi-hydrate, the anhydrous salt, and the isopropyl alcohol solvate are provided in FIGS. 4, 5, and 6, respectively.

Figure 7:
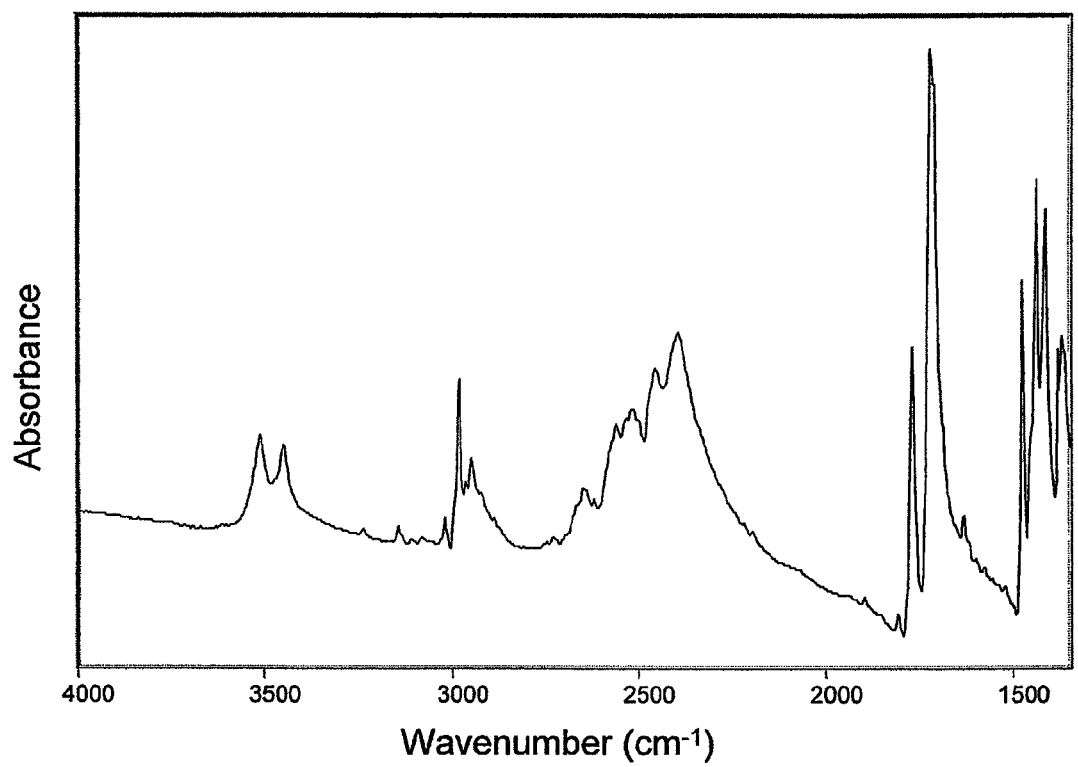
FIG. 7 shows a representative infrared spectrum for the hemi-hydrate of Azimilide.
Figure 8:
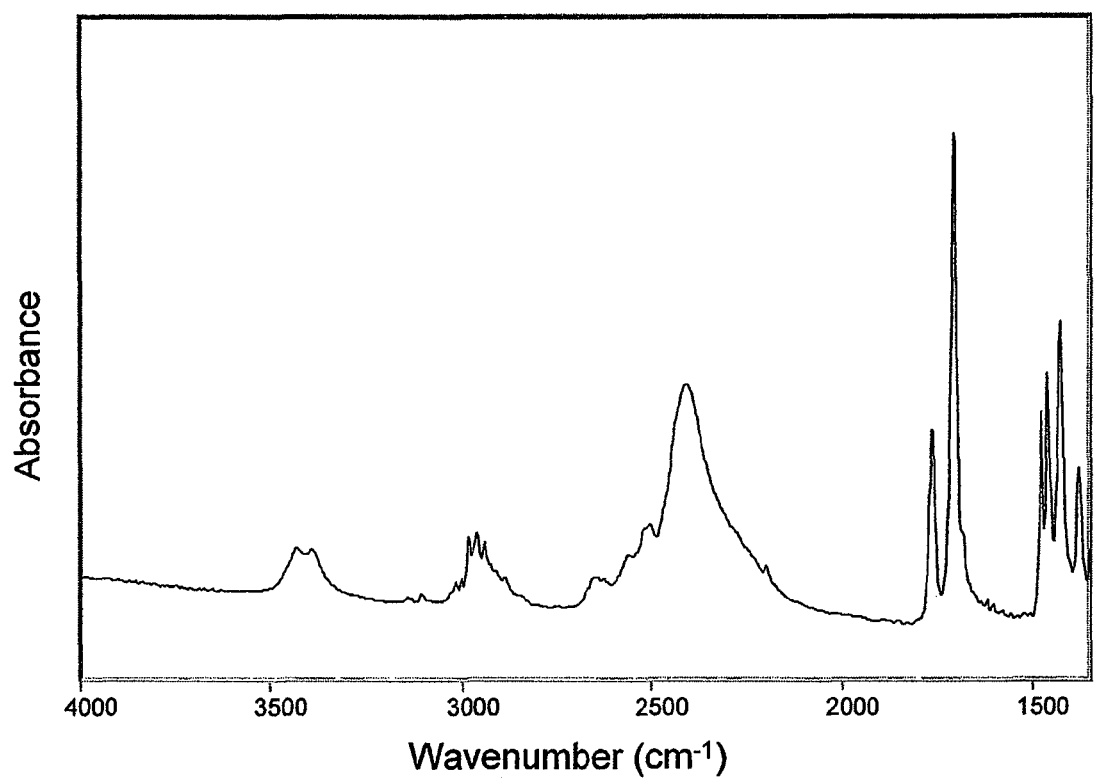
FIG. 8 shows a representative infrared spectrum for the anhydrate of Azimilide.
Figure 9:
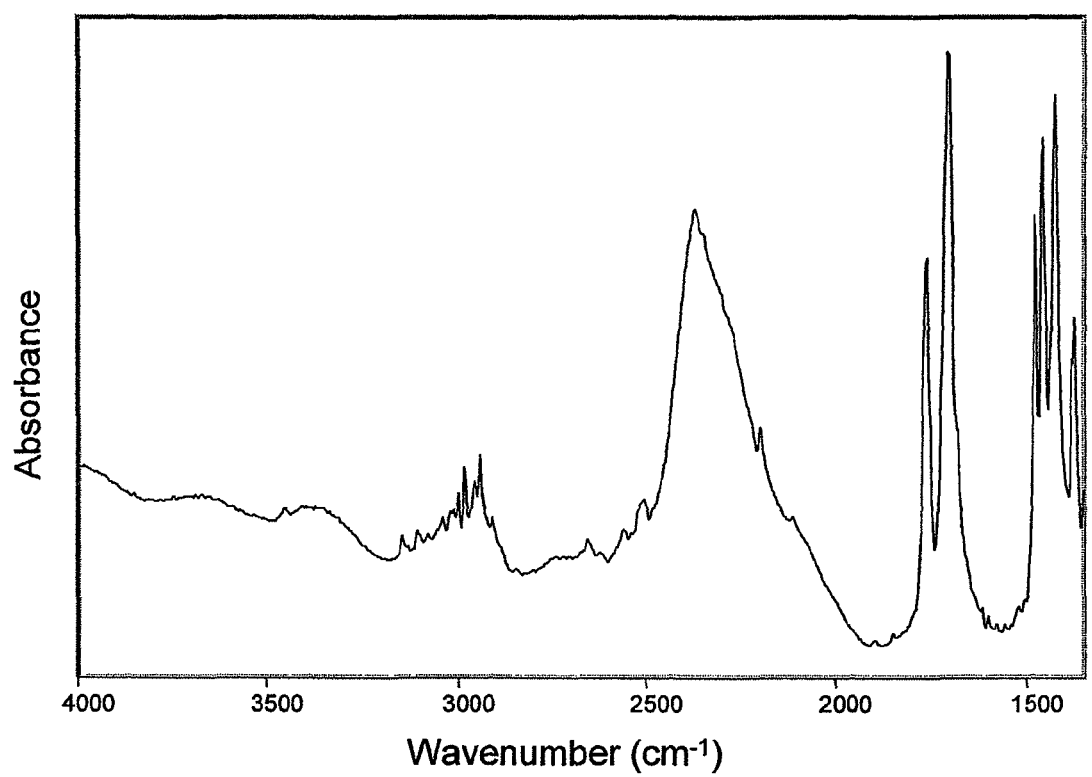
FIG. 9 shows a representative infrared spectrum for the isopropanol solvate of Azimilide.

Infrared (IR) analysis: The samples are analyzed using a BioRad FTS-3000 FTIR spectrometer. The instrument parameters include a 4,000 cm-1 to 1350 cm$^{-1}$ range using an instrument resolution of 4 cm$^{-1}$ with 16 scans. A fluorolube mull was prepared for each sample and placed in a KBr disc for analysis. A background of the clean KBr disc was recorded prior to sample collection. Infrared spectra for the hemi-hydrate, the anhydrous salt, and the isopropyl alcohol solvate are provided in FIGS. 7, 8, and 9, respectively.

Figure 10:
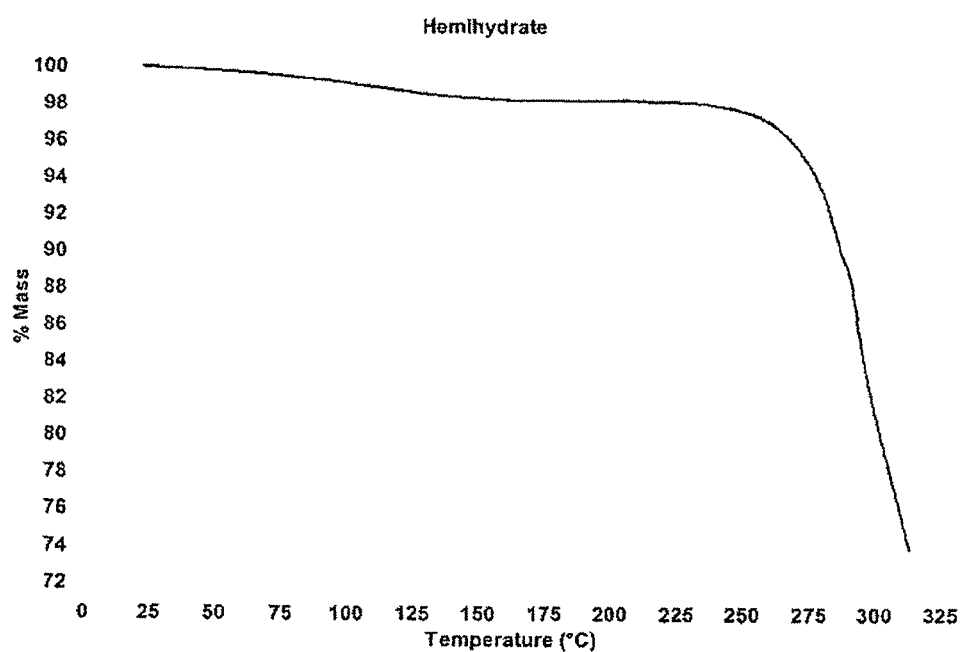
FIG. 10 shows a representative thermogravimetric analysis curve for the hemi-hydrate of Azimilide.
Figure 11:
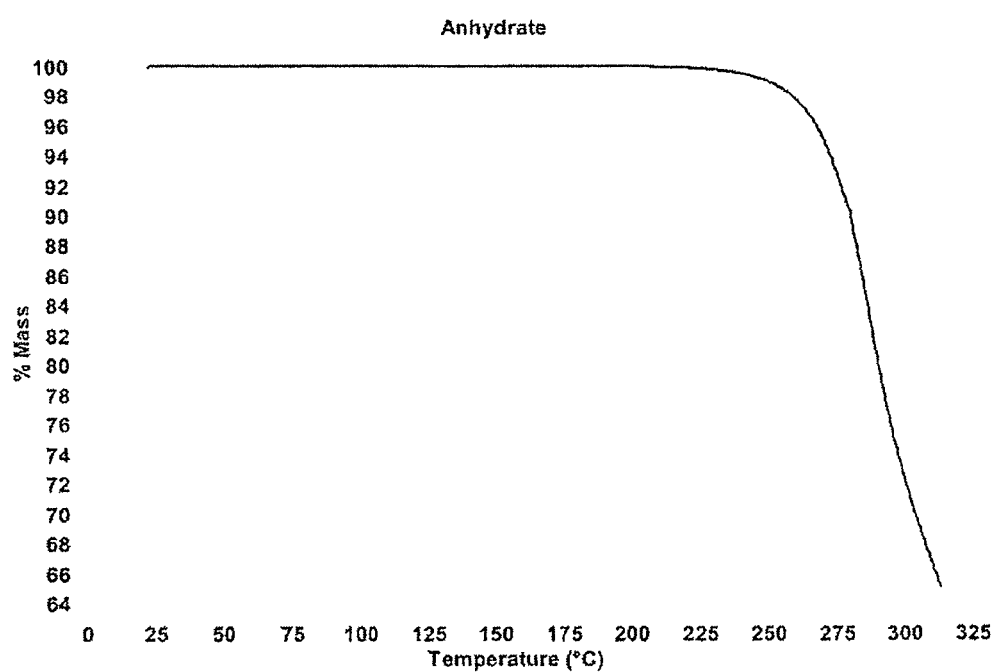
FIG. 11 shows a representative thermogravimetric analysis curve for the anhydrate of Azimilide.
Figure 12:
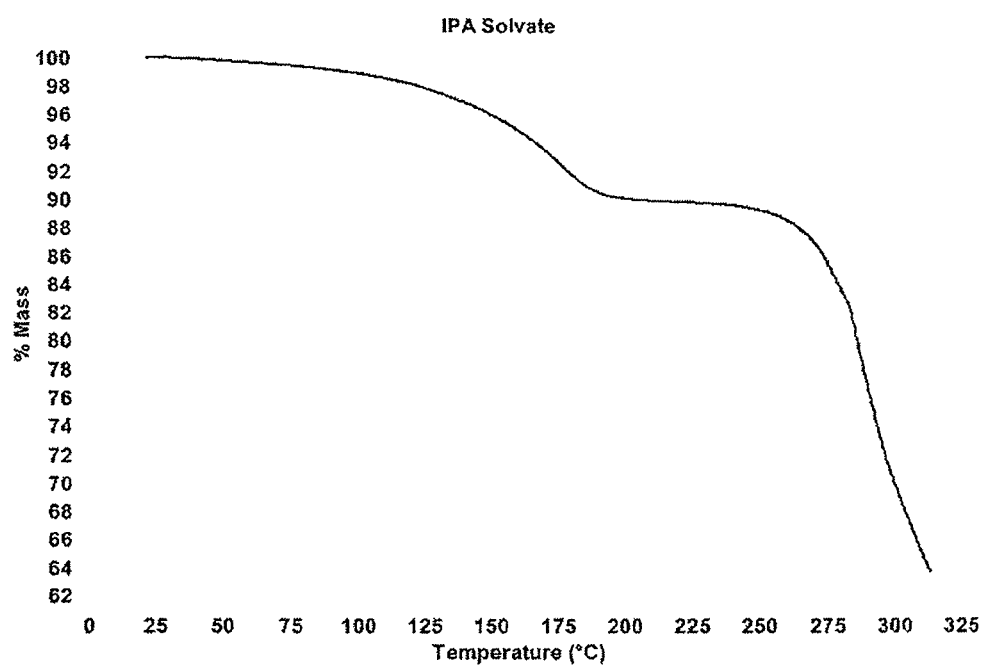
FIG. 12 shows a representative thermogravimetric analysis curve for the isopropanol solvate of Azimilide.

Thermogravimetric Analysis (TGA) determined solvation level. A Perkin-Elmer TGA-7 is used to generate water and solvent assays. Samples (5-12 mg) are run under dry nitrogen in open aluminum sample pans at a scan rate of 5° C./minute. TGA curves for the hemi-hydrate, the anhydrous salt, and the isopropyl alcohol solvate are provided in FIGS. 10, 11, and 12, respectively.

EXAMPLE 8

Characteristics of Various Salt Solvates

Hemi-Hydrate

In the solvent systems evaluated, the hemi-hydrate yielded particle sizes and shapes better suited to chemical process filtration and rinsing than did the anhydrate and EPA solvate forms. Large, plate-like crystals are typically obtained from the hemi-hydrate whereas the other two forms yielded smaller needles, rods or very narrow elongated plates that packed more tightly upon processing making filtration and flow more difficult.

The apparent water solubility of the hemi-hydrate is approximately 170 mg/ml at room temperature, providing a higher solubility and more rapid dissolution rate than that observed for the anhydrate form (160 mg/ml).

The water content of the hemi-hydrate is stable over a room temperature relative humidity range of 12% to 85% RH but may be dried from the compound under desiccation. The water content stability of the hemi-hydrate over this range of RH makes it particularly suitable for incorporation into solid dosage forms directly as a powder since the weight basis of the active substance does not change in varying humidity conditions. Upon extreme drying, the hemi-hydrate crystals fracture. Thus for this form, drying may be used as a non-mechanical means to reduce particle size.

Anhydrate

The anhydrate, because it does not contain water may provide advantages over the hemi-hydrate in formulations that are particularly water sensitive. While not as soluble as the hemi-hydrate, it is still freely soluble as per the USP definition of solubility (160 mg/ml). The anhydrate is not hygroscopic, exhibiting no evidence of water uptake at room temperature, under 85% relative humidity for up to 4 weeks.

Isopropanol Solvate

The isopropanol solvate provides the highest apparent water solubility of the three forms at 220 mg/ml, providing an advantage when very rapid dissolution or high solubility are desired. Unlike the anhydrate and hemi-hydrate, the isopropanol solvate is not stable upon exposure to humidity and at 85% relative humidity converts to the anhydrate form within days to weeks.

Collectively, the availability of three different solid state forms of Azimilide provides an advantage to the process chemist attempting to purify via crystallization. Each of the forms is isolated from distinctly different solvent systems. Impurities can be expected to exhibit differing solubility within these systems. Also, the various crystal forms are expected to exhibit differing propensity for co-crystallization with impurities. The availability of three distinct solid state forms provides the process chemist with the option of choosing to isolate from the form most able to exclude an impurity of concern. Also, the availability of three different solid state forms of Azimilide provides an advantage to the product formulator who can select for the most suitable physical handling properties consistent with the manufacturing process.

EXAMPLE 9

Azimilide Dihydrochloride Film-Coated Tablets

Tablets containing 75 mg and 125 mg of Azimilide are prepared as follows:

| Ingredient | Unit Quantity (mg/tablet) | Unit Quantity (mg/tablet) |
| --- | --- | --- |
| Core Tablet | 75 mg | 125 mg |
| Azimilide dihydrochloride | 75.0 | 125.0 |
| Lactose monohydrate NF | 359.2 | 319.1 |
| Microcrystalline cellulose NF | 133.7 | 118.7 |
| Crospovidone NF | 18.0 | 18.0 |
| Talc NF | 7.5 | 12.0 |
| Magnesium stearate NF | 6.6 | 6.6 |
| Colloidal silicon dioxide NF | 0.0 | 0.6 |
| Subtotal | 600 mg | 600 mg |
| Film Coating | | |
| Dri-Klear | 14.18 | 14.2 |
| Chroma-Tone White (DDB-7536W) | 3.82 | 3.65 |
| Ferric oxide red, NF | | 0.175 |
| Subtotal | 18 mg | 18 mg |

Total target tablet weight = 618 mg

EXAMPLE 10

Azimilide Hemi-Hydrate

Azimilide hemi-hydrate prepared by the process of examples 1 or 2 which contained an undesirably high concentration of impurities was subjected to further processing in efforts to improve purity. Surprisingly, it was discovered that when azimilide hemi-hydrate was subjected to a second crystallization step, a substantially more pure hemi-hydrate form was produced. For example, the concentration within azimilide hemi-hydrate of 1-[[[5-(4-chlorophenyl)-2-furanyl]methylene]amino]-3-[4-(chloro)butyl]-2,4-imidazolidine-dione (hereinafter, "impurity A") was dramatically reduced by preparing the hemi-hydrate in the manner disclosed in example 1 and then subjecting the hemi-hydrate to a subsequent crystallization step.

Reverse-phase high performance liquid chromatography (RP-HPLC) was used to determine the initial concentration of "impurity A" in azimilide hemi-hydrate. The RP-HPLC was performed on a 1.8 μm $C_{18}$ column using a mobile phase of methanol and acetate buffer (pH 4.5). Quantification was by UV at a wavelength of 340 nm against a "impurity A" standard.

Next, in efforts to decrease the concentration within the hemi-hydrate of impurity A, about 50 grams of the hemi-hydrate was charged into a Lab-Max automated organic synthesizer (fitted with a 600 ml glass reactor, a condenser, and a multi-port head with a nitrogen sweep of 125 ml/min). The reactor was then charged with 3 volumes of water and the reaction slurry was warmed over the course of about 10 minutes to about 80° C. To this mixture, varying amounts of acetone (5 to 9 volumes) was slowly charged through an addition funnel. The temperature of the mixture was then lowered to about 55° C. and sustained for about 10 minutes.

The mixture was then subjected to a "cooling down" period of variable length (ranging from 2 hours to 6 hours, as is indicated in the following table). The reaction mixtures were maintained at about −7° C. for about 1 hour. The reaction mixture was then split in half by volume. One half was filtered without an acetone wash and then placed in a vacuum oven at about 50° C. overnight. The other half of the reaction mixture was held overnight at about −7° C. in the reactor, then filtered and washed with about 6 volumes of acetone. The product was then dried in a vacuum oven at about 50° C. overnight.

Following the drying process, the azimilide hemi-hydrate was analyzed to determine the final concentration within the hemi-hydrate of impurity A.

As is set forth in the table, certain process variables resulted in a surprising decrease in impurity A concentration within azimilide hemi-hydrate.

| Run | Acetone (vol.) | Water (vol. | Cooling Time (hours) | Acetone Wash (vol.) | Initial Impurity A (%) | Final Impurity A(%) | % Purity Improvement |
|---|---|---|---|---|---|---|---|
| 1 | 5 | 3 | 2 | n/a | 0.004 | 0.0015 | 62.5% |
| 2 | 5 | 3 | 2 | 6 | 0.004 | 0.0007 | 82.5% |
| 3 | 5 | 3 | 2 | n/a | 0.004 | 0.0015 | 62.5% |
| 4 | 5 | 3 | 2 | 6 | 0.004 | 0.0006 | 85.0% |
| 5 | 9 | 3 | 2 | n/a | 0.004 | 0.0008 | 80.0% |
| 6 | 9 | 3 | 2 | 6 | 0.004 | 0.0003 | 92.5% |
| 7 | 9 | 3 | 2 | n/a | 0.004 | 0.0008 | 80.0% |
| 8 | 9 | 3 | 2 | 6 | 0.010 | 0.0005 | 95.0% |
| 9 | 5 | 3 | 4 | n/a | 0.010 | 0.0016 | 84.0% |
| 10 | 5 | 3 | 4 | 6 | 0.010 | 0.0015 | 85.0% |
| 11 | 5 | 3 | 4 | n/a | 0.010 | 0.005 | 50.0% |
| 12 | 5 | 3 | 4 | 6 | 0.010 | 0.0016 | 84.0% |
| 13 | 9 | 3 | 4 | n/a | 0.010 | 0.002 | 80.0% |
| 14 | 9 | 3 | 4 | 6 | 0.010 | 0.0007 | 93.0% |
| 15 | 9 | 3 | 4 | n/a | 0.010 | 0.0014 | 86.0% |
| 16 | 9 | 3 | 4 | 6 | 0.010 | 0.0007 | 93.0% |
| 17 | 5 | 3 | 6 | n/a | 0.010 | 0.003 | 70.0% |
| 18 | 5 | 3 | 6 | 6 | 0.010 | 0.0015 | 85.0% |
| 19 | 5 | 3 | 6 | n/a | 0.010 | 0.004 | 60.0% |
| 20 | 5 | 3 | 6 | 6 | 0.010 | 0.0022 | 78.0% |
| 21 | 9 | 3 | 6 | n/a | 0.010 | 0.001 | 90.0% |
| 22 | 9 | 3 | 6 | 6 | 0.010 | 0.0007 | 93.0% |
| 23 | 9 | 3 | 6 | n/a | 0.010 | 0.0019 | 81.0% |
| 24 | 9 | 3 | 6 | 6 | 0.010 | 0.0008 | 92.0% |
| 25 | 5 | 3 | 2 | n/a | 0.010 | 0.004 | 60.0% |
| 26 | 5 | 3 | 2 | 6 | 0.010 | 0.003 | 70.0% |
| 27 | 5 | 3 | 2 | n/a | 0.010 | 0.004 | 60.0% |
| 28 | 5 | 3 | 2 | 6 | 0.010 | 0.0029 | 71.0% |
| 29 | 9 | 3 | 2 | n/a | 0.010 | 0.0019 | 81.0% |
| 30 | 9 | 3 | 2 | 6 | 0.010 | 0.0008 | 92.0% |
| 31 | 9 | 3 | 2 | n/a | 0.010 | 0.0020 | 80.0% |
| 32 | 9 | 3 | 2 | 6 | 0.010 | 0.0008 | 92.0% |
| 33 | 9 | 3 | 4 | 6 | 0.007 | 0.0003 | 95.7% |
| 34 | 9 | 3 | 4 | 6 | 0.007 | 0.0003 | 95.7% |

The following Points are non-limiting embodiments of the present invention:

Point 1. A method for preparing an isopropanol solvate of (E)-1-[[[5-(4-chlorophenyl)-2-furanyl]methylene]amino]-3-[4-(4-methyl-1-piperazinyl)butyl]-2,4-imidazolidinedione dihydrochloride in substantially pure form, wherein the method comprises:
(a) heating a mixture of water and (E)-1-[[[5-(4-chlorophenyl)-2-furanyl]methylene]amino]-3-[4-(4-methyl-1-piperazinyl)butyl]-2,4-imidazolidinedione dihydrochloride to form a heated mixture;
(b) combining the heated mixture with acetone;
(c) isolating a hemi-hydrate of (E)-1-[[[5-(4-chlorophenyl)-2-furanyl]methylene]amino]-3-[4-(4-methyl-1-piperazinyl)butyl]-2,4-imidazolidinedione dihydrochloride; and
(d) combining the hemi-hydrate with isopropanol to form the isopropanol solvate of (E)-1-[[[5-(4-chlorophenyl)-2-furanyl]methylene]amino]-3-[4-(4-methyl-1-piperazinyl)butyl]-2,4-imidazolidinedione dihydrochloride.

Point 2. The method of Point 1, where method further comprises recrystallizing the isopropanol solvate in acetone in a step (e).

Point 3. The method of Point 1, wherein the isopropanol solvate comprises between about 9% and about 11% isopropanol by weight.

Point 4. The method of Point 1, wherein the isopropanol solvate comprises an X-ray diffraction pattern characterized substantially in accordance with the pattern of FIG. 3.

Point 5. The method of Point 1, wherein the isopropanol solvate comprises has a solid-state 13C NMR spectrum characterized substantially in accordance with the solid-state 13C NMR spectrum of FIG. 6.

Point 6. The method of Point 1, wherein the isopropanol solvate has an infrared spectrum characterized substantially in accordance with the infrared spectrum of FIG. 9.

Point 7. The method of Point 1, wherein the isopropanol solvate has a thermogravimetric analysis curve characterized substantially in accordance with the pattern of FIG. 12.

Point 8. The method of Point 1, wherein the isopropanol solvate comprises X-ray diffraction peaks at 2 theta values of about 4.33, about 9.51, about 12.8, about 17.16, about 18.5 and about 21.53 degrees.

Point 9. The method of Point 1, wherein the isopropanol solvate comprises has IR absorbance peaks at about 3428 and 3390 wave numbers.

Point 10. The method of Point 1, wherein the isopropanol solvate has an X-ray powder diffraction pattern comprising peaks at about 4.33+/−0.2 degrees 2 theta, at about 12.8+/−0.2 degrees 2 theta, and at about 21.53+/−0.2 degrees 2 theta.

Point 11. The method of Point 1, wherein step (a) comprises heating the mixture to a temperature of about 60-80° C.

Point 12. The method of Point 1, wherein step (b) comprises combining the heated mixture with acetone, maintaining the mixture at a temperature of about 50° C., and then cooling the mixture to induce crystallization.

Point 13. An isopropanol solvate of (E)-1-[[[5-(4-chlorophenyl)-2-furanyl]methylene]amino]-3-[4-(4-methyl-1-piperazinyl)butyl]-2,4-imidazolidinedione prepared by the process of any of Points 1-12.

Point 14. An isopropanol solvate of (E)-1-[[[5-(4-chlorophenyl)-2-furanyl]methylene]amino]-3-[4-(4-methyl-1-piperazinyl)butyl]-2,4-imidazolidinedione.

Point 15. The isopropanol solvate of Point 14, wherein the isopropanol solvate has an X-ray powder diffraction pattern comprising peaks at about 4.33+/−0.2 degrees 2 theta, at about 12.8+/−0.2 degrees 2 theta, and at about 21.53+/−0.2 degrees 2 theta.

Point 16. The isopropanol solvate of any of Points 14-15, wherein the isopropanol solvate is substantially pure of 1-[[[5-(4-chlorophenyl)-2-furanyl]methylene]amino]-3-[4-(chloro)butyl]-2,4-imidazolidinedione.

Point 17. The isopropanol solvate of any of Points 14-15, wherein the isopropanol solvate comprises about 0.0025% or less of 1-[[[5-(4-chlorophenyl)-2-furanyl]methylene]amino]-3-[4-(chloro)butyl]-2,4-imidazolidinedione.

Point 18. The isopropanol solvate of any of Points 14-15, wherein the isopropanol solvate comprises between about 0.000001% and about 0.0025% by weight of 1-[[[5-(4-chlorophenyl)-2-furanyl]methylene]amino]-3-[4-(chloro)butyl]-2,-4-imidazolidinedione.

Point 19. The isopropanol solvate of any of Points 14-15, wherein the isopropanol solvate comprises between 0.0001% and 0.0025% by weight of 1-[[[5-(4-chlorophenyl)-2-furanyl]methylene]amino]-3-[4-(chloro)butyl]-2,-4-imidazolidinedione.

Point 20. The isopropanol solvate of any of Points 14-15, wherein the isopropanol solvate is substantially pure of 5-(4-chlorophenyl)-2-furancarboxaldehyde.

Point 21. The isopropanol solvate of any of Points 14-15, wherein the isopropanol solvate comprises about 0.2% or less of 5-(4-chlorophenyl)-2-furancarboxaldehyde.

Point 22. The isopropanol solvate of any of Points 14-15, wherein the isopropanol solvate comprises between about 0.00001% and about 0.2% by weight of 5-(4-chlorophenyl)-2-furancarboxaldehyde.

Point 23. The isopropanol solvate of any of Points 14-15, wherein the isopropanol solvate comprises between 0.001% and 0.2% by weight of 5-(4-chlorophenyl)-2-furancarboxaldehyde.

Point 24. The isopropanol solvate of any of Points 14-15, wherein the isopropanol solvate is substantially pure of 1,4-bis[4-[1-[[[5-(4-chlorophenyl)-2-furanyl]methylene]amino]-2,4-dioxo-3imidazolidinyl]butyl]-1-methylpiperazinium chloride.

Point 25. The isopropanol solvate of any of Points 14-15, wherein the isopropanol solvate comprises about 0.5% or less of 1,4-bis[4-[1-[[[5-(4-chlorophenyl)-2-furanyl]methylene]amino]-2,4-dioxo-3imidazolidinyl]butyl]-1-methylpiperazinium chloride.

Point 26. The isopropanol solvate of any of Points 14-15, wherein the isopropanol solvate comprises between about 0.00001% and about 0.5% by weight of 1,4-bis[4-[1-[[[5-(4-chlorophenyl)-2-furanyl]methylene]amino]-2,4-dioxo-3imidazolidinyl]butyl]-1-methylpiperazinium chloride.

Point 27. The isopropanol solvate of any of Points 14-15, wherein the isopropanol solvate comprises between 0.00001% and 0.5% by weight of 1,4-bis[4-[1-[[[5-(4-chlorophenyl)-2-furanyl]methylene]amino]-2,4-dioxo-3imidazolidinyl]butyl]-1-methylpiperazinium chloride.

Point 28. The isopropanol solvate of any of Points 14-15, wherein the isopropanol solvate comprises between 0.00001% and 0.4% by weight of 1,4-bis[4-[1-[[[5-(4-chlorophenyl)-2-furanyl]methylene]amino]-2,4-diox-o-3-imidazolidinyl]butyl]-1-methylpiperazinium chloride.

Point 29. The isopropanol solvate of any of Points 14-15, wherein the isopropanol solvate is substantially free/pure of 3,3'-[1,4-Piperazinediylbis(butylene)]bis[1-[[[5-(4-chlorophenyl)-2-furan-yl]methylene]amino]-2,4-imidazolidinedione].

Point 30. The isopropanol solvate of any of Points 14-15, wherein the isopropanol solvate comprises about 0.3% or less of 3,3'-[1,4-Piperazinediylbis(butylene)]bis[1-[[[5-(4-chlorophenyl)-2-furan-yl]methylene]amino]-2,4-imidazolidinedione].

Point 31. The isopropanol solvate of any of Points 14-15, wherein the isopropanol solvate comprises between about 0.00001% and about 0.3% by weight of 3,3'-[1,4-Piperazinediylbis(butylene)]bis[1-[[[5-(4-chlorophenyl)-2-furan-yl]methylene]amino]-2,4-imidazolidinedione].

Point 32. The isopropanol solvate of any of Points 14-15, wherein the isopropanol solvate comprises between 0.00001% and 0.3% by weight of 3,3'-[1,4-Piperazinediylbis(butylene)]bis[1-[[[5-(4-chlorophenyl)-2-furan-yl]methylene]amino]-2,4-imidazolidinedione].

Point 33. The isopropanol solvate of any of Points 14-15, wherein the isopropanol solvate is substantially pure of 1-[[[5-(4-chlorophenyl)-2-furanyl]methylene]amino]-3-[4-(chloro)butyl]-2,4-imidazolidinedione and 5-(4-chlorophenyl)-2-furancarboxaldehyde.

Point 34. The isopropanol solvate of any of Points 14-15, wherein the isopropanol solvate comprises about 0.0025% or less of 1-[[[5-(4-chlorophenyl)-2-furanyl]methylene]amino]-3-[4-(chloro)butyl]-2,-4-imidazolidinedione and about 0.2% or less of 5-(4-chlorophenyl)-2-furancarboxaldehyde.

Point 35. The isopropanol solvate of any of Points 14-15, wherein the isopropanol solvate comprises between about 0.0001% and about 0.0025% by weight of 1-[[[5-(4-chlorophenyl)-2-furanyl]methylene]amino]-3-[4-(chloro)butyl]-2,4-imidazolidinedione and between about 0.00001% and about 0.2% by weight of 5-(4-chlorophenyl)-2-furancarboxaldehyde.

Point 36. The isopropanol solvate of any of Points 14-15, wherein the isopropanol solvate comprises between 0.0001% and 0.0025% by weight of 1-[[[5-(4-chlorophenyl)-2-furanyl]methylene]amino]-3-[4-(chloro)butyl]-2,-4-imidazolidinedione and between about 0.00001% and 0.2% by weight of 5-(4-chlorophenyl)-2-furancarboxaldehyde.

Point 37. The isopropanol solvate of any of Points 14-15, wherein the isopropanol solvate is substantially free/pure of 1-[[[5-(4-chlorophenyl)-2-furanyl]methylene]amino]-3-[4-(chloro)butyl]-2,-4-imidazolidinedione, 5-(4-chlorophenyl)-2-furancarboxaldehyde, 1,4-bis[4-[1-[[[5-(4-chlorophenyl)-2-furanyl]methylene]amino]-2,4-dioxo-3imidazolidinyl]butyl]-1-methylpiperazinium chloride, and 3,3'-[1,4-Piperazinediylbis(butylene)]bis[1-[[[5-(4-chlorophenyl)-2-furan-yl]methylene]amino]-2,4-imidazolidinedione].

Point 38. The isopropanol solvate of any of Points 14-15, wherein the isopropanol solvate comprises about 0.0025% or less of 1-[[[5-(4-chlorophenyl)-2-furanyl]methylene]amino]-3-[4-(chloro)butyl]-2,-4-imidazolidinedione, about 0.2% or less of 5-(4-chlorophenyl)-2-furancarboxaldehyde, about 0.5% or less of 1,4-bis[4-[1-[[[5-(4-chlorophenyl)-2-furanyl]methylene]amino]-2,4-dioxo-3imidazolidinyl]butyl]-1-methylpiperazinium chloride, and about 0.3% or less of 3,3'-[1,4-Piperazinediylbis(butylene)]bis[1-[[[5-(4-chlorophenyl)-2-furan-yl]methylene]amino]-2,4-imidazolidinedione].

Point 39. The isopropanol solvate of any of Points 14-15, wherein the isopropanol solvate comprises between about 0.0001% and about 0.0025% by weight of 1-[[[5-(4-chlorophenyl)-2-furanyl]methylene]amino]-3-[4-(chloro)butyl]-2,-4-imidazolidinedione, between about 0.00001% and about 0.2% by weight of 5-(4-chlorophenyl)-2-furancarboxaldehyde, between about 0.00001% and about 0.5% by weight of 1,4-bis[4-[1-[[[5-(4-chlorophenyl)-2-furanyl]methylene]amino]-2,4-dioxo-3imidazolidinyl]butyl]-1-methylpiperazinium chloride, and between about 0.00001% and about 0.3% by weight of 3,3'-[1,4-Piperazinediylbis(butylene)]bis[1-[[[5-(4-chlorophenyl)-2-furan-yl]methylene]amino]-2,4-imidazolidinedione].

Point 40. The isopropanol solvate of any of Points 14-15, wherein the isopropanol solvate comprises between 0.0001% and 0.0025% by weight of 1-[[[5-(4-chlorophenyl)-2-furanyl]methylene]amino]-3-[4-(chloro)butyl]-2,-4-imidazolidinedione, between about 0.00001% and 0.2% by weight of 5-(4-chlorophenyl)-2-furancarboxaldehyde, between 0.00001% and 0.5% by weight of 1,4-bis[4-[1-[[[5-(4-chlorophenyl)-2-furanyl]methylene]amino]-2,4-dioxo-3imidazolidinyl]butyl]-1-methylpiperazinium chloride, and between 0.00001% and 0.3% by weight of 3,3'-[1,4-Piperazinediylbis(butylene)]bis[1-[[[5-(4-chlorophenyl)-2-furan-yl]methylene]amino]-2,4-imidazolidinedione].

Point 41. A method for preparing an anhydrate form of (E)-1-[[[5-(4-chlorophenyl)-2-furanyl]methylene]amino]-3-[4-(4-methyl-1-piperazinyl)butyl]-2,4-imidazolidinedione or pharmaceutically acceptable salt thereof, wherein the method comprises:

(a) heating a mixture of water and (E)-1-[[[5-(4-chlorophenyl)-2-furanyl]methylene]amino]-3-[4-(4-methyl-1-piperazinyl)butyl]-2,4-imidazolidinedione to form a heated mixture;
(b) combining the heated mixture with acetone;
(c) isolating a hemi-hydrate of (E)-1-[[[5-(4-chlorophenyl)-2-furanyl]methylene]amino]-3-[4-(4-methyl-1-piperazinyl)butyl]-2,4-imidazolidinedione; and
(d) combining the hemi-hydrate with dry methanol to form the anhydrate form of (E)-1-[[[5-(4-chlorophenyl)-2-furanyl]methylene]amino]-3-[4-(4-methyl-1-piperazinyl)butyl]-2,4-imidazolidinedione.

Point 42. The method of Point 41, wherein step (d) further comprises combining the mixture of hemi-hydrate and dry methanol with methanol.

Point 43. The method of Point 41, wherein step (d) further comprises cooling the mixture of hemi-hydrate, dry methanol, and methanol to induce crystallization.

Point 44. The method of Point 41, wherein the anhydrate form comprises between about 0% and about 0.3% (w/w) of water.

Point 45. The method of Point 41, wherein the anhydrate form has an X-ray powder diffraction pattern comprising X-ray diffraction peaks at about 14.9+/−0.2 degrees 2 theta, at about 21.17+/−0.2 degrees 2 theta, and at about 24.59 degrees+/−0.2 degrees 2 theta.

Point 46. The method of any of Points 41 and 45, wherein the anhydrate is substantially pure of 1-[[[5-(4-chlorophenyl)-2-furanyl]methylene]amino]-3-[4-(chloro)butyl]-2,-4-imidazolidinedione.

Point 47. The method of any of Points 41 and 45, wherein the anhydrate comprises about 0.0025% or less of 1-[[[5-(4-chlorophenyl)-2-furanyl]methylene]amino]-3-[4-(chloro)butyl]-2,-4-imidazolidinedione.

Point 48. The method of any of Points 41 and 45, wherein the anhydrate comprises between about 0.0001% and about 0.0025% by weight of 1-[[[5-(4-chlorophenyl)-2-furanyl]methylene]amino]-3-[4-(chloro)butyl]-2,-4-imidazolidinedione.

Point 49. The method of any of Points 41 and 45, wherein the anhydrate comprises between 0.0001% and 0.0025% by weight of 1-[[[5-(4-chlorophenyl)-2-furanyl]methylene]amino]-3-[4-(chloro)butyl]-2,-4-imidazolidinedione.

Point 50. The method of any of Points 41 and 45, wherein the anhydrate is substantially pure of 5-(4-chlorophenyl)-2-furancarboxaldehyde.

Point 51. The method of any of Points 41 and 45, wherein the anhydrate comprises about 0.2% or less of 5-(4-chlorophenyl)-2-furancarboxaldehyde.

Point 52. The method of any of Points 41 and 45, wherein the anhydrate comprises between about 0.00001% and about 0.2% by weight of 5-(4-chlorophenyl)-2-furancarboxaldehyde.

Point 53. The method of any of Points 41 and 45, wherein the anhydrate comprises between 0.00001% and 0.2% by weight of 5-(4-chlorophenyl)-2-furancarboxaldehyde.

Point 54. The method of any of Points 41 and 45, wherein the anhydrate is substantially pure of 1,4-bis[4-[1-[[[5-(4-chlorophenyl)-2-furanyl]methylene]amino]-2,4-dioxo-3imidazolidinyl]butyl]-1-methylpiperazinium chloride.

Point 55. The method of any of Points 41 and 45, wherein the anhydrate comprises about 0.5% or less of 1,4-bis[4-[1-[[[5-(4-chlorophenyl)-2-furanyl]methylene]amino]-2,4-dioxo-3imidazolidinyl]butyl]-1-methylpiperazinium chloride.

Point 56. The method of any of Points 41 and 45, wherein the anhydrate comprises between about 0.00001% and about 0.5% by weight of 1,4-bis[4-[1-[[[5-(4-chlorophenyl)-2-furanyl]methylene]amino]-2,4-dioxo-3imidazolidinyl]butyl]-1-methylpiperazinium chloride.

Point 57. The method of any of Points 14-15, wherein the anhydrate comprises between 0.00001% and 0.5% by weight of 1,4-bis[4-[1-[[[5-(4-chlorophenyl)-2-furanyl]methylene]amino]-2,4-dioxo-3imidazolidinyl]butyl]-1-methylpiperazinium chloride.

Point 58. The method of any of Points 41 and 45, wherein the anhydrate comprises between 0.00001% and 0.4% by weight of 1,4-bis[4-[1-[[[5-(4-chlorophenyl)-2-furanyl]methylene]amino]-2,4-diox-o-3-imidazolidinyl]butyl]-1-methylpiperazinium chloride.

Point 59. The method of any of Points 41 and 45, wherein the anhydrate is substantially free/pure of 3,3'-[1,4-Piperazinediylbis(butylene)]bis[1-[[[5-(4-chlorophenyl)-2-furan-yl]methylene]amino]-2,4-imidazolidinedione].

Point 60. The method of any of Points 41 and 45, wherein the anhydrate comprises about 0.3% or less of 3,3'-[1,4-Piperazinediylbis(butylene)]bis[1-[[[5-(4-chlorophenyl)-2-furan-yl]methylene]amino]-2,4-imidazolidinedione].

Point 61. The method of any of Points 41 and 45, wherein the anhydrate comprises between about 0.00001% and about 0.3% by weight of 3,3'-[1,4-Piperazinediylbis(butylene)]bis[1-[[[5-(4-chlorophenyl)-2-furan-yl]methylene]amino]-2,4-imidazolidinedione].

Point 62. The method of any of Points 41 and 45, wherein the anhydrate comprises between 0.00001% and 0.3% by weight of 3,3'-[1,4-Piperazinediylbis(butylene)]bis[1-[[[5-(4-chlorophenyl)-2-furan-yl]methylene]amino]-2,4-imidazolidinedione].

Point 63. The method of any of Points 41 and 45, wherein the anhydrate is substantially pure of 1-[[[5-(4-chlorophenyl)-2-furanyl]methylene]amino]-3-[4-(chloro)butyl]-2,-4-imidazolidinedione and 5-(4-chlorophenyl)-2-furancarboxaldehyde.

Point 64. The method of any of Points 41 and 45, wherein the anhydrate comprises about 0.0025% or less of 1-[[[5-(4-chlorophenyl)-2-furanyl]methylene]amino]-3-[4-(chloro)butyl]-2,-4-imidazolidinedione and about 0.2% or less of 5-(4-chlorophenyl)-2-furancarboxaldehyde.

Point 65. The method of any of Points 41 and 45, wherein the anhydrate comprises between about 0.0001% and about 0.0025% by weight of 1-[[[5-(4-chlorophenyl)-2-furanyl]methylene]amino]-3-[4-(chloro)butyl]-2,-4-imidazolidinedione and between about 0.00001% and about 0.2% by weight of 5-(4-chlorophenyl)-2-furancarboxaldehyde.

Point 66. The method of any of Points 41 and 45, wherein the anhydrate comprises between 0.0001% and 0.0025% by weight of 1-[[[5-(4-chlorophenyl)-2-furanyl]methylene]amino]-3-[4-(chloro)butyl]-2,-4-imidazolidinedione and between about 0.00001% and 0.2% by weight of 5-(4-chlorophenyl)-2-furancarboxaldehyde.

Point 67. The method of any of Points 41 and 45, wherein the anhydrate is substantially free/pure of 1-[[[5-(4-chlorophenyl)-2-furanyl]methylene]amino]-3-[4-(chloro)butyl]-2,-4-imidazolidinedione, 5-(4-chlorophenyl)-2-furancarboxaldehyde, 1,4-bis[4-[1-[[[5-(4-chlorophenyl)-2-furanyl]methylene]amino]-2,4-dioxo-3imidazolidinyl]butyl]-1-methylpiperazinium chloride, and 3,3'-[1,4-Piperazinediylbis(butylene)]bis[1-[[[5-(4-chlorophenyl)-2-furan-yl]methylene]amino]-2,4-imidazolidinedione].

Point 68. The method of any of Points 41 and 45, wherein the anhydrate comprises about 0.0025% or less of 1-[[[5-(4-chlorophenyl)-2-furanyl]methylene]amino]-3-[4-(chloro)butyl]-2,-4-imidazolidinedione, about 0.2% or less of 5-(4-chlorophenyl)-2-furancarboxaldehyde, about 0.5% or less of 1,4-bis[4-[1-[[[5-(4-chlorophenyl)-2-furanyl]methylene]amino]-2,4-dioxo-3imidazolidinyl]butyl]-1-methylpiperazinium chloride, and about 0.3% or less of 3,3'-[1,4-Piperazinediylbis(butylene)]bis[1-[[[5-(4-chlorophenyl)-2-furan-yl]methylene]amino]-2,4-imidazolidinedione].

Point 69. The method of any of Points 41 and 45, wherein the anhydrate comprises between about 0.0001% and about 0.0025% by weight of 1-[[[5-(4-chlorophenyl)-2-furanyl]methylene]amino]-3-[4-(chloro)butyl]-2,-4-imidazolidinedione, between about 0.00001% and about 0.2% by weight of 5-(4-chlorophenyl)-2-furancarboxaldehyde, between about 0.00001% and about 0.5% by weight of 1,4-bis[4-[1-[[[5-(4-chlorophenyl)-2-furanyl]methylene]amino]-2,4-dioxo-3imidazolidinyl]butyl]-1-methylpiperazinium chloride, and between about 0.00001% and about 0.3% by weight of 3,3'-[1,4-Piperazinediylbis(butylene)]bis[1-[[[5-(4-chlorophenyl)-2-furan-yl]methylene]amino]-2,4-imidazolidinedione].

Point 70. The method of any of Points 41 and 45, wherein the anhydrate comprises between 0.0001% and 0.0025% by weight of 1-[[[5-(4-chlorophenyl)-2-furanyl]methylene]amino]-3-[4-(chloro)butyl]-2,-4-imidazolidinedione, between about 0.00001% and 0.2% by weight of 5-(4-chlorophenyl)-2-furancarboxaldehyde, between 0.00001% and 0.5% by weight of 1,4-bis[4-[1-[[[5-(4-chlorophenyl)-2-furanyl]methylene]amino]-2,4-dioxo-3imidazolidinyl]butyl]-1-methylpiperazinium chloride, and between 0.00001% and 0.3% by weight of 3,3'-[1,4-Piperazinediylbis(butylene)]bis[1-[[[5-(4-chlorophenyl)-2-furan-yl]methylene]amino]-2,4-imidazolidinedione].

Point 71. An anhydrate form of (E)-1-[[[5-(4-chlorophenyl)-2-furanyl]methylene]amino]-3-[4-(4-methyl-1-piperazinyl)butyl]-2,4-imidazolidinedione prepared by the process of any Points 41-70.

Point 72. An anhydrate form of (E)-1-[[[5-(4-chlorophenyl)-2-furanyl]methylene]amino]-3-[4-(4-methyl-1-piperazinyl)butyl]-2,4-imidazolidinedione or pharmaceutically acceptable salt thereof.

Point 73. The anhydrate of Point 72, wherein the anhydrate is in the form of the hydrochloride salt.

Point 74. The anhydrate of any of Points 72-73, wherein the anhydrate form comprises between about 0% and about 0.3% (w/w) of water.

Point 75. The anhydrate form of any of Points 72-74, wherein the anhydrate form has an X-ray powder diffraction pattern comprising X-ray diffraction peaks at about 14.9+/−0.2 degrees 2 theta, at about 21.17+/−0.2 degrees 2 theta, and at about 24.59 degrees+/−0.2 degrees 2 theta.

Point 76. The anhydrate form of any of Points 72-75, wherein the anhydrate is substantially pure of 1-[[[5-(4-chlorophenyl)-2-furanyl]methylene]amino]-3-[4-(chloro)butyl]-2,-4-imidazolidinedione.

Point 77. The anhydrate form of any of Points 72-75, wherein the anhydrate comprises about 0.0025% or less of 1-[[[5-(4-chlorophenyl)-2-furanyl]methylene]amino]-3-[4-(chloro)butyl]-2,-4-imidazolidinedione.

Point 78. The anhydrate form of any of Points 72-75, wherein the anhydrate comprises between about 0.0001% and about 0.0025% by weight of 1-[[[5-(4-chlorophenyl)-2-furanyl]methylene]amino]-3-[4-(chloro)butyl]-2,-4-imidazolidinedione.

Point 79. The anhydrate form of any of Points 72-75, wherein the anhydrate comprises between 0.0001% and 0.0025% by weight of 1-[[[5-(4-chlorophenyl)-2-furanyl]methylene]amino]-3-[4-(chloro)butyl]-2,-4-imidazolidinedione.

Point 80. The anhydrate form of any of Points 72-75, wherein the anhydrate is substantially pure of 5-(4-chlorophenyl)-2-furancarboxaldehyde.

Point 81. The anhydrate form of any of Points 72-75, wherein the anhydrate comprises about 0.2% or less of 5-(4-chlorophenyl)-2-furancarboxaldehyde.

Point 82. The anhydrate form of any of Points 72-75, wherein the anhydrate comprises between about 0.00001% and about 0.2% by weight of 5-(4-chlorophenyl)-2-furancarboxaldehyde.

Point 83. The anhydrate form of any of Points 72-75, wherein the anhydrate comprises between 0.00001% and 0.2% by weight of 5-(4-chlorophenyl)-2-furancarboxaldehyde.

Point 84. The anhydrate form of any of Points 72-75, wherein the anhydrate is substantially pure of, 4-bis[4-[1-[[[5-(4-chlorophenyl)-2-furanyl]methylene]amino]-2,4-dioxo-3imidazolidinyl]butyl]-1-methylpiperazinium chloride.

Point 85. The anhydrate form of any of Points 72-75, wherein the anhydrate comprises about 0.5% or less of 1,4-bis[4-[1-[[[5-(4-chlorophenyl)-2-furanyl]methylene]amino]-2,4-dioxo-3imidazolidinyl]butyl]-1-methylpiperazinium chloride.

Point 86. The anhydrate form of any of Points 72-75, wherein the anhydrate comprises between about 0.00001% and about 0.5% by weight of 1,4-bis[4-[1-[[[5-(4-chlorophenyl)-2-furanyl]methylene]amino]-2,4-dioxo-3imidazolidinyl]butyl]-1-methylpiperazinium chloride.

Point 87. The method of any of Points 14-15, wherein the anhydrate comprises between 0.00001% and 0.5% by weight of 1,4-bis[4-[1-[[[5-(4-chlorophenyl)-2-furanyl]methylene]amino]-2,4-dioxo-3imidazolidinyl]butyl]-1-methylpiperazinium chloride.

Point 88. The anhydrate form of any of Points 72-75, wherein the anhydrate comprises between 0.00001% and 0.4% by weight of 1,4-bis[4-[1-[[[5-(4-chlorophenyl)-2-furanyl]methylene]amino]-2,4-diox-o-3-imidazolidinyl]butyl]-1-methylpiperazinium chloride.

Point 89. The anhydrate form of any of Points 72-75, wherein the anhydrate is substantially free/pure of 3,3'-[1,4-Piperazinediylbis(butylene)]bis[1-[[[5-(4-chlorophenyl)-2-furan-yl]methylene]amino]-2,4-imidazolidinedione].

Point 90. The anhydrate form of any of Points 72-75, wherein the anhydrate comprises about 0.3% or less of 3,3'-[1,4-Piperazinediylbis(butylene)]bis[1-[[[5-(4-chlorophenyl)-2-furan-yl]methylene]amino]-2,4-imidazolidinedione].

Point 91. The anhydrate form of any of Points 72-75, wherein the anhydrate comprises between about 0.00001% and about 0.3% by weight of 3,3'-[1,4-Piperazinediylbis(butylene)]bis[1-[[[5-(4-chlorophenyl)-2-furan-yl]methylene]amino]-2,4-imidazolidinedione].

Point 92. The anhydrate form of any of Points 72-75, wherein the anhydrate comprises between 0.00001% and 0.3% by weight of 3,3'-[1,4-Piperazinediylbis(butylene)]bis[1-[[[5-(4-chlorophenyl)-2-furan-yl]methylene]amino]-2,4-imidazolidinedione].

Point 93. The anhydrate form of any of Points 72-75, wherein the anhydrate is substantially pure of 1-[[[5-(4-chlorophenyl)-2-furanyl]methylene]amino]-3-[4-(chloro)butyl]-2,-4-imidazolidinedione and 5-(4-chlorophenyl)-2-furancarboxaldehyde.

Point 94. The anhydrate form of any of Points 72-75, wherein the anhydrate comprises about 0.0025% or less of 1-[[[5-(4-chlorophenyl)-2-furanyl]methylene]amino]-3-[4-(chloro)butyl]-2,-4-imidazolidinedione and about 0.2% or less of 5-(4-chlorophenyl)-2-furancarboxaldehyde.

Point 95. The anhydrate form of any of Points 72-75, wherein the anhydrate comprises between about 0.0001% and about 0.0025% by weight of 1-[[[5-(4-chlorophenyl)-2-furanyl]methylene]amino]-3-[4-(chloro)butyl]-2,-4-imidazolidinedione and between about 0.00001% and about 0.2% by weight of 5-(4-chlorophenyl)-2-furancarboxaldehyde.

Point 96. The anhydrate form of any of Points 72-75, wherein the anhydrate comprises between 0.0001% and 0.0025% by weight of 1-[[[5-(4-chlorophenyl)-2-furanyl]methylene]amino]-3-[4-(chloro)butyl]-2,-4-imidazolidinedione and between about 0.00001% and 0.2% by weight of 5-(4-chlorophenyl)-2-furancarboxaldehyde.

Point 97. The anhydrate form of any of Points 72-75, wherein the anhydrate is substantially free/pure of 1-[[[5-(4-chlorophenyl)-2-furanyl]methylene]amino]-3-[4-(chloro)butyl]-2,-4-imidazolidinedione, 5-(4-chlorophenyl)-2-furancarboxaldehyde, 1,4-bis[4-[1-[[[5-(4-chlorophenyl)-2-furanyl]methylene]amino]-2,4-dioxo-3imidazolidinyl]butyl]-1-methylpiperazinium chloride, and 3,3'-[1,4-Piperazinediylbis(butylene)]bis[1-[[[5-(4-chlorophenyl)-2-furan-yl]methylene]amino]-2,4-imidazolidinedione].

Point 98. The anhydrate form of any of Points 72-75, wherein the anhydrate comprises about 0.0025% or less of 1-[[[5-(4-chlorophenyl)-2-furanyl]methylene]amino]-3-[4-(chloro)butyl]-2,-4-imidazolidinedione, about 0.2% or less of 5-(4-chlorophenyl)-2-furancarboxaldehyde, about 0.5% or less of 1,4-bis[4-[1-[[[5-(4-chlorophenyl)-2-furanyl]methylene]amino]-2,4-dioxo-3imidazolidinyl]butyl]-1-methylpiperazinium chloride, and about 0.3% or less of 3,3'-[1,4-Piperazinediylbis(butylene)]bis[1-[[[5-(4-chlorophenyl)-2-furan-yl]methylene]amino]-2,4-imidazolidinedione].

Point 99. The anhydrate form of any of Points 72-75, wherein the anhydrate comprises between about 0.0001% and about 0.0025% by weight of 1-[[[5-(4-chlorophenyl)-2-furanyl]methylene]amino]-3-[4-(chloro)butyl]-2,-4-imidazolidinedione, between about 0.00001% and about 0.2% by weight of 5-(4-chlorophenyl)-2-furancarboxaldehyde, between about 0.00001% and about 0.5% by weight of 1,4-bis[4-[1-[[[5-(4-chlorophenyl)-2-furanyl]methylene]amino]-2,4-dioxo-3imidazolidinyl]butyl]-1-methylpiperazinium chloride, and between about 0.00001% and about 0.3% by weight of 3,3'-[1,4-Piperazinediylbis(butylene)]bis[1-[[[5-(4-chlorophenyl)-2-furan-yl]methylene]amino]-2,4-imidazolidinedione].

Point 100. The anhydrate form of any of Points 72-75, wherein the anhydrate comprises between 0.0001% and 0.0025% by weight of 1-[[[5-(4-chlorophenyl)-2-furanyl]methylene]amino]-3-[4-(chloro)butyl]-2,-4-imidazolidinedione, between about 0.00001% and 0.2% by weight of 5-(4-chlorophenyl)-2-furancarboxaldehyde, between 0.00001% and 0.5% by weight of 1,4-bis[4-[1-[[[5-(4-chlorophenyl)-2-furanyl]methylene]amino]-2,4-dioxo-3imidazolidinyl]butyl]-1-methylpiperazinium chloride, and between 0.00001% and 0.3% by weight of 3,3'-[1,4-Piperazinediylbis(butylene)]bis[1-[[[5-(4-chlorophenyl)-2-furan-yl]methylene]amino]-2,4-imidazolidinedione].

Point 101. A method for preparing a hemi-hydrate form of (E)-1-[[[5-(4-chlorophenyl)-2-furanyl]methylene]amino]-3-[4-(4-methyl-1-piperazinyl)butyl]-2,4-imidazolidinedione or pharmaceutically acceptable salt thereof, wherein the method comprises:
(a) heating a mixture of water and (E)-1-[[[5-(4-chlorophenyl)-2-furanyl]methylene]amino]-3-[4-(4-methyl-1-piperazinyl)butyl]-2,4-imidazolidinedione to form a heated mixture;
(b) combining the heated mixture with acetone; and
(c) isolating the hemi-hydrate of (E)-1-[[[5-(4-chlorophenyl)-2-furanyl]methylene]amino]-3-[4-(4-methyl-1-piperazinyl)butyl]-2,4-imidazolidinedione.

Point 102. The method of Point 101, wherein the hemi-hydrate form is in hydrochloride salt form.

Point 103. The method of Point 101, wherein the hemi-hydrate form comprises between about 0.5% and about 2.5% (w/w) of water.

Point 104. The method of Point 101, wherein the hemi-hydrate form has an X-ray powder diffraction pattern comprising peaks at about 14.88+/−0.2 degrees 2 theta, at about 20.89+/−0.2 degrees 2 theta, and at about 26.03 degrees+/−0.2 degrees 2 theta.

Point 105. The method of Point 101, wherein the hemi-hydrate form comprises between about 0.5% and about 2.5% (w/w) of water and has an X-ray powder diffraction pattern comprising peaks at about 14.88+/−0.2 degrees 2 theta, at about 20.89+/−0.2 degrees 2 theta, and at about 26.03 degrees+/−0.2 degrees 2 theta.

Point 106. The method of Point 101, wherein the hemi-hydrate form is in hydrochloride salt form, comprises between about 0.5% and about 2.5% (w/w) of water, and has an X-ray powder diffraction pattern comprising peaks at about 14.88+/−0.2 degrees 2 theta, at about 20.89+/−0.2 degrees 2 theta, and at about 26.03 degrees+/−0.2 degrees 2 theta.

Point 107. The method of any of Points 101-106, wherein step (a) comprises heat the mixture to a temperature of about 60-80° C.

Point 108. The method of any of Points 101-106, wherein step (b) comprises combining the heated mixture with acetone, maintaining the mixture at a temperature of about 50° C., and then cooling the mixture to induce crystallization.

Point 109. The method of any of Points 101-106, wherein the hemi-hydrate is substantially pure of 1-[[[5-(4-chlorophenyl)-2-furanyl]methylene]amino]-3-[4-(chloro)butyl]-2,-4-imidazolidinedione.

Point 110. The method of any of Points 101-106, wherein the hemi-hydrate comprises about 0.0025% or less of 1-[[[5-(4-chlorophenyl)-2-furanyl]methylene]amino]-3-[4-(chloro)butyl]-2,-4-imidazolidinedione.

Point 111. The method of any of Points 101-106, wherein the hemi-hydrate comprises between about 0.0001% and about 0.0025% by weight of 1-[[[5-(4-chlorophenyl)-2-furanyl]methylene]amino]-3-[4-(chloro)butyl]-2,-4-imidazolidinedione.

Point 112. The method of any of Points 101-106, wherein the hemi-hydrate comprises between 0.0001% and 0.0025% by weight of 1-[[[5-(4-chlorophenyl)-2-furanyl]methylene]amino]-3-[4-(chloro)butyl]-2,-4-imidazolidinedione.

Point 113. The method of any of Points 101-106, wherein the hemi-hydrate is substantially pure of 5-(4-chlorophenyl)-2-furancarboxaldehyde.

Point 114. The method of any of Points 101-106, wherein the hemi-hydrate comprises about 0.2% or less of 5-(4-chlorophenyl)-2-furancarboxaldehyde.

Point 115. The method of any of Points 101-106, wherein the hemi-hydrate comprises between about 0.00001% and about 0.2% by weight of 5-(4-chlorophenyl)-2-furancarboxaldehyde.

Point 116. The method of any of Points 101-106, wherein the hemi-hydrate comprises between 0.00001% and 0.2% by weight of 5-(4-chlorophenyl)-2-furancarboxaldehyde.

Point 117. The method of any of Points 101-106, wherein the hemi-hydrate is substantially pure of 1,4-bis[4-[1-[[[5-(4-chlorophenyl)-2-furanyl]methylene]amino]-2,4-dioxo-3imidazolidinyl]butyl]-1-methylpiperazinium chloride.

Point 118. The method of any of Points 101-106, wherein the hemi-hydrate comprises about 0.5% or less of 1,4-bis[4-[1-[[[5-(4-chlorophenyl)-2-furanyl]methylene]amino]-2,4-dioxo-3imidazolidinyl]butyl]-1-methylpiperazinium chloride.

Point 119. The method of any of Points 101-106, wherein the hemi-hydrate comprises between about 0.00001% and about 0.5% by weight of 1,4-bis[4-[1-[[[5-(4-chlorophenyl)-2-furanyl]methylene]amino]-2,4-dioxo-3imidazolidinyl]butyl]-1-methylpiperazinium chloride.

Point 120. The method of any of Points 101-106, wherein the hemi-hydrate comprises between 0.00001% and 0.5% by weight of 1,4-bis[4-[1-[[[5-(4-chlorophenyl)-2-furanyl]methylene]amino]-2,4-dioxo-3imidazolidinyl]butyl]-1-methylpiperazinium chloride.

Point 121. The method of any of Points 101-106, wherein the hemi-hydrate comprises between 0.00001% and 0.4% by weight of 1,4-bis[4-[1-[[[5-(4-chlorophenyl)-2-furanyl]methylene]amino]-2,4-diox-o-3-imidazolidinyl]butyl]-1-methylpiperazinium chloride.

Point 122. The method of any of Points 101-106, wherein the hemi-hydrate is substantially free/pure of 3,3'-[1,4-Piperazinediylbis(butylene)]bis[1-[[[5-(4-chlorophenyl)-2-furan-yl]methylene]amino]-2,4-imidazolidinedione].

Point 123. The method of any of Points 101-106, wherein the hemi-hydrate comprises about 0.3 or less of 3,3'-[1,4-Piperazinediylbis(butylene)]bis[1-[[[5-(4-chlorophenyl)-2-furan-yl]methylene]amino]-2,4-imidazolidinedione].

Point 124. The method of any of Points 101-106, wherein the hemi-hydrate comprises between about 0.00001% and about 0.3% by weight of 3,3'-[1,4-Piperazinediylbis(butylene)]bis[1-[[[5-(4-chlorophenyl)-2-furan-yl]methylene]amino]-2,4-imidazolidinedione].

Point 125. The method of any of Points 101-106, wherein the hemi-hydrate comprises between 0.00001% and 0.3% by weight of 3,3'-[1,4-Piperazinediylbis(butylene)]bis[1-[[[5-(4-chlorophenyl)-2-furan-yl]methylene]amino]-2,4-imidazolidinedione].

Point 126. The method of any of Points 101-106, wherein the hemi-hydrate is substantially pure of 1-[[[5-(4-chlorophenyl)-2-furanyl]methylene]amino]-3-[4-(chloro)butyl]-2,-4-imidazolidinedione and 5-(4-chlorophenyl)-2-furancarboxaldehyde.

Point 127. The method of any of Points 101-106, wherein the hemi-hydrate comprises about 0.0025% or less of 1-[[[5-(4-chlorophenyl)-2-furanyl]methylene]amino]-3-[4-(chloro)butyl]-2,-4-imidazolidinedione and about 0.2% or less of 5-(4-chlorophenyl)-2-furancarboxaldehyde.

Point 128. The method of any of Points 101-106, wherein the hemi-hydrate comprises between about 0.0001% and about 0.0025% by weight of 1-[[[5-(4-chlorophenyl)-2-furanyl]methylene]amino]-3-[4-(chloro)butyl]-2,-4-imidazolidinedione and between about 0.00001% and about 0.2% by weight of 5-(4-chlorophenyl)-2-furancarboxaldehyde.

Point 129. The method of any of Points 101-106, wherein the hemi-hydrate comprises between 0.0001% and 0.0025% by weight of 1-[[[5-(4-chlorophenyl)-2-furanyl]methylene]amino]-3-[4-(chloro)butyl]-2,-4-imidazolidinedione and between about 0.00001% and 0.2% by weight of 5-(4-chlorophenyl)-2-furancarboxaldehyde.

Point 130. The method of any of Points 101-106, wherein the hemi-hydrate is substantially free/pure of 1-[[[5-(4-chlorophenyl)-2-furanyl]methylene]amino]-3-[4-(chloro)butyl]-2,-4-imidazolidinedione, 5-(4-chlorophenyl)-2-furancarboxaldehyde, 1,4-bis[4-[1-[[[5-(4-chlorophenyl)-2-furanyl]methylene]amino]-2,4-dioxo-3imidazolidinyl]butyl]-1-methylpiperazinium chloride, and 3,3'-[1,4-Piperazinediylbis(butylene)]bis[1-[[[5-(4-chlorophenyl)-2-furan-yl]methylene]amino]-2,4-imidazolidinedione].

Point 131. The method of any of Points 101-106, wherein the hemi-hydrate comprises about 0.0025% or less of 1-[[[5-(4-chlorophenyl)-2-furanyl]methylene]amino]-3-[4-(chloro)butyl]-2,-4-imidazolidinedione, about 0.2% or less of 5-(4-chlorophenyl)-2-furancarboxaldehyde, about 0.5% or less of 1,4-bis[4-[1-[[[5-(4-chlorophenyl)-2-furanyl]methylene]amino]-2,4-dioxo-3imidazolidinyl]butyl]-1-methylpiperazinium chloride, and about 0.3% or less of 3,3'-[1,4-Piperazinediylbis(butylene)]bis[1-[[[5-(4-chlorophenyl)-2-furan-yl]methylene]amino]-2,4-imidazolidinedione].

Point 132. The method of any of Points 101-106, wherein the hemi-hydrate comprises between about 0.0001% and about 0.0025% by weight of 1-[[[5-(4-chlorophenyl)-2-furanyl]methylene]amino]-3-[4-(chloro)butyl]-2,-4-imidazolidinedione, between about 0.00001% and about 0.2% by weight of 5-(4-chlorophenyl)-2-furancarboxaldehyde, between about 0.00001% and about 0.5% by weight of 1,4-bis[4-[1-[[[5-(4-chlorophenyl)-2-furanyl]methylene]amino]-2,4-dioxo-3imidazolidinyl]butyl]-1-methylpiperazinium chloride, and between about 0.00001% and about 0.3% by weight of 3,3'-[1,4-Piperazinediylbis(butylene)]bis[1-[[[5-(4-chlorophenyl)-2-furan-yl]methylene]amino]-2,4-imidazolidinedione].

Point 133. The method of any of Points 101-106, wherein the hemi-hydrate comprises between 0.0001% and 0.0025% by weight of 1-[[[5-(4-chlorophenyl)-2-furanyl]methylene]amino]-3-[4-(chloro)butyl]-2,-4-imidazolidinedione, between about 0.00001% and 0.2% by weight of 5-(4-chlorophenyl)-2-furancarboxaldehyde, between 0.00001% and 0.5% by weight of 1,4-bis[4-[1-[[[5-(4-chlorophenyl)-2-furanyl]methylene]amino]-2,4-dioxo-3imidazolidinyl]butyl]-1-methylpiperazinium chloride, and between 0.00001% and 0.3% by weight of 3,3'-[1,4-Piperazinediylbis(butylene)]bis[1-[[[5-(4-chlorophenyl)-2-furan-yl]methylene]amino]-2,4-imidazolidinedione].

Point 134. A hemi-hydrate form of (E)-1-[[[5-(4-chlorophenyl)-2-furanyl]methylene]amino]-3-[4-(4-methyl-1-piperazinyl)butyl]-2,4-imidazolidinedione or pharmaceutically acceptable salt thereof.

Point 135. The hemi-hydrate form of Point 134, wherein the hemi-hydrate form comprises between about 0.5% and about 2.5% (w/w) of water.

Point 136. The hemi-hydrate form of Point 134, wherein the hemi-hydrate form is in the form of a hydrochloride salt.

Point 137. The hemi-hydrate form of Point 134, wherein the hemi-hydrate form has an X-ray powder diffraction pattern comprising peaks at about 14.88+/−0.2 degrees 2 theta and at about 20.89+/−0.2 degrees 2 theta.

Point 138. The hemi-hydrate form of Point 134, wherein the hemi-hydrate form has an X-ray powder diffraction pattern comprising peaks at about 14.88+/−0.2 degrees 2 theta, at about 20.89+/−0.2 degrees 2 theta, and at about 26.03 degrees+/−0.2 degrees 2 theta.

Point 139. The hemi-hydrate form of Point 134, wherein the hemi-hydrate form has an infrared (IR) absorption spectrum having a characteristic IR absorption peak at about 3450.

Point 140. The hemi-hydrate form of Point 134, wherein the hemi-hydrate form has an IR absorption spectrum having a characteristic IR absorption peak at about 3512.

Point 141. The hemi-hydrate form of Point 134, wherein the hemi-hydrate form has an IR absorption spectrum having a characteristic IR absorption peaks at about 3450 and at about 3512.

Point 142. The hemi-hydrate form of Points 134 wherein the hydrate-form is substantially pure of isopropanol solvate and anhydrate forms of (E)-1-[[[5-(4-chlorophenyl)-2-furanyl]methylene]amino]-3-[4-(4-methyl-1-piperazinyl)butyl]-2,4-imidazolidinedione.

Point 143. The hemi-hydrate form of Point 134, wherein the hemi-hydrate form wherein the hemi-hydrate form comprises between about 0.5% and about 2.5% (w/w) of water and has an X-ray powder diffraction pattern comprising peaks at about 14.88+/−0.2 degrees 2 theta and at about 20.89+/−0.2 degrees 2 theta.

Point 144. The hemi-hydrate form of Point 134, wherein the hemi-hydrate form wherein the hemi-hydrate form comprises between about 0.5% and about 2.5% (w/w) of water, has an X-ray powder diffraction pattern comprising peaks at about 14.88+/−0.2 degrees 2 theta and at about 20.89+/−0.2 degrees 2 theta, and is substantially pure of isopropanol solvate and anhydrate forms of (E)-1-[[[5-(4-chlorophenyl)-2-furanyl]methylene]amino]-3-[4-(4-methyl-1-piperazinyl)butyl]-2,4-imidazolidinedione.

Point 145. The hemi-hydrate form of Point 134, wherein the hemi-hydrate form is in hydrochloride salt form, comprises between about 0.5% and about 2.5% (w/w) of water, and has an X-ray powder diffraction pattern comprising peaks at about 14.88+/−0.2 degrees 2 theta and at about 20.89+/−0.2 degrees 2 theta.

Point 146. The hemi-hydrate form of Point 134, wherein the hemi-hydrate form is in hydrochloride salt form, comprises between about 0.5% and about 2.5% (w/w) of water, has an X-ray powder diffraction pattern comprising peaks at about 14.88+/−0.2 degrees 2 theta and at about 20.89+/−0.2 degrees 2 theta, and is substantially pure of isopropanol solvate and anhydrate forms of (E)-1-[[[5-(4-chlorophenyl)-2-furanyl]methylene]amino]-3-[4-(4-methyl-1-piperazinyl)butyl]-2,4-imidazolidinedione.

Point 147. The hemi-hydrate form of any of Points 134-146, wherein the hemi-hydrate form is substantially pure of 1-[[[5-(4-chlorophenyl)-2-furanyl]methylene]amino]-3-[4-(chloro)butyl]-2,-4-imidazolidinedione.

Point 148. The hemi-hydrate form of any of Points 134-146, wherein the hemi-hydrate comprises about 0.0025% or less of 1-[[[5-(4-chlorophenyl)-2-furanyl]methylene]amino]-3-[4-(chloro)butyl]-2,-4-imidazolidinedione.

Point 149. The hemi-hydrate form of any of Points 134-146, wherein the hemi-hydrate comprises between about 0.0001% and about 0.0025% by weight of 1-[[[5-(4-chlorophenyl)-2-furanyl]methylene]amino]-3-[4-(chloro)butyl]-2,-4-imidazolidinedione.

Point 150. The hemi-hydrate form of any of Points 134-146, wherein the hemi-hydrate comprises between 0.0001% and 0.0025% by weight of 1-[[[5-(4-chlorophenyl)-2-furanyl]methylene]amino]-3-[4-(chloro)butyl]-2,-4-imidazolidinedione.

Point 151. The hemi-hydrate form of any of Points 134-146, wherein the hemi-hydrate is substantially pure of 5-(4-chlorophenyl)-2-furancarboxaldehyde.

Point 152. The hemi-hydrate form of any of Points 134-146, wherein the hemi-hydrate comprises about 0.2% or less of 5-(4-chlorophenyl)-2-furancarboxaldehyde.

Point 153. The hemi-hydrate form of any of Points 134-146, wherein the hemi-hydrate comprises between about 0.00001% and about 0.2% by weight of 5-(4-chlorophenyl)-2-furancarboxaldehyde.

Point 154. The hemi-hydrate form of any of Points 134-146, wherein the hemi-hydrate comprises between 0.00001% and 0.2% by weight of 5-(4-chlorophenyl)-2-furancarboxaldehyde.

Point 155. The hemi-hydrate form of any of Points 134-146, wherein the hemi-hydrate is substantially pure of 1,4-bis[4-[1-[[[5-(4-chlorophenyl)-2-furanyl]methylene]amino]-2,4-dioxo-3imidazolidinyl]butyl]-1-methylpiperazinium chloride.

Point 156. The hemi-hydrate form of any of Points 134-146, wherein the hemi-hydrate comprises about 0.5% or less of 1,4-bis[4-[1-[[[5-(4-chlorophenyl)-2-furanyl]methylene]amino]-2,4-dioxo-3imidazolidinyl]butyl]-1-methylpiperazinium chloride.

Point 157. The hemi-hydrate form of any of Points 134-146, wherein the hemi-hydrate comprises between about 0.00001% and about 0.5% by weight of 1,4-bis[4-[1-[[[5-(4-chlorophenyl)-2-furanyl]methylene]amino]-2,4-dioxo-3imidazolidinyl]butyl]-1-methylpiperazinium chloride.

Point 158. The hemi-hydrate form of any of Points 134-146, wherein the hemi-hydrate comprises between 0.00001% and 0.5% by weight of 1,4-bis[4-[1-[[[5-(4-chlorophenyl)-2-furanyl]methylene]amino]-2,4-dioxo-3imidazolidinyl]butyl]-1-methylpiperazinium chloride.

Point 159. The hemi-hydrate form of any of Points 134-146, wherein the hemi-hydrate comprises between 0.00001% and 0.4% by weight of 1,4-bis[4-[1-[[[5-(4-chlorophenyl)-2-furanyl]methylene]amino]-2,4-diox-o-3-imidazolidinyl]butyl]-1-methylpiperazinium chloride.

Point 160. The hemi-hydrate form of any of Points 134-146, wherein the hemi-hydrate is substantially free/pure of 3,3'-[1,4-Piperazinediylbis(butylene)]bis[1-[[[5-(4-chlorophenyl)-2-furan-yl]methylene]amino]-2,4-imidazolidinedione].

Point 161. The hemi-hydrate form of any of Points 134-146, wherein the hemi-hydrate comprises about 0.3% or less of 3,3'-[1,4-Piperazinediylbis(butylene)]bis[1-[[[5-(4-chlorophenyl)-2-furan-yl]methylene]amino]-2,4-imidazolidinedione].

Point 162. The hemi-hydrate form of any of Points 134-146, wherein the hemi-hydrate comprises between about 0.00001% and about 0.3% by weight of 3,3'-[1,4-Piperazinediylbis(butylene)]bis[1-[[[5-(4-chlorophenyl)-2-furan-yl]methylene]amino]-2,4-imidazolidinedione].

Point 163. The hemi-hydrate form of any of Points 134-146, wherein the hemi-hydrate comprises between 0.00001% and 0.3% by weight of 3,3'-[1,4-Piperazinediylbis(butylene)]bis[1-[[[5-(4-chlorophenyl)-2-furan-yl]methylene]amino]-2,4-imidazolidinedione].

Point 164. The hemi-hydrate form of any of Points 134-146, wherein the hemi-hydrate is substantially pure of 1-[[[5-(4-chlorophenyl)-2-furanyl]methylene]amino]-3-[4-(chloro)butyl]-2,-4-imidazolidinedione and 5-(4-chlorophenyl)-2-furancarboxaldehyde.

Point 165. The hemi-hydrate form of any of Points 134-146, wherein the hemi-hydrate comprises about 0.0025% or less of 1-[[[5-(4-chlorophenyl)-2-furanyl]methylene]amino]-3-[4-(chloro)butyl]-2,-4-imidazolidinedione and about 0.2% or less of 5-(4-chlorophenyl)-2-furancarboxaldehyde.

Point 166. The hemi-hydrate form of any of Points 134-146, wherein the hemi-hydrate comprises between about 0.0001% and about 0.0025% by weight of 1-[[[5-(4-chlorophenyl)-2-furanyl]methylene]amino]-3-[4-(chloro)butyl]-2,-4-imidazolidinedione and between about 0.00001% and about 0.2% by weight of 5-(4-chlorophenyl)-2-furancarboxaldehyde.

Point 167. The hemi-hydrate form of any of Points 134-146, wherein the hemi-hydrate comprises between 0.0001% and 0.0025% by weight of 1-[[[5-(4-chlorophenyl)-2-furanyl]methylene]amino]-3-[4-(chloro)butyl]-2,-4-imidazolidinedione and between about 0.00001% and 0.2% by weight of 5-(4-chlorophenyl)-2-furancarboxaldehyde.

Point 168. The hemi-hydrate form of any of Points 134-146, wherein the hemi-hydrate is substantially free/pure of 1-[[[5-(4-chlorophenyl)-2-furanyl]methylene]amino]-3-[4-(chloro)butyl]-2,4-imidazolidinedione, 5-(4-chlorophenyl)-2-furancarboxaldehyde, 1,4-bis[4-[1-[[[5-(4-chlorophenyl)-2-furanyl]methylene]amino]-2,4-dioxo-3imidazolidinyl]butyl]-1-methylpiperazinium chloride, and 3,3'-[1,4-Piperazinediylbis(butylene)]bis[1-[[[5-(4-chlorophenyl)-2-furan-yl]methylene]amino]-2,4-imidazolidinedione].

Point 169. The hemi-hydrate form of any of Points 134-146, wherein the hemi-hydrate comprises about 0.0025% or less of 1-[[[5-(4-chlorophenyl)-2-furanyl]methylene]amino]-3-[4-(chloro)butyl]-2,-4-imidazolidinedione, about 0.2% or less of 5-(4-chlorophenyl)-2-furancarboxaldehyde, about 0.5% or less of 1,4-bis[4-[1-[[[5-(4-chlorophenyl)-2-furanyl]methylene]amino]-2,4-dioxo-3imidazolidinyl]butyl]-1-methylpiperazinium chloride, and about 0.3% or less of 3,3'-[1,4-Piperazinediylbis(butylene)]bis[1-[[[5-(4-chlorophenyl)-2-furan-yl]methylene]amino]-2,4-imidazolidinedione].

Point 170. The hemi-hydrate form of any of Points 134-146, wherein the hemi-hydrate comprises between about 0.0001% and about 0.0025% by weight of 1-[[[5-(4-chlorophenyl)-2-furanyl]methylene]amino]-3-[4-(chloro)butyl]-2,-4-imidazolidinedione, between about 0.00001% and about 0.2% by weight of 5-(4-chlorophenyl)-2-furancarboxaldehyde, between about 0.00001% and about 0.5% by weight of 1,4-bis[4-[1-[[[5-(4-chlorophenyl)-2-furanyl]methylene]amino]-2,4-dioxo-3imidazolidinyl]butyl]-1-methylpiperazinium chloride, and between about 0.00001% and about 0.3% by weight of 3,3'-[1,4-Piperazinediylbis(butylene)]bis[1-[[[5-(4-chlorophenyl)-2-furan-yl]methylene]amino]-2,4-imidazolidinedione].

Point 171. The hemi-hydrate form of any of Points 134-146, wherein the hemi-hydrate comprises between 0.0001% and 0.0025% by weight of 1-[[[5-(4-chlorophenyl)-2-furanyl]methylene]amino]-3-[4-(chloro)butyl]-2,-4-imidazolidinedione, between about 0.00001% and 0.2% by weight of 5-(4-chlorophenyl)-2-furancarboxaldehyde, between 0.00001% and 0.5% by weight of 1,4-bis[4-[1-[[[5-(4-chlorophenyl)-2-furanyl]methylene]amino]-2,4-dioxo-3imidazolidinyl]butyl]-1-methylpiperazinium chloride, and between 0.00001% and 0.3% by weight of 3,3'-[1,4-Piperazinediylbis(butylene)]bis[1-[[[5-(4-chlorophenyl)-2-furan-yl]methylene]amino]-2,4-imidazolidinedione].

Point 172. An oral pharmaceutical composition consisting of one or more pharmaceutically acceptable carriers and/or excipients and about 50-175 mg of an active ingredient that comprises, consists essentially of, or even consists of a hemi-hydrate form of (E)-1-[[[5-(4-chlorophenyl)-2-furanyl]methylene]amino]-3-[4-(4-methyl-1-piperazinyl)butyl]-2,4-imidazolidinedione or pharmaceutically acceptable salt thereof.

Point 173. The pharmaceutical composition of Point 172, the hemi-hydrate form comprises between about 0.5% and about 2.5% (w/w) of water.

Point 174. The pharmaceutical composition of Point 172, wherein the hemi-hydrate form is in the form of a hydrochloride salt.

Point 175. The pharmaceutical composition of Point 172, wherein the hemi-hydrate form has an X-ray powder diffraction pattern comprising peaks at about 14.88+/−0.2 degrees 2 theta and at about 20.89+/−0.2 degrees 2 theta.

Point 176. The pharmaceutical composition of Point 172, wherein the hemi-hydrate form has an X-ray powder diffraction pattern comprising peaks at about 14.88+/−0.2 degrees 2 theta, at about 20.89+/−0.2 degrees 2 theta, and at about 26.03 degrees+/−0.2 degrees 2 theta.

Point 177. The pharmaceutical composition of Point 172, wherein the hemi-hydrate form has an infrared (IR) absorption spectrum having a characteristic IR absorption peak at about 3450.

Point 178. The pharmaceutical composition of Point 172, wherein the hemi-hydrate form has an IR absorption spectrum having a characteristic IR absorption peak at about 3512.

Point 179. The pharmaceutical composition of Point 172, wherein the hemi-hydrate form has an IR absorption spectrum having a characteristic IR absorption peaks at about 3450 and at about 3512.

Point 180. The pharmaceutical composition of Point 172, wherein the hydrate-form is substantially pure of isopropanol solvate and anhydrate forms of (E)-1-[[[5-(4-chlorophenyl)-2-furanyl]methylene]amino]-3-[4-(4-methyl-1-piperazinyl)butyl]-2,4-imidazolidinedione.

Point 181. The pharmaceutical composition of Point 172, wherein the hemi-hydrate form wherein the hemi-hydrate form comprises between about 0.5% and about 2.5% (w/w) of water and has an X-ray powder diffraction pattern comprising peaks at about 14.88+/−0.2 degrees 2 theta and at about 20.89+/−0.2 degrees 2 theta.

Point 182. The pharmaceutical composition of Point 172, wherein the hemi-hydrate form wherein the hemi-hydrate form comprises between about 0.5% and about 2.5% (w/w) of water, has an X-ray powder diffraction pattern comprising peaks at about 14.88+/−0.2 degrees 2 theta and at about 20.89+/−0.2 degrees 2 theta, and is substantially pure of isopropanol solvate and anhydrate forms of (E)-1-[[[5-(4-chlorophenyl)-2-furanyl]methylene]amino]-3-[4-(4-methyl-1-piperazinyl)butyl]-2,4-imidazolidinedione.

Point 183. The pharmaceutical composition of Point 172, wherein the hemi-hydrate form is in hydrochloride salt form, comprises between about 0.5% and about 2.5% (w/w) of water, and has an X-ray powder diffraction pattern comprising peaks at about 14.88+/−0.2 degrees 2 theta and at about 20.89+/−0.2 degrees 2 theta.

Point 184. The pharmaceutical composition of Point 172, wherein the hemi-hydrate form is in hydrochloride salt form, comprises between about 0.5% and about 2.5% (w/w) of water, has an X-ray powder diffraction pattern comprising peaks at about 14.88+/−0.2 degrees 2 theta and at about 20.89+/−0.2 degrees 2 theta, and is substantially pure of isopropanol solvate and anhydrate forms of (E)-1-[[[5-(4-chlorophenyl)-2-furanyl]methylene]amino]-3-[4-(4-methyl-1-piperazinyl)butyl]-2,4-imidazolidinedione.

Point 185. The pharmaceutical composition of any of Points 172-184, wherein the hemi-hydrate form is substantially pure of 1-[[[5-(4-chlorophenyl)-2-furanyl]methylene]amino]-3-[4-(chloro)butyl]-2,-4-imidazolidinedione.

Point 186. The pharmaceutical composition of any of Points 172-184, wherein the hemi-hydrate comprises about 0.0025% or less of 1-[[[5-(4-chlorophenyl)-2-furanyl]methylene]amino]-3-[4-(chloro)butyl]-2,-4-imidazolidinedione.

Point 187. The pharmaceutical composition of any of Points 172-184, wherein the hemi-hydrate comprises between about 0.0001% and about 0.0025% by weight of 1-[[[5-(4-chlorophenyl)-2-furanyl]methylene]amino]-3-[4-(chloro)butyl]-2,-4-imidazolidinedione.

Point 188. The pharmaceutical composition of any of Points 172-184, wherein the hemi-hydrate comprises between 0.0001% and 0.0025% by weight of 1-[[[5-(4-chlorophenyl)-2-furanyl]methylene]amino]-3-[4-(chloro)butyl]-2,-4-imidazolidinedione.

Point 189. The pharmaceutical composition of any of Points 172-184, wherein the hemi-hydrate is substantially pure of 5-(4-chlorophenyl)-2-furancarboxaldehyde.

Point 190. The pharmaceutical composition of any of Points 172-184, wherein the hemi-hydrate comprises about 0.2% or less of 5-(4-chlorophenyl)-2-furancarboxaldehyde.

Point 191. The pharmaceutical composition of any of Points 172-184, wherein the hemi-hydrate comprises between about 0.00001% and about 0.2% by weight of 5-(4-chlorophenyl)-2-furancarboxaldehyde.

Point 192. The pharmaceutical composition of any of Points 172-184, wherein the hemi-hydrate comprises between 0.00001% and 0.2% by weight of 5-(4-chlorophenyl)-2-furancarboxaldehyde.

Point 193. The pharmaceutical composition of any of Points 172-184, wherein the hemi-hydrate is substantially pure of 1,4-bis[4-[1-[[[5-(4-chlorophenyl)-2-furanyl]methylene]amino]-2,4-dioxo-3imidazolidinyl]butyl]-1-methylpiperazinium chloride.

Point 194. The pharmaceutical composition of any of Points 172-184, wherein the hemi-hydrate comprises about 0.5% or less of 1,4-bis[4-[1-[[[5-(4-chlorophenyl)-2-furanyl]methylene]amino]-2,4-dioxo-3imidazolidinyl]butyl]-1-methylpiperazinium chloride.

Point 195. The pharmaceutical composition of any of Points 172-184, wherein the hemi-hydrate comprises between about 0.00001% and about 0.5% by weight of 1,4-bis[4-[1-[[[5-(4-chlorophenyl)-2-furanyl]methylene]amino]-2,4-dioxo-3imidazolidinyl]butyl]-1-methylpiperazinium chloride.

Point 196. The pharmaceutical composition of any of Points 172-184, wherein the hemi-hydrate comprises between 0.00001% and 0.5% by weight of 1,4-bis[4-[1-[[[5-(4-chlorophenyl)-2-furanyl]methylene]amino]-2,4-dioxo-3imidazolidinyl]butyl]-1-methylpiperazinium chloride.

Point 197. The pharmaceutical composition of any of Points 172-184, wherein the hemi-hydrate comprises between 0.00001% and 0.4% by weight of 1,4-bis[4-[1-[[[5-(4-chlorophenyl)-2-furanyl]methylene]amino]-2,4-diox-o-3-imidazolidinyl]butyl]-1-methylpiperazinium chloride.

Point 198. The pharmaceutical composition of any of Points 172-184, wherein the hemi-hydrate is substantially free/pure of 3,3'-[1,4-Piperazinediylbis(butylene)]bis[1-[[[5-(4-chlorophenyl)-2-furan-yl]methylene]amino]-2,4-imidazolidinedione].

Point 199. The pharmaceutical composition of any of Points 172-184, wherein the hemi-hydrate comprises about 0.3% or less of 3,3'-[1,4-Piperazinediylbis(butylene)]bis[1-[[[5-(4-chlorophenyl)-2-furan-yl]methylene]amino]-2,4-imidazolidinedione].

Point 200. The pharmaceutical composition of any of Points 172-184, wherein the hemi-hydrate comprises between about 0.00001% and about 0.3% by weight of 3,3'-[1,4-Piperazinediylbis(butylene)]bis[1-[[[5-(4-chlorophenyl)-2-furan-yl]methylene]amino]-2,4-imidazolidinedione].

Point 201. The pharmaceutical composition of any of Points 172-184, wherein the hemi-hydrate comprises between 0.00001% and 0.3% by weight of 3,3'-[1,4-Piperazinediylbis(butylene)]bis[1-[[[5-(4-chlorophenyl)-2-furan-yl]methylene]amino]-2,4-imidazolidinedione].

Point 202. The pharmaceutical composition of any of Points 172-184, wherein the hemi-hydrate is substantially pure of 1-[[[5-(4-chlorophenyl)-2-furanyl]methylene]amino]-3-[4-(chloro)butyl]-2,-4-imidazolidinedione and 5-(4-chlorophenyl)-2-furancarboxaldehyde.

Point 203. The pharmaceutical composition of any of Points 172-184, wherein the hemi-hydrate comprises about 0.0025% or less of 1-[[[5-(4-chlorophenyl)-2-furanyl]methylene]amino]-3-[4-(chloro)butyl]-2,-4-imidazolidinedione and about 0.2% or less of 5-(4-chlorophenyl)-2-furancarboxaldehyde.

Point 204. The pharmaceutical composition of any of Points 172-184, wherein the hemi-hydrate comprises between about 0.0001% and about 0.0025% by weight of 1-[[[5-(4-chlorophenyl)-2-furanyl]methylene]amino]-3-[4-(chloro)butyl]-2,-4-imidazolidinedione and between about 0.00001% and about 0.2% by weight of 5-(4-chlorophenyl)-2-furancarboxaldehyde.

Point 205. The pharmaceutical composition of any of Points 172-184, wherein the hemi-hydrate comprises between 0.0001% and 0.0025% by weight of 1-[[[5-(4-chlorophenyl)-2-furanyl]methylene]amino]-3-[4-(chloro)butyl]-2,-4-imidazolidinedione and between about 0.00001% and 0.2% by weight of 5-(4-chlorophenyl)-2-furancarboxaldehyde.

Point 206. The pharmaceutical composition of any of Points 172-184, wherein the hemi-hydrate is substantially free/pure of 1-[[[5-(4-chlorophenyl)-2-furanyl]methylene]amino]-3-[4-(chloro)butyl]-2,-4-imidazolidinedione, 5-(4-chlorophenyl)-2-furancarboxaldehyde, 1,4-bis[4-[1-[[[5-(4-chlorophenyl)-2-furanyl]methylene]amino]-2,4-dioxo-3imidazolidinyl]butyl]-1-methylpiperazinium chloride, and 3,3'-[1,4-Piperazinediylbis(butylene)]bis[1-[[[5-(4-chlorophenyl)-2-furan-yl]methylene]amino]-2,4-imidazolidinedione].

Point 207. The pharmaceutical composition of any of Points 172-184, wherein the hemi-hydrate comprises about 0.0025% or less of 1-[[[5-(4-chlorophenyl)-2-furanyl]methylene]amino]-3-[4-(chloro)butyl]-2,-4-imidazolidinedione, about 0.2% or less of 5-(4-chlorophenyl)-2-furancarboxaldehyde, about 0.5% or less of 1,4-bis[4-[1-[[[5-(4-chlorophenyl)-2-furanyl]methylene]amino]-2,4-dioxo-3imidazolidinyl]butyl]-1-methylpiperazinium chloride, and about 0.3% or less of 3,3'-[1,4-Piperazinediylbis(butylene)]bis[1-[[[5-(4-chlorophenyl)-2-furan-yl]methylene]amino]-2,4-imidazolidinedione].

Point 208. The pharmaceutical composition of any of Points 172-184, wherein the hemi-hydrate comprises between about 0.0001% and about 0.0025% by weight of 1-[[[5-(4-chlorophenyl)-2-furanyl]methylene]amino]-3-[4-(chloro)butyl]-2,-4-imidazolidinedione, between about 0.00001% and about 0.2% by weight of 5-(4-chlorophenyl)-2-furancarboxaldehyde, between about 0.00001% and about 0.5% by weight of 1,4-bis[4-[1-[[[5-(4-chlorophenyl)-2-furanyl]methylene]amino]-2,4-dioxo-3imidazolidinyl]butyl]-1-methylpiperazinium chloride, and between about 0.00001% and about 0.3% by weight of 3,3'-[1,4-Piperazinediylbis(butylene)]bis[1-[[[5-(4-chlorophenyl)-2-furan-yl]methylene]amino]-2,4-imidazolidinedione].

Point 209. The pharmaceutical composition of any of Points 172-184, wherein the hemi-hydrate comprises between 0.0001% and 0.0025% by weight of 1-[[[5-(4-chlorophenyl)-2-furanyl]methylene]amino]-3-[4-(chloro)butyl]-2,-4-imidazolidinedione, between about 0.00001% and 0.2% by weight of 5-(4-chlorophenyl)-2-furancarboxaldehyde, between 0.00001% and 0.5% by weight of 1,4-bis[4-[1-[[[5-(4-chlorophenyl)-2-furanyl]methylene]amino]-2,4-dioxo-3imidazolidinyl]butyl]-1-methylpiperazinium chloride, and between 0.00001% and 0.3% by weight of 3,3'-[1,4-Piperazinediylbis(butylene)]bis[1-[[[5-(4-chlorophenyl)-2-furan-yl]methylene]amino]-2,4-imidazolidinedione].

Point 210. A method of treating or preventing cardiac arrhythmias, comprising identifying a human in need of treatment and administering to the patient an oral dosage form comprising one or more pharmaceutically acceptable carriers and/or excipients and about 50-175 mg of an active ingredient that comprises, consists essentially of, or even consists of a hemi-hydrate form of (E)-1-[[[5-(4-chlorophenyl)-2-furanyl]methylene]amino]-3-[4-(4-methyl-1-piperazinyl)butyl]-2,4-imidazolidinedione or pharmaceutically acceptable salt thereof.

Point 211. The method of Point 210, the hemi-hydrate form comprises between about 0.5% and about 2.5% (w/w) of water.

Point 212. The method of Point 210, wherein the hemi-hydrate form is in the form of a hydrochloride salt.

Point 213. The method of Point 210, wherein the hemi-hydrate form has an X-ray powder diffraction pattern comprising peaks at about 14.88+/−0.2 degrees 2 theta and at about 20.89+/−0.2 degrees 2 theta.

Point 214. The method of Point 210, wherein the hemi-hydrate form has an X-ray powder diffraction pattern comprising peaks at about 14.88+/−0.2 degrees 2 theta and at about 20.89+/−0.2 degrees 2 theta, and at about 26.03 degrees+/−0.2 degrees 2 theta.

Point 215. The method of Point 210, wherein the hemi-hydrate form has an infrared (IR) absorption spectrum having a characteristic IR absorption peak at about 3450.

Point 216. The method of Point 210, wherein the hemi-hydrate form has an IR absorption spectrum having a characteristic IR absorption peak at about 3512.

Point 217. The method of Point 210, wherein the hemi-hydrate form has an IR absorption spectrum having a characteristic IR absorption peaks at about 3450 and at about 3512.

Point 218. The method of Point 210, wherein the hydrate-form is substantially pure of isopropanol solvate and anhydrate forms of (E)-1-[[[5-(4-chlorophenyl)-2-furanyl]methylene]amino]-3-[4-(4-methyl-1-piperazinyl)butyl]-2,4-imidazolidinedione.

Point 219. The method of Point 210, wherein the hemi-hydrate form wherein the hemi-hydrate form comprises between about 0.5% and about 2.5% (w/w) of water and has an X-ray powder diffraction pattern comprising peaks at about 14.88+/−0.2 degrees 2 theta and at about 20.89+/−0.2 degrees 2 theta.

Point 220. The method of Point 210, wherein the hemi-hydrate form comprises between about 0.5% and about 2.5% (w/w) of water, has an X-ray powder diffraction pattern comprising peaks at about 14.88+/−0.2 degrees 2 theta and at about 20.89+/−0.2 degrees 2 theta, and is substantially pure of isopropanol solvate and anhydrate forms of (E)-1-[[[5-(4-chlorophenyl)-2-furanyl]methylene]amino]-3-[4-(4-methyl-1-piperazinyl)butyl]-2,4-imidazolidinedione.

Point 221. The method of Point 210, wherein the hemi-hydrate form is in hydrochloride salt form, comprises between about 0.5% and about 2.5% (w/w) of water, and has an X-ray powder diffraction pattern comprising peaks at about 14.88+/−0.2 degrees 2 theta and at about 20.89+/−0.2 degrees 2 theta.

Point 222. The method of Point 210, wherein the hemi-hydrate form is in hydrochloride salt form, comprises between about 0.5% and about 2.5% (w/w) of water, has an X-ray powder diffraction pattern comprising peaks at about 14.88+/−0.2 degrees 2 theta and at about 20.89+/−0.2 degrees 2 theta, and is substantially pure of isopropanol solvate and anhydrate forms of (E)-1-[[[5-(4-chlorophenyl)-2-furanyl]methylene]amino]-3-[4-(4-methyl-1-piperazinyl)butyl]-2,4-imidazolidinedione.

Point 223. The method of Point 210, wherein the hemi-hydrate form is substantially pure of 1-[[[5-(4-chlorophenyl)-2-furanyl]methylene]amino]-3-[4-(chloro)butyl]-2,-4-imidazolidinedione.

Point 224. The method of any of Point 210-223, wherein the hemi-hydrate comprises about 0.0025% or less of 1-[[[5-(4-chlorophenyl)-2-furanyl]methylene]amino]-3-[4-(chloro)butyl]-2,-4-imidazolidinedione.

Point 225. The method of any of Point 210-223, wherein the hemi-hydrate comprises between about 0.0001% and about 0.0025% by weight of 1-[[[5-(4-chlorophenyl)-2-furanyl]methylene]amino]-3-[4-(chloro)butyl]-2,-4-imidazolidinedione.

Point 226. The method of any of Point 210-223, wherein the hemi-hydrate comprises between 0.0001% and 0.0025% by weight of 1-[[[5-(4-chlorophenyl)-2-furanyl]methylene]amino]-3-[4-(chloro)butyl]-2,-4-imidazolidinedione.

Point 227. The method of any of Point 210-223, wherein the hemi-hydrate is substantially pure of 5-(4-chlorophenyl)-2-furancarboxaldehyde.

Point 228. The method of any of Point 210-223, wherein the hemi-hydrate comprises about 0.2% or less of 5-(4-chlorophenyl)-2-furancarboxaldehyde.

Point 229. The method of any of Point 210-223, wherein the hemi-hydrate comprises between about 0.00001% and about 0.2% by weight of 5-(4-chlorophenyl)-2-furancarboxaldehyde.

Point 230. The method of any of Point 210-223, wherein the hemi-hydrate comprises between 0.00001% and 0.2% by weight of 5-(4-chlorophenyl)-2-furancarboxaldehyde.

Point 231. The method of any of Point 210-223, wherein the hemi-hydrate is substantially pure of 1,4-bis[4-[1-[[[5-(4-chlorophenyl)-2-furanyl]methylene]amino]-2,4-dioxo-3imidazolidinyl]butyl]-1-methylpiperazinium chloride.

Point 232. The method of any of Point 210-223, wherein the hemi-hydrate comprises about 0.5% or less of 1,4-bis[4-[1-[[[5-(4-chlorophenyl)-2-furanyl]methylene]amino]-2,4-dioxo-3imidazolidinyl]butyl]-1-methylpiperazinium chloride.

Point 233. The method of any of Point 210-223, wherein the hemi-hydrate comprises between about 0.00001% and about 0.5% by weight of 1,4-bis[4-[1-[[[5-(4-chlorophenyl)-2-furanyl]methylene]amino]-2,4-dioxo-3imidazolidinyl]butyl]-1-methylpiperazinium chloride.

Point 234. The method of any of Point 210-223, wherein the hemi-hydrate comprises between 0.00001% and 0.5% by weight of 1,4-bis[4-[1-[[[5-(4-chlorophenyl)-2-furanyl]methylene]amino]-2,4-dioxo-3imidazolidinyl]butyl]-1-methylpiperazinium chloride.

Point 235. The method of any of Point 210-223, wherein the hemi-hydrate comprises between 0.00001% and 0.4% by weight of 1,4-bis[4-[1-[[[5-(4-chlorophenyl)-2-furanyl]methylene]amino]-2,4-diox-o-3-imidazolidinyl]butyl]-1-methylpiperazinium chloride.

Point 236. The method of any of Point 210-223, wherein the hemi-hydrate is substantially free/pure of 3,3'-[1,4-Piperazinediylbis(butylene)]bis[1-[[[5-(4-chlorophenyl)-2-furan-yl]methylene]amino]-2,4-imidazolidinedione].

Point 237. The method of any of Point 210-223, wherein the hemi-hydrate comprises about 0.3 or less of 3,3'-[1,4-Piperazinediylbis(butylene)]bis[1-[[[5-(4-chlorophenyl)-2-furan-yl]methylene]amino]-2,4-imidazolidinedione].

Point 238. The method of any of Point 210-223, wherein the hemi-hydrate comprises between about 0.00001% and about 0.3% by weight of 3,3'-[1,4-Piperazinediylbis(butylene)]bis[1-[[[5-(4-chlorophenyl)-2-furan-yl]methylene]amino]-2,4-imidazolidinedione].

Point 239. The method of any of Point 210-223, wherein the hemi-hydrate comprises between 0.00001% and 0.3% by weight of 3,3'-[1,4-Piperazinediylbis(butylene)]bis[1-[[[5-(4-chlorophenyl)-2-furan-yl]methylene]amino]-2,4-imidazolidinedione].

Point 240. The method of any of Point 210-223, wherein the hemi-hydrate is substantially pure of 1-[[[5-(4-chlorophenyl)-2-furanyl]methylene]amino]-3-[4-(chloro)butyl]-2,-4-imidazolidinedione and 5-(4-chlorophenyl)-2-furancarboxaldehyde.

Point 241. The method of any of Point 210-223, wherein the hemi-hydrate comprises about 0.0025% or less of 1-[[[5-(4-chlorophenyl)-2-furanyl]methylene]amino]-3-[4-(chloro)butyl]-2,-4-imidazolidinedione and about 0.2% or less of 5-(4-chlorophenyl)-2-furancarboxaldehyde.

Point 242. The method of any of Point 210-223, wherein the hemi-hydrate comprises between about 0.0001% and about 0.0025% by weight of 1-[[[5-(4-chlorophenyl)-2-furanyl]methylene]amino]-3-[4-(chloro)butyl]-2,-4-imidazolidinedione and between about 0.00001% and about 0.2% by weight of 5-(4-chlorophenyl)-2-furancarboxaldehyde.

Point 243. The method of any of Point 210-223, wherein the hemi-hydrate comprises between 0.0001% and 0.0025% by weight of 1-[[[5-(4-chlorophenyl)-2-furanyl]methylene]amino]-3-[4-(chloro)butyl]-2,-4-imidazolidinedione and between about 0.00001% and 0.2% by weight of 5-(4-chlorophenyl)-2-furancarboxaldehyde.

Point 244. The method of any of Point 210-223, wherein the hemi-hydrate is substantially free/pure of 1-[[[5-(4-chlorophenyl)-2-furanyl]methylene]amino]-3-[4-(chloro)butyl]-2,-4-imidazolidinedione, 5-(4-chlorophenyl)-2-furancarboxaldehyde, 1,4-bis[4-[1-[[[5-(4-chlorophenyl)-2-furanyl]methylene]amino]-2,4-dioxo-3imidazolidinyl]butyl]-1-methylpiperazinium chloride, and 3,3'-[1,4-Piperazinediylbis(butylene)]bis[1-[[[5-(4-chlorophenyl)-2-furan-yl]methylene]amino]-2,4-imidazolidinedione].

Point 245. The method of any of Point 210-223, wherein the hemi-hydrate comprises about 0.0025% or less of 1-[[[5-(4-chlorophenyl)-2-furanyl]methylene]amino]-3-[4-(chloro)butyl]-2,-4-imidazolidinedione, about 0.2% or less of 5-(4-chlorophenyl)-2-furancarboxaldehyde, about 0.5% or less of 1,4-bis[4-[1-[[[5-(4-chlorophenyl)-2-furanyl]methylene]amino]-2,4-dioxo-3imidazolidinyl]butyl]-1-methylpiperazinium chloride, and about 0.3% or less of 3,3'-[1,4-Piperazinediylbis(butylene)]bis[1-[[[5-(4-chlorophenyl)-2-furan-yl]methylene]amino]-2,4-imidazolidinedione].

Point 246. The method of any of Point 210-223, wherein the hemi-hydrate comprises between about 0.0001% and about 0.0025% by weight of 1-[[[5-(4-chlorophenyl)-2-furanyl]methylene]amino]-3-[4-(chloro)butyl]-2,-4-imidazolidinedione, between about 0.00001% and about 0.2% by weight of 5-(4-chlorophenyl)-2-furancarboxaldehyde, between about 0.00001% and about 0.5% by weight of 1,4-bis[4-[1-[[[5-(4-chlorophenyl)-2-furanyl]methylene]amino]-2,4-dioxo-3imidazolidinyl]butyl]-1-methylpiperazinium chloride, and between about 0.00001% and about 0.3% by weight of 3,3'-[1,4-Piperazinediylbis(butylene)]bis[1-[[[5-(4-chlorophenyl)-2-furan-yl]methylene]amino]-2,4-imidazolidinedione].

Point 247. The method of any of Point 210-223, wherein the hemi-hydrate comprises between 0.0001% and 0.0025% by weight of 1-[[[5-(4-chlorophenyl)-2-furanyl]methylene]amino]-3-[4-(chloro)butyl]-2,-4-imidazolidinedione, between about 0.00001% and 0.2% by weight of 544-chlorophenyl)-2-furancarboxaldehyde, between 0.00001% and 0.5% by weight of 1,4-bis[4-[1-[[[5-(4-chlorophenyl)-2-furanyl]methylene]amino]-2,4-dioxo-3imidazolidinyl]butyl]-1-methylpiperazinium chloride, and between 0.00001% and 0.3% by weight of 3,3'-[1,4-Piperazinediylbis(butylene)]bis[1-[[[5-(4-chlorophenyl)-2-furan-yl]methylene]amino]-2,4-imidazolidinedione].

Except as otherwise noted, all amounts including quantities, percentages, portions, and proportions, are understood to be modified by the word "about", and amounts are not intended to indicate significant digits. For example, the specific X-ray diffraction peaks disclosed herein are understood by those of ordinary skill in the art to encompass the recited value as well as values within +/−0.2 degrees 2 theta or even+/−0.1 degrees 2 theta of the recited values, to account for minor variances that occur generally across all X-ray diffraction studies.

Except as otherwise noted, the articles "a", "an", and "the" mean "one or more".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications may be made without departing from the spirit and scope of the invention. It is therefore intended to cover in the appended claims all such changes and modifications that are within the scope of this invention.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the composition of matter, and methods described in the specification. As one of ordinary skill in the art will readily appreciate from the disclosure of the present invention, compositions of matter, methods, or steps, presently existing or later to be developed that perform substantially the same function or achieve substantially the same result as the corresponding embodiments described herein may be utilized according to the present invention. Accordingly, the appended claims are intended to include within their scope such processes, compositions of matter, methods, or steps.

What is claimed is:

1. A method for preparing an isopropanol solvate of (E)-1-[[[5-(4-chlorophenyl)-2-furanyl]methylene]amino]-3-[4-(4-methyl-1-piperazinyl)butyl]-2,4-imidazolidinedione dihydrochloride in substantially pure form, wherein the method comprises:

(a) heating a mixture of water and (E)-1-[[[5-(4-chlorophenyl)-2-furanyl]methylene]amino]-3-[4-(4-methyl-1-piperazinyl)butyl]-2,4-imidazolidinedione dihydrochloride to form a heated mixture;

(b) combining the heated mixture with acetone;

(c) isolating a hemi-hydrate of (E)-1-[[[5-(4-chlorophenyl)-2-furanyl]methylene]amino]-3-[4-(4-methyl-1-piperazinyl)butyl]-2,4-imidazolidinedione dihydrochloride; and (d) combining the hemi-hydrate with isopropanol to form the isopropanol solvate of (E)-1-[[[5-(4-chlorophenyl)-2-furanyl]methylene]amino]-3-[4-(4-methyl-1-piperazinyl)butyl]-2,4-imidazolidinedione dihydrochloride.

2. The method of claim 1, wherein the method further comprises recrystallizing the isopropanol solvate in acetone in a step (e).

3. The method of claim 1, wherein the isopropanol solvate comprises between about 9% and about 11% isopropanol by weight.

4. The method of claim 1, wherein the isopropanol solvate has an X-ray diffraction pattern characterized substantially in accordance with the pattern of FIG. 3.

5. The method of claim 1, wherein the isopropanol solvate has a solid-state 13C NMR spectrum characterized substantially in accordance with the solid-state 13C NMR spectrum of FIG. 6.

6. The method of claim 1, wherein the isopropanol solvate has an infrared spectrum characterized substantially in accordance with the infrared spectrum of FIG. 9.

7. The method of claim 1, wherein the isopropanol solvate has a thermogravimetric analysis curve characterized substantially in accordance with the pattern of FIG. 12.

8. The method of claim 1, wherein the isopropanol solvate has X-ray diffraction peaks at 2 theta values of about 4.33, about 9.51, about 12.8, about 17.16, about 18.5 and about 21.53 degrees.

9. The method of claim 1, wherein the isopropanol solvate has IR absorbance peaks at about 3428 and 3390 wave numbers.

10. The method of claim 1, wherein the isopropanol solvate has an X-ray powder diffraction pattern comprising peaks at about 4.33+/−0.2 degrees 2 theta, at about 12.8 +/−0.2 degrees 2 theta, and at about 21.53+/−0.2 degrees 2 theta.

11. The method of claim 1, wherein step (a) comprises heating the mixture to a temperature of about 60-80° C.

12. The method of claim 1, wherein step (b) comprises combining the heated mixture with acetone, maintaining the mixture at a temperature of about 50° C., and then cooling the mixture to induce crystallization.

13. An isopropanol solvate of (E)-1-[[[5-(4-chlorophenyl)-2-furanyl]methylene]amino]-3-[4-(4-methyl-1-piperazinyl)butyl]-2,4-imidazolidinedione dihydrochloride prepared by the process of any of claims 1-12.

* * * * *